US012778941B2

(12) United States Patent
Saffitz et al.

(10) Patent No.: US 12,778,941 B2
(45) Date of Patent: Nov. 3, 2026

(54) SOLUBLE EPOXIDE HYDROLASE (sEH) INHIBITORS AND DUAL COX/sEH INHIBITORS FOR THE TREATMENT OF ARRHYTHMOGENIC CARDIOMYOPATHY

(71) Applicants: BETH ISRAEL DEACONESS MEDICAL CENTER, INC., Boston, MA (US); THE REGENTS OF THE UNIVERSITY OF CALIFORNIA, Oakland, CA (US)

(72) Inventors: Jeffrey E. Saffitz, Waban, MA (US); Bruce D. Hammock, Davis, CA (US); Sung Hee Hwang, Woodland, CA (US)

(73) Assignees: BETH ISRAEL DEACONESS MEDICAL CENTER, INC., Boston, MA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 528 days.

(21) Appl. No.: 18/250,504

(22) PCT Filed: Oct. 25, 2021

(86) PCT No.: PCT/US2021/056497
§ 371 (c)(1),
(2) Date: Apr. 25, 2023

(87) PCT Pub. No.: WO2022/093712
PCT Pub. Date: May 5, 2022

(65) Prior Publication Data

US 2024/0024302 A1 Jan. 25, 2024

Related U.S. Application Data

(60) Provisional application No. 63/105,518, filed on Oct. 26, 2020.

(51) Int. Cl.

| | |
|---|---|
| ***A61K 31/4515*** | (2006.01) |
| ***A61K 31/415*** | (2006.01) |
| ***A61K 31/5377*** | (2006.01) |
| ***A61P 9/06*** | (2006.01) |

(52) U.S. Cl.
CPC ........ *A61K 31/4515* (2013.01); *A61K 31/415* (2013.01); *A61K 31/5377* (2013.01); *A61P 9/06* (2018.01)

(58) Field of Classification Search
CPC .................................................. A61K 31/4515
See application file for complete search history.

(56) References Cited

U.S. PATENT DOCUMENTS 8,242,170 B2 8/2012 Chiamvimonvat et al.
9,096,532 B2 * 8/2015 Hammock ........... C07D 231/40
10,369,141 B2 8/2019 Chiamvimonvat et al.
11,723,929 B2 8/2023 Chiamvimonvat et al.
2009/0291856 A1 11/2009 Haywood et al.

FOREIGN PATENT DOCUMENTS

WO WO-2012112570 A1 8/2012
WO WO-2015148954 A1 10/2015
WO WO-2018231702 A1 12/2018
WO WO-2020146770 A1 7/2020
WO WO-2022093712 A1 5/2022

OTHER PUBLICATIONS

Akdis et al., Arrhythmogenic Cardiomyopathy: Electrical and Structural Phenotypes, Arrhythmia & Electrophysiology Review, 2016 vol. 5, No. 2, pp. 92-101.
U.S. Patent and Trademark Office, International Search Report and Written Opinion for International Application No. PCT/US2021/056497, mailed Jan. 28, 2022, 8 pages.

* cited by examiner

*Primary Examiner* — Golam M Shameem
(74) *Attorney, Agent, or Firm* — Mintz, Levin, Cohn, Ferris, Glovsky and Popeo, P.C.

(57) ABSTRACT

Provided herein are methods of preventing, mitigating, decreasing, reversing and/or treating Arrhythmogenic Cardiomyopathy (ACM) in a subject in need thereof, comprising administering to the subject an effective amount of a compound of Formula I, a compounds of Formula II, or a compound of Formula III (I)

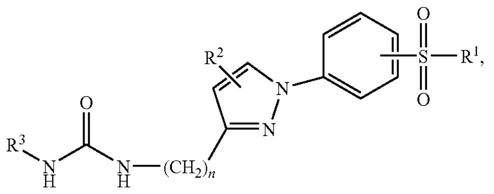

(II)

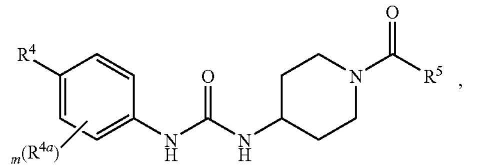

(III)

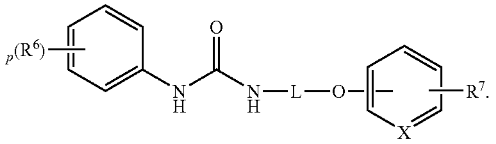

wherein $R^1$, $R^2$, $R^3$, n, $R^4$, $R^{4a}$, $R^5$, m, $R^6$, $R^7$, and p are as defined herein.

8 Claims, 11 Drawing Sheets

SOLUBLE EPOXIDE HYDROLASE (sEH) INHIBITORS AND DUAL COX/sEH INHIBITORS FOR THE TREATMENT OF ARRHYTHMOGENIC CARDIOMYOPATHY

CROSS-REFERENCE TO RELATED APPLICATIONS

This application is a U.S. National Stage Entry of International Application No. PCT/US2021/056497, filed Oct. 25, 2021, which claims priority benefit of U.S. Provisional Application No. 63/105,518, filed on Oct. 26, 2020, each which is herein incorporated by reference in its entirety for all purposes.

STATEMENT OF GOVERNMENTAL SUPPORT

This work was supported in part by the American Heart Association, Grant No. 18TPA34170559, and NIH Grant No. R01 HL148348-01A1. The Government has certain rights in this invention.

BACKGROUND

Arrhythmogenic cardiomyopathy (ACM) is a progressive myocardial disease primarily involving the right ventricle (although the disease can begin in the left ventricle). ACM is predominantly characterized by fibrous and fatty deposits in the ventricular myocardium. The major clinical manifestation of this disease is patients exhibiting ventricular arrhythmias. These ventricular arrhythmias can limit blood flow, and in severe cases can cause sudden death.

ACM patients most commonly have identified hereditary mutations (familial ACM), although some ACM patients have been diagnosed without any known hereditary mutations (non-familial ACM). About 60-70% of patients who fulfill clinical/imaging/ECG criteria of ACM will have a mutation in the desmosome. It is believed that most of the remaining patients have a mutation that has not yet been identified. Both populations (familial and non familial) of patients display similar phenotypic expression.

To date, the only effective treatment for ACM is an implantable defibrillator. Although the defibrillator can extend the life of patients, this technique does nothing to treat the underlying heart muscle disease nor prevent its progression. As such, there is a need in the art to identify and develop drug targets that can treat and ideally prevent disease progression.

SUMMARY

In some aspects, provided herein are methods of preventing, mitigating, decreasing, reversing and/or treating Arrhythmogenic Cardiomyopathy in a subject in need thereof, comprising administering to the subject a compound of Formula II (II)

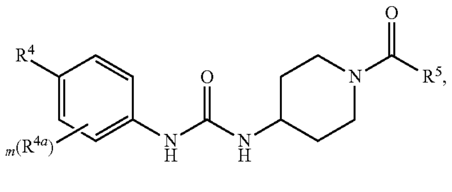

wherein $R^4$, $R^{4a}$, $R^5$, and m are as defined herein.

In some aspects, provided herein are methods of preventing, mitigating, decreasing, reversing and/or treating Arrhythmogenic Cardiomyopathy in a subject in need thereof, comprising administering to the subject a compound having the Formula:

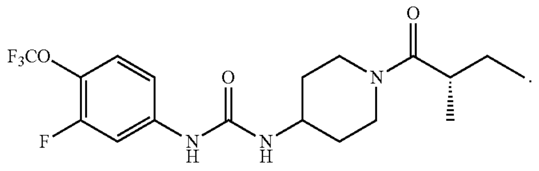 [SMILES: CC[C@H](C)C(=O)N1CCC(NC(=O)Nc2ccc(OC(F)(F)F)c(F)c2)CC1]

In some aspects, provided herein are methods of preventing, mitigating, decreasing, reversing and/or treating Arrhythmogenic Cardiomyopathy in a subject in need thereof, comprising administering to the subject a compound of Formula I (I)

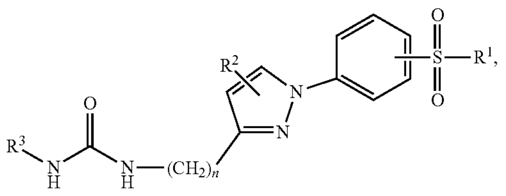

wherein $R^1$, $R^2$, $R^3$, and n are as defined herein.

In some aspects, provided herein are methods of preventing, mitigating, decreasing, reversing and/or treating Arrhythmogenic Cardiomyopathy in a subject in need thereof, comprising administering to the subject a compound of Formula III (III)

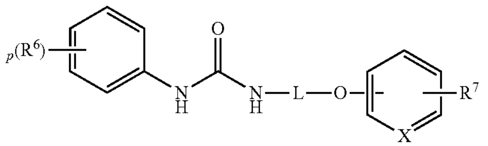

wherein $R^6$, $R^7$, and p are as defined herein.

In some embodiments, the compound of Formula I, Formula II, or Formula III is administered orally, buccally, transmucosally or topically. In some embodiments, the compound of Formula I, Formula II for Formula III is administered orally.

DETAILED DESCRIPTION

Definitions

Figure 1A:
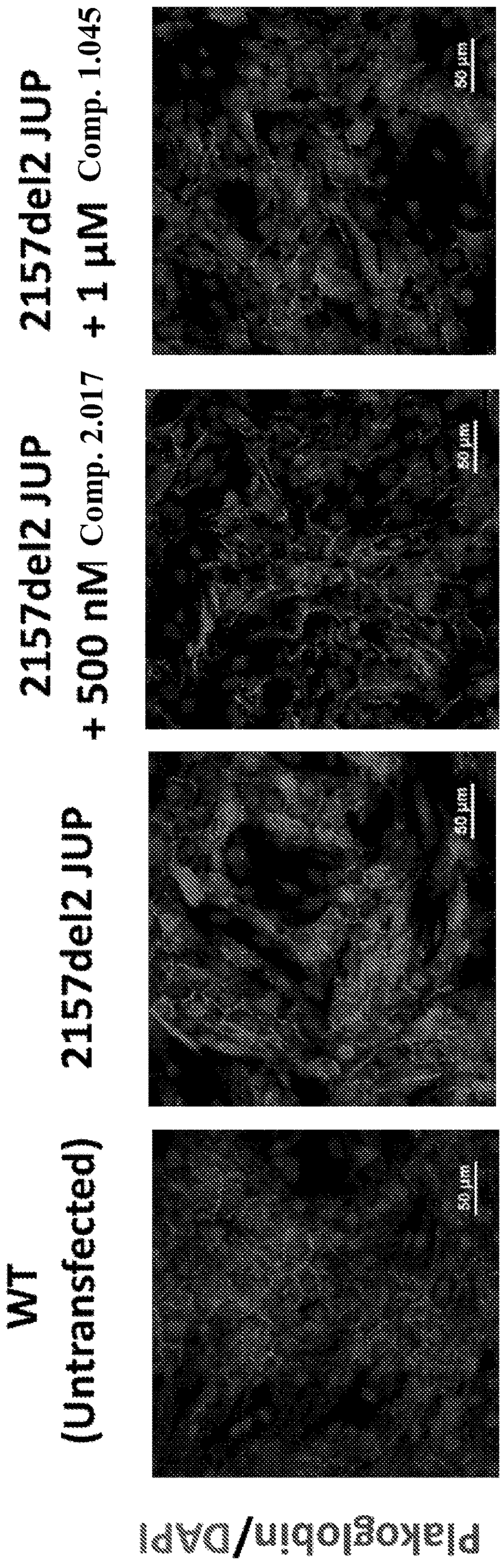
FIG. 1A-D shows the effects of compounds of Formula I (2.017) and Formula II (1.045) on ACM rat myocytes expressing a pathogenic variant (Jup2157del2) in the desmosomal protein, plakoglobin (A). Compared to control (WT) cells, Jup2157del2 cells show intracellular/intranuclear redistribution of signal for plakoglobin, loss of cell surface signal for Cx43 (B), nuclear signal for pRelA/p65 (indicating activation of NFκB) (C), and myocyte apoptosis (TUNEL+nuclei) (D). These effects are reversed by treating cells with the Compound 2.017 (500 nM) and Compound 1.045 (1 μM). By contrast, exposure of Jup2157del2 cells to 14,15-EE-5(Z)E (EEZE; 10 μM), a downstream product of soluble epoxide hydrolase, intensifies these ACM disease features (data not shown).
Figure 1B:
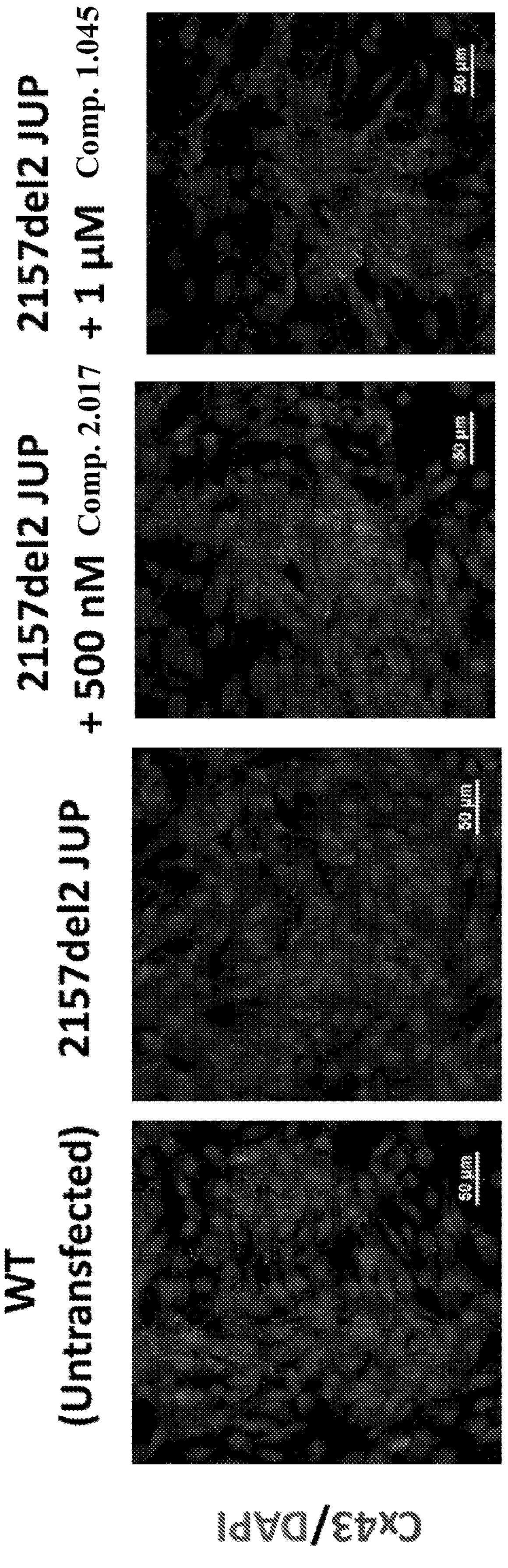

Units, prefixes, and symbols are denoted in their Systeme International de Unites (SI) accepted form. Numeric ranges are inclusive of the numbers defining the range. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon group, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of alkenyl groups include vinyl, 2-propenyl, crotyl, 2-isopentenyl, 2-(butadienyl), 2,4-pentadienyl and 3-(1,4-pentadienyl). Examples of alkynyl groups include ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1] heptane, bicyclo[2.2.2]octane, etc. The bicyclic or polycyclic rings may be fused, bridged, spiro or a combination thereof. The term "heterocycloalkyl" or "heterocyclyl" refers to a cycloalkyl group having the indicated number of ring members, and which contain from one to three heteroatoms selected from N, O, and S, wherein the nitrogen and sulfur atoms are optionally oxidized, and the nitrogen atom (s) are optionally quaternized. The heterocycloalkyl may be a monocyclic, a bicyclic or a polycylic ring system. The bicyclic or polycyclic rings may be fused, bridged, spiro or a combination thereof. It is understood that the recitation for $C_{412}$ heterocyclyl, refers to a group having from 4 to 12 ring members where at least one of the ring members is a heteroatom. Non limiting examples of heterocycloalkyl groups include pyrrolidine, imidazolidine, pyrazolidine, butyrolactam, valerolactam, imidazolidinone, tetrazolone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "hydroxyalkyl" or "alkyl-OH" refers to an alkyl group, as defined above, where at least one (and up to three) of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), and 2,3-dihydroxypropyl.

The term "aryl" means, unless otherwise stated, an aromatic hydrocarbon group which can be a single ring or multiple rings (up to three rings) which are fused together or linked covalently. Non-limiting examples of aryl groups include phenyl, naphthyl and biphenyl. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S), phosphorus (P) and silicon (Si).

The disclosure herein further relates to prodrugs and bioisosteres thereof. Suitable bioisosteres, for example, will include carboxylate replacements (phosphonic acids, phosphinic acids, sulfonic acids, sulfinic acids, and acidic heterocyclic groups such as tetrazoles). Suitable prodrugs will include those conventional groups known to hydrolyze and/or oxidize under physiological conditions to provide a compound of Formula I.

The terms "patient" and "subject" include primates (especially humans), domesticated companion animals (such as dogs, cats, horses, and the like) and livestock (such as cattle, pigs, sheep, and the like).

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure. For example, the compounds may be prepared such that any number of hydrogen atoms are replaced with a deuterium ($^2H$) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^{2}H$) or carbon-13 ($^{13}C$). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

"cis-Epoxyeicosatrienoic acids" ("EETs") are biomediators synthesized by cytochrome P450 epoxygenases.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs. 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

The term "therapeutically effective amount" refers to that amount of the compound being administered sufficient to prevent, mitigate, decrease, reverse the development of one or more of the symptoms of the disease, condition or disorder being treated.

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

The terms "systemic administration" and "systemically administered" refer to a method of administering agent to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" interchangeably refers to a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., *rattus*, murine, *lagomorpha*, hamster).

General

As described above, ACM is a progressive disease characterized by increased risk of sudden death. Despite a growing understanding of the pathology and etiology of this diseases, there are remarkably few methods for treatment. In fact, the only approved therapy is an implantable defibrillator. This device helps treat ventricular arrhythmias, but does not treat the underlying heart muscle disease nor prevent its progression.

Unlike other ischemic or exogenous myocardial disorders (e.g., heart attack, infection, etc.), the heart muscles themselves appear to drive ACM disease pathogenesis seemingly, in part, due to inflammation.

The inventors of the preset disclosure have identified that administering a subset of soluble epoxide hydrolase inhibitors (and some dual COX/sEH inhibitors) to subjects with ACM provides a surprisingly robust amelioration of ACM progression. Without being bound to any particular theory, it is believed that the currently described compounds not only treats the underlying cause of ACM, but also stop the progression of this disease.

Since disease treatment likely requires chronic administration, the use of sEH inhibitors advantageously avoids the use of more potent immunosuppressors, which can make the subjects with ACM more susceptible to other (potentially life threatening) diseases. Additionally, unlike immunosuppression, which requires pharmacologic inhibition of one or more components of the immune response, resolution of inflammation with sEH inhibitors is mediated by endogenous molecules that function to modulate and reduce active inflammatory responses without compromising the ability of the immune system to react to infectious agents or other type of injury requiring an adaptive response.

Collectively, the currently described discovery represents a major breakthrough in the treatment and management of ACM.

Methods of Preventing, Mitigating, Decreasing, Reversing and/or Treating Arrhythmogenic Cardiomyopathy (ACM)

Provided herein are methods of preventing, reducing, ameliorating, mitigating, slowing the progression and/or treating Arrhythmogenic Cardiomyopathy (ACM) using compounds of Formula I, compounds of Formula II, compounds of Formula III or a combination thereof.

Subjects who may benefit from these treatment methods are those who are exhibiting symptoms of or at risk for ACM. For example, the subject may be diagnosed with or be suspected of having ACM. Symptoms of ACM include without limitation, e.g., heart palpitations, dizziness, fainting, shortness of breath, chest pain, fatigue, swelling in the legs and other areas, persistent cough, or a combination thereof.

In some aspects, provided herein are methods of preventing Arrhythmogenic Cardiomyopathy (ACM) in a human subject comprising administering to the human subject a therapeutically effective amount of a compound of Formula I, a compound of Formula II, or a compound of Formula III.

In some aspects, provided herein are methods of reducing Arrhythmogenic Cardiomyopathy (ACM) in a human subject comprising administering to the human subject a therapeutically effective amount of a compound of Formula I, a compound of Formula II, or a compound of Formula III.

In some aspects, provided herein are methods of ameliorating Arrhythmogenic Cardiomyopathy (ACM) in a human subject comprising administering to the human subject a therapeutically effective amount of a compound of Formula I, a compound of Formula II, or a compound of Formula III.

In some aspects, provided herein are methods of mitigating Arrhythmogenic Cardiomyopathy (ACM) in a human subject comprising administering to the human subject a therapeutically effective amount of a compound of Formula I, a compound of Formula II, or a compound of Formula III.

In some aspects, provided herein are methods of slowing the progression Arrhythmogenic Cardiomyopathy (ACM) in a human subject comprising administering to the human subject a therapeutically effective amount of a compound of Formula I, a compound of Formula II, or a compound of Formula III.

In some aspects, provided herein are methods of treating Arrhythmogenic Cardiomyopathy (ACM) in a human subject comprising administering to the human subject a therapeutically effective amount of a compound of Formula I, a compound of Formula II, or a compound of Formula III.

In some embodiments, the provided methods of preventing, reducing, ameliorating, mitigating, slowing the progression and/or treating Arrhythmogenic Cardiomyopathy (ACM) comprise administering a therapeutically effective amount of a compound of Formula I. In some embodiments, the provided methods of preventing, reducing, ameliorating, mitigating, slowing the progression and/or treating Arrhythmogenic Cardiomyopathy (ACM) comprise administering a therapeutically effective amount of a compound of Formula II. In some embodiments, the provided methods of preventing, reducing, ameliorating, mitigating, slowing the progression and/or treating Arrhythmogenic Cardiomyopathy (ACM) comprise administering a therapeutically effective amount of a compound of Formula III. Compounds of Formula I, Formula II, Formula III as well as subembodiments thereof are further described in the following section.

In some embodiments, the ACM in the subject is familial ACM. In some embodiments, the familial ACM is characterized by a mutation in the desmosome. Known mutations in the densome that cause ACM or ACM like symptoms include, but are not limited to, mutations in a gene selected from plakophilin 2, desmocollin 2, desmoglein 2, desmopakin, and plakoglobin.

In some embodiments, the familial ACM is characterized by a mutation in a gene selected from the group consisting of α-T-catenin, ryanodine receptor 2 phospholamban, lamin A/C, transmembrane protein 43, desmin, titin, and transforming growth factor β3.

Overall, a number of mutations have been identified that cause ACM or ACM like symptoms. These mutations includes those discussed in Akdis et al. *Arrhythm Electrophysiol Rev.* 2016 5(2):90-101. doi: 10.15420/AER.2016.4.3. The contents of which is incorporated by reference herein for all purposes.

In varying embodiments, the subject is a child, an adult, or an elderly individual. In varying embodiments, the subject is a mammal, for example, human, a non-human primate, canine, feline, equine, bovine, ovine, porcine, *lagomorpha*, murine, or *rattus*. In some embodiments, the subject is a human.

In other embodiments, subjects who benefit from the described treatments include subjects with arrhythmogenic forms of dilated cardiomyopathy (aDCM). Methods for identifying and diagnosing aDCM are known in the art. In some embodiments, the aDCM is familial aDCM. In some embodiments, the familial aDCM is characterized by a mutation in a gene selected from the group consisting of phospholamban, laminA, and filamin C. In other embodiments, subjects who benefit from the described treatments include subjects with Brugada syndrome. Methods for identifying and diagnosing Brugada syndrome are known in the art. The current application embraces methods of preventing, reducing, ameliorating, mitigating, slowing the progression and/or treating aDCM and Brugada syndrome in subject is need thereof comprising administering to the subject an effective amount of a compound of Formula I or a compound of Formula II.

Agents Useful in Preventing, Mitigating, Decreasing, Reversing and/or Treating Arrhythmogenic Cardiomyopathy (ACM)

Agents that are useful in the preventing, mitigating, decreasing, reversing and/or treating Arrhythmogenic Cardiomyopathy (ACM) include soluble epoxide hydrolase (sEH) inhibitors of Formula II or Formula III and dual cyclooxygenase-2 (COX-2)/soluble epoxide hydrolase (sEH) inhibitors of Formula I.

a. Compounds of Formula II

Compounds of Formula II are characterized by the formula (II)

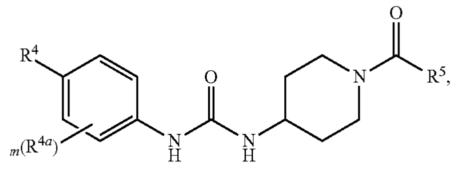

wherein $R^4$ is —$OCF_3$ or —$CF_3$;

each $R^{4a}$ is independently selected from the group consisting of H, halogen, $C_{1-6}$ alkyl, $C_{1-6}$ alkoxy, $C_{1-6}$ haloalkyl, $C_{1-6}$ haloalkoxy, —O-aryl, 5- to 6-membered heterocycloalkyl having 1 to 3 heteroatoms as ring vertices selected from N, O, and S, —OH, —$NO_2$, and —C(O)$OR^{4b}$;

$R^5$ is selected from the group consisting of $C_{1-6}$ alkyl, $C_{1-6}$ haloalkyl, $C_{1-6}$ hydroxyalkyl, $C_{1-6}$ alkoxy, $C_{1-6}$ haloalkoxy, —$X^5$—$C_{3-6}$ cycloalkyl, —$X^5$-3- to 6-membered heterocycloalkyl having 1 to 3 heteroatoms as ring vertices selected from N, O, and S, and —$X^5$-5- to 6-membered heteroaryl having 1 to 3 heteroatom as ring vertices selected from N, O, and S, wherein $R^5$ is optionally substituted with from 1 to 3 substituents selected from the group consisting of $C_{1-4}$ alkyl, $C_{1-4}$ haloalkyl, hydroxyl, —C(O)$OR^{5a}$, and —$C_{1-4}$-alkylene-C(O)$OR^{5a}$;

$X^5$ is selected from a bond and $C_{1-3}$ alkylene $R^{4b}$ and $R^{5a}$ are each independently H or $C_{1-6}$ alkyl; and subscript m is an integer from 0 to 2.

In some embodiments, the compound of Formula II is represented by Formula IIa (IIa)

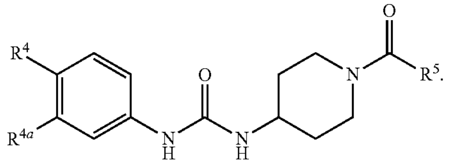

In some embodiments, $R^4$ in Formula II or IIa is —$OCF_3$.

In some embodiments, $R^4$ in Formula II or IIa is —$CF_3$.

In some embodiments, m is 1 and $R^{4a}$ in Formula II or IIa is selected from the group consisting of —$CF_3$, Cl, Br, F, and —$OCF_3$.

In some embodiments, m is 1 and $R^{4a}$ in Formula II or IIa is F.

In some embodiments, $R^5$ in Formula II or IIa is selected from the group consisting of $C_{1-6}$ alkyl, $C_{1-6}$ haloalkyl, $C_{1-6}$ hydroxyalkyl, $C_{1-6}$ alkoxy, $C_{1-6}$ haloalkoxy, $C_{3-6}$ cycloalkyl, and 3- to 6-membered heterocycloalkyl having 1 to 3 heteroatoms as ring vertices selected from N, O, and S, and -5- to 6-membered heteroaryl having 1 to 3 heteroatom as ring vertices selected from N, O, and S.

In some embodiments, $R^5$ in Formula II or IIa is selected from the group consisting of $C_{1-6}$ alkyl, $C_{1-6}$ haloalkyl and $C_{1-6}$ hydroxyalkyl.

In some embodiments, compounds of Formula II are selected from a compound in Table 1.

TABLE 1

| Compounds of Formula II and related compounds Structure | |
|---|---|
| 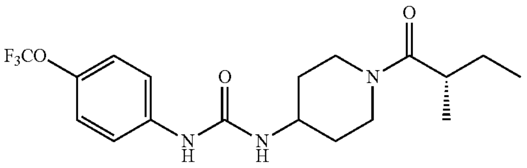 [SMILES: CC[C@H](C)C(=O)N1CCC(NC(=O)Nc2ccc(OC(F)(F)F)cc2)CC1] | 1.001 |
| 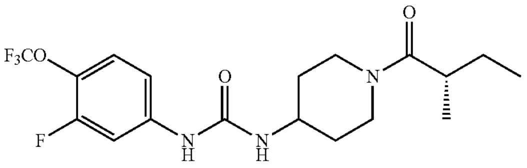 [SMILES: CC[C@H](C)C(=O)N1CCC(NC(=O)Nc2ccc(OC(F)(F)F)c(F)c2)CC1] | 1.002 |
| 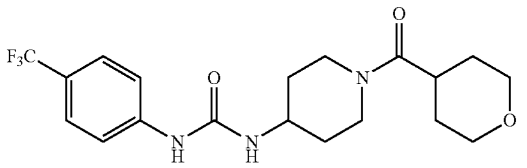 | 1.003 |
| 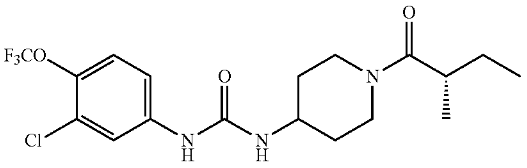 [SMILES: CC[C@H](C)C(=O)N1CCC(NC(=O)Nc2ccc(OC(F)(F)F)c(Cl)c2)CC1] | 1.004 |
| 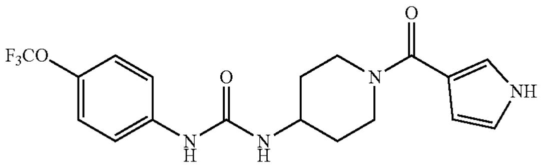 [SMILES: O=C(Nc1ccc(OC(F)(F)F)cc1)NC1CCN(C(=O)c2cc[nH]c2)CC1] | 1.005 |

TABLE 1-continued
| Compounds of Formula II and related compounds<br>Structure | |
| --- | --- |
| 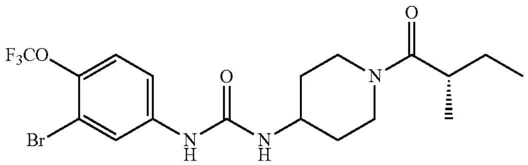 [SMILES: CC[C@H](C)C(=O)N1CCC(NC(=O)Nc2ccc(OC(F)(F)F)c(Br)c2)CC1] | 1.006 |
| 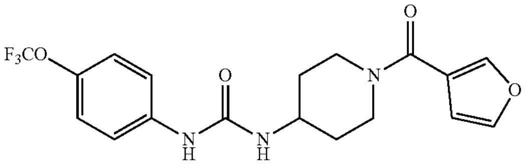 [SMILES: O=C(Nc1ccc(OC(F)(F)F)cc1)NC1CCN(C(=O)c2ccoc2)CC1] | 1.007 |
| 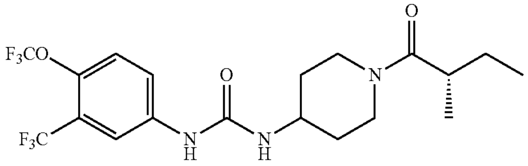 [SMILES: CC[C@H](C)C(=O)N1CCC(NC(=O)Nc2ccc(OC(F)(F)F)c(C(F)(F)F)c2)CC1] | 1.008 |
| 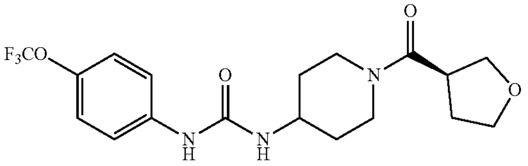 [SMILES: O=C(Nc1ccc(OC(F)(F)F)cc1)NC1CCN(C(=O)[C@@H]2CCOC2)CC1] | 1.009 |
| 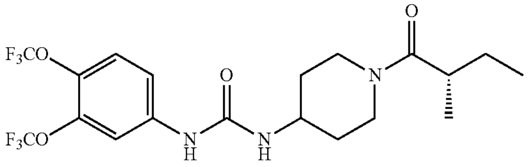 [SMILES: CC[C@H](C)C(=O)N1CCC(NC(=O)Nc2ccc(OC(F)(F)F)c(OC(F)(F)F)c2)CC1] | 1.010 |
| 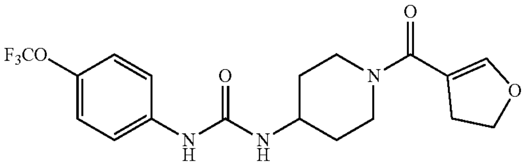 [SMILES: O=C(Nc1ccc(OC(F)(F)F)cc1)NC1CCN(C(=O)C2=COCC2)CC1] | 1.011 |
| 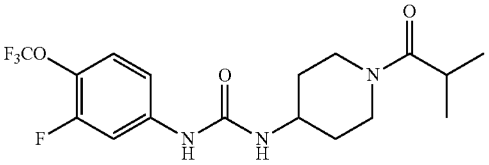 [SMILES: CC(C)C(=O)N1CCC(NC(=O)Nc2ccc(OC(F)(F)F)c(F)c2)CC1] | 1.012 |
| 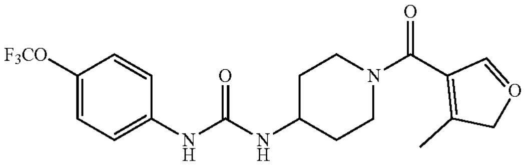 | 1.013 |
| 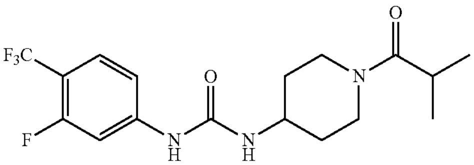 [SMILES: CC(C)C(=O)N1CCC(NC(=O)Nc2ccc(C(F)(F)F)c(F)c2)CC1] | 1.014 |

TABLE 1-continued
| Compounds of Formula II and related compounds Structure | |
|---|---|
| 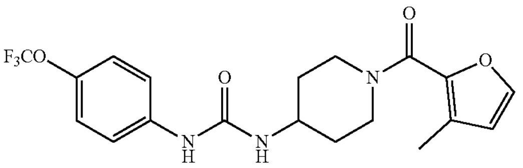 [SMILES: Cc1ccoc1C(=O)N1CCC(NC(=O)Nc2ccc(OC(F)(F)F)cc2)CC1] | 1.015 |
| 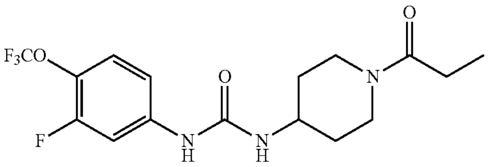 [SMILES: CCC(=O)N1CCC(NC(=O)Nc2ccc(OC(F)(F)F)c(F)c2)CC1] | 1.016 |
| 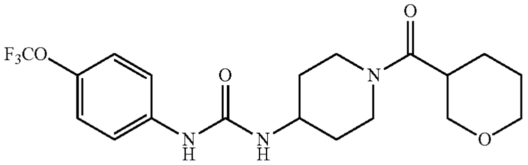 [SMILES: O=C(Nc1ccc(OC(F)(F)F)cc1)NC1CCN(C(=O)C2CCCOC2)CC1] | 1.017 |
| 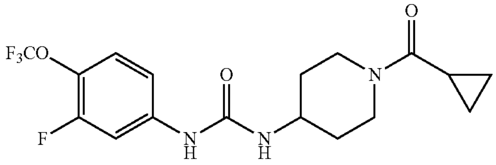 [SMILES: O=C(Nc1ccc(OC(F)(F)F)c(F)c1)NC1CCN(C(=O)C2CC2)CC1] | 1.018 |
| 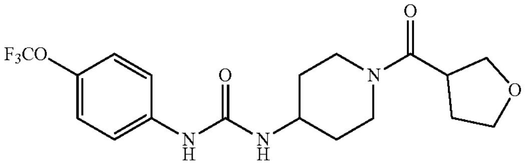 [SMILES: O=C(Nc1ccc(OC(F)(F)F)cc1)NC1CCN(C(=O)C2CCOC2)CC1] | 1.019 |
| 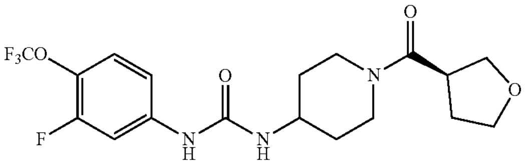 [SMILES: O=C(Nc1ccc(OC(F)(F)F)c(F)c1)NC1CCN(C(=O)[C@@H]2CCOC2)CC1] | 1.020 |
| 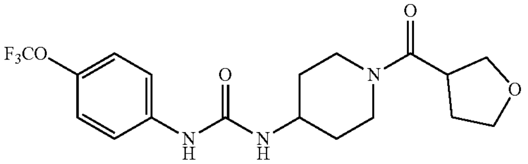 [SMILES: O=C(Nc1ccc(OC(F)(F)F)cc1)NC1CCN(C(=O)C2CCOC2)CC1] | 1.021 |
| 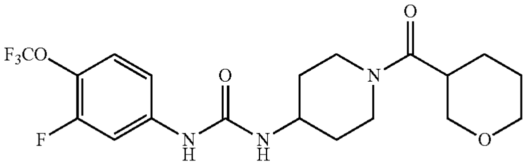 [SMILES: O=C(Nc1ccc(OC(F)(F)F)c(F)c1)NC1CCN(C(=O)C2CCCOC2)CC1] | 1.022 |

TABLE 1-continued
| Compounds of Formula II and related compounds<br>Structure | |
|---|---|
| 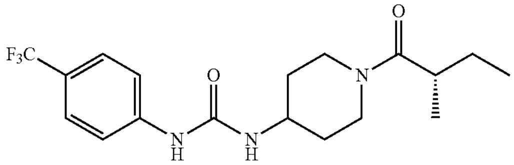 [SMILES: CC[C@H](C)C(=O)N1CCC(NC(=O)Nc2ccc(C(F)(F)F)cc2)CC1] | 1.023 |
| 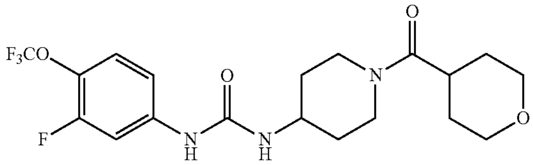 [SMILES: O=C(Nc1ccc(OC(F)(F)F)c(F)c1)NC1CCN(C(=O)C2CCOCC2)CC1] | 1.024 |
| 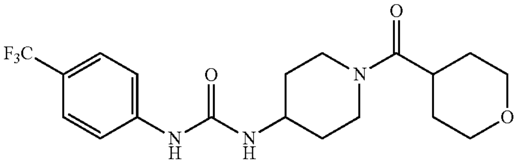 [SMILES: O=C(Nc1ccc(C(F)(F)F)cc1)NC1CCN(C(=O)C2CCOCC2)CC1] | 1.025 |
| 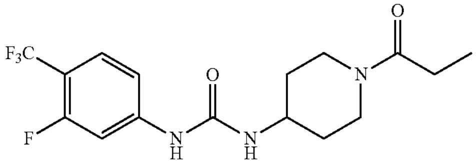 [SMILES: CCC(=O)N1CCC(NC(=O)Nc2ccc(C(F)(F)F)c(F)c2)CC1] | 1.026 |
| 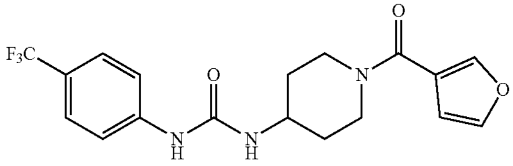 [SMILES: O=C(Nc1ccc(C(F)(F)F)cc1)NC1CCN(C(=O)c2ccoc2)CC1] | 1.027 |
| 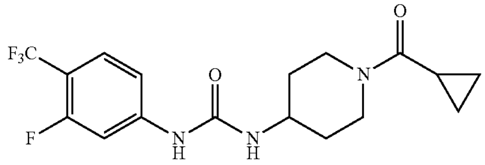 [SMILES: O=C(Nc1ccc(C(F)(F)F)c(F)c1)NC1CCN(C(=O)C2CC2)CC1] | 1.028 |
| 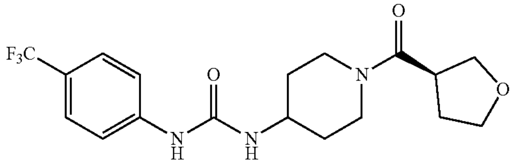 [SMILES: O=C(Nc1ccc(C(F)(F)F)cc1)NC1CCN(C(=O)[C@@H]2CCOC2)CC1] | 1.029 |
| 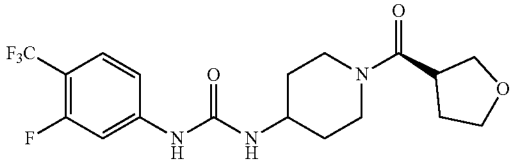 | 1.030 |
| 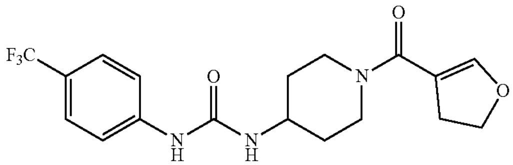 [SMILES: O=C(Nc1ccc(C(F)(F)F)cc1)NC1CCN(C(=O)C2=COCC2)CC1] | 1.031 |

TABLE 1-continued
| Compounds of Formula II and related compounds Structure | |
|---|---|
| 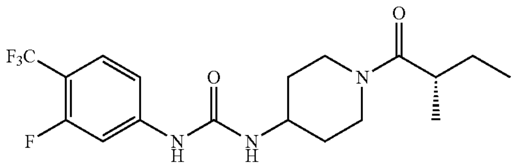 [SMILES: CC[C@H](C)C(=O)N1CCC(NC(=O)Nc2ccc(C(F)(F)F)c(F)c2)CC1] | 1.032 |
| 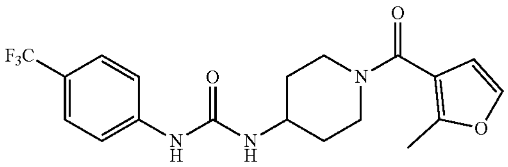 [SMILES: Cc1occc1C(=O)N1CCC(NC(=O)Nc2ccc(C(F)(F)F)cc2)CC1] | 1.033 |
| 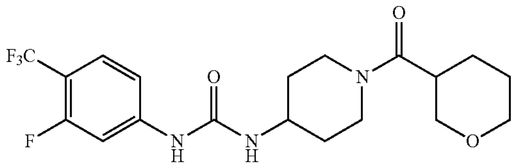 [SMILES: O=C(Nc1ccc(C(F)(F)F)c(F)c1)NC1CCN(C(=O)C2CCCOC2)CC1] | 1.034 |
| 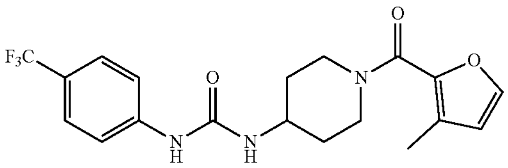 [SMILES: Cc1ccoc1C(=O)N1CCC(NC(=O)Nc2ccc(C(F)(F)F)cc2)CC1] | 1.035 |
| 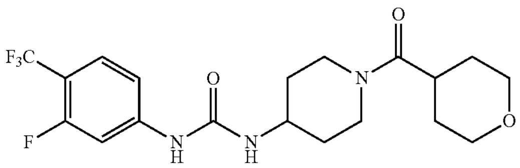 [SMILES: O=C(Nc1ccc(C(F)(F)F)c(F)c1)NC1CCN(C(=O)C2CCOCC2)CC1] | 1.036 |
| 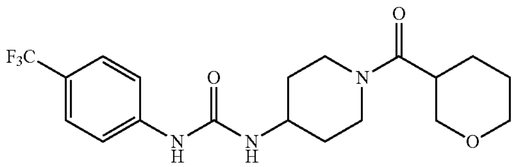 [SMILES: O=C(Nc1ccc(C(F)(F)F)cc1)NC1CCN(C(=O)C2CCCOC2)CC1] | 1.037 |
| 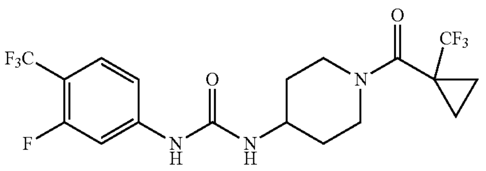 [SMILES: O=C(Nc1ccc(C(F)(F)F)c(F)c1)NC1CCN(C(=O)C2(C(F)(F)F)CC2)CC1] | 1.038 |
| 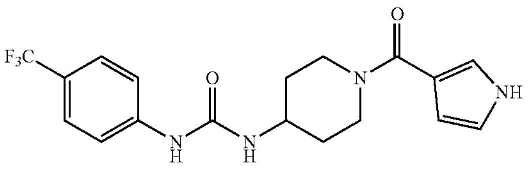 [SMILES: O=C(Nc1ccc(C(F)(F)F)cc1)NC1CCN(C(=O)c2cc[nH]c2)CC1] | 1.039 |

TABLE 1-continued
| Compounds of Formula II and related compounds Structure | |
|---|---|
| 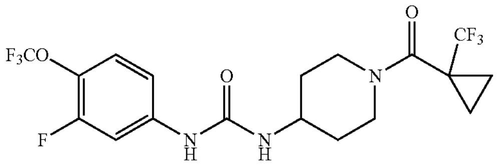 [SMILES: O=C(Nc1ccc(OC(F)(F)F)c(F)c1)NC1CCN(C(=O)C2(C(F)(F)F)CC2)CC1] | 1.040 |
| 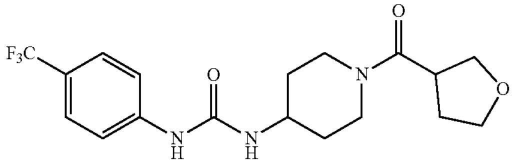 [SMILES: O=C(Nc1ccc(C(F)(F)F)cc1)NC1CCN(C(=O)C2CCOC2)CC1] | 1.041 |
| 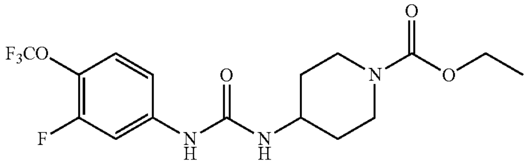 [SMILES: CCOC(=O)N1CCC(NC(=O)Nc2ccc(OC(F)(F)F)c(F)c2)CC1] | 1.042 |
| 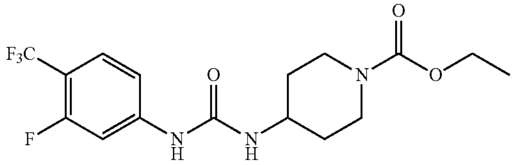 [SMILES: CCOC(=O)N1CCC(NC(=O)Nc2ccc(C(F)(F)F)c(F)c2)CC1] | 1.043 |
| 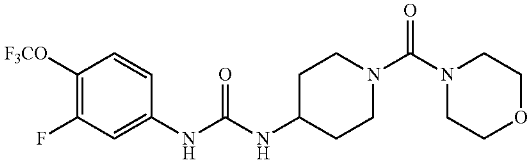 [SMILES: O=C(Nc1ccc(OC(F)(F)F)c(F)c1)NC1CCN(C(=O)N2CCOCC2)CC1] | 1.044 |
| 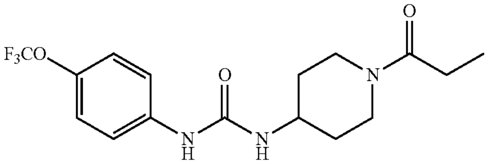 [SMILES: CCC(=O)N1CCC(NC(=O)Nc2ccc(OC(F)(F)F)cc2)CC1] | 1.045 |
| 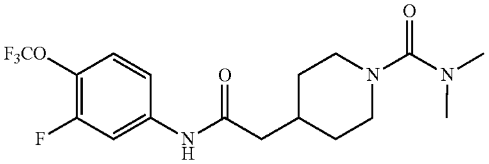 [SMILES: CN(C)C(=O)N1CCC(CC(=O)Nc2ccc(OC(F)(F)F)c(F)c2)CC1] | 1.046 |
| 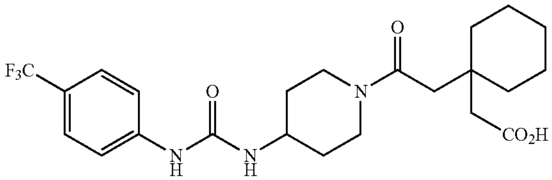 [SMILES: O=C(O)CC1(CC(=O)N2CCC(NC(=O)Nc3ccc(C(F)(F)F)cc3)CC2)CCCCC1] | 1.047 |

TABLE 1-continued
| Compounds of Formula II and related compounds<br>Structure | |
|---|---|
| 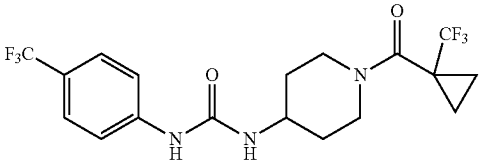 [SMILES: O=C(Nc1ccc(C(F)(F)F)cc1)NC1CCN(C(=O)C2(C(F)(F)F)CC2)CC1] | 1.048 |
| 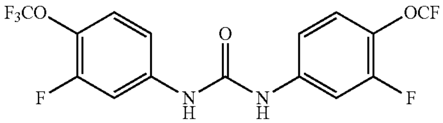 | 1.049 |
| 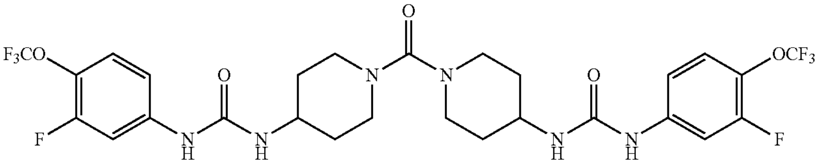 [SMILES: O=C(Nc1ccc(OC(F)(F)F)c(F)c1)NC1CCN(C(=O)N2CCC(NC(=O)Nc3ccc(OC(F)(F)F)c(F)c3)CC2)CC1] | 1.050 |
| 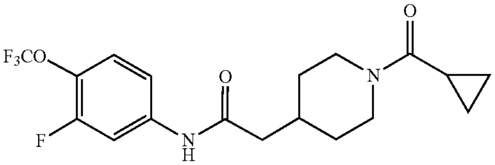 [SMILES: O=C(CC1CCN(C(=O)C2CC2)CC1)Nc1ccc(OC(F)(F)F)c(F)c1] | 1.051 |
| 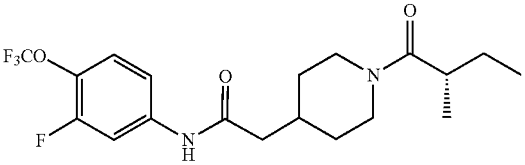 [SMILES: CC[C@H](C)C(=O)N1CCC(CC(=O)Nc2ccc(OC(F)(F)F)c(F)c2)CC1] | 1.052 |
| 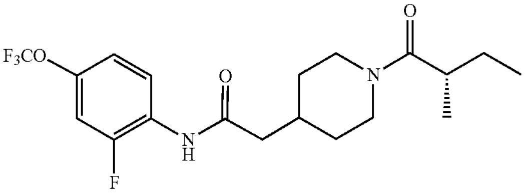 [SMILES: CC[C@H](C)C(=O)N1CCC(CC(=O)Nc2ccc(OC(F)(F)F)cc2F)CC1] | 1.053 |
In some embodiments, the compounds of Formula II has the structure
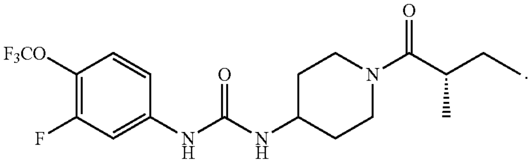 [SMILES: CC[C@H](C)C(=O)N1CCC(NC(=O)Nc2ccc(OC(F)(F)F)c(F)c2)CC1]
Further characterization data of the compounds of Table 1 are provided below in Table 2 and Table 3.

TABLE 2
Physical properties and human in vitro data for compounds of Fromula II and related compounds
| Structure | Physical Properties MW | Sol[a] (ug/mL) | Sol[b] (ug/mL) at pH3 | mp (° C.) | Exp. LogP | Human In vitro Ki (nM) | $t_{1/2}$ (min)[c] |
|---|---|---|---|---|---|---|---|
| 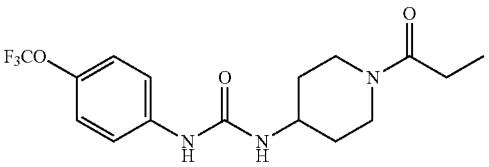 [SMILES: CCC(=O)N1CCC(NC(=O)Nc2ccc(OC(F)(F)F)cc2)CC1] | 359.34 | 60 | 60 | 198.2-200.8 | 3.23 | 0.64 ± 0.09 | 11 |
| 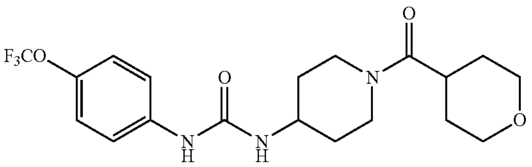 [SMILES: O=C(Nc1ccc(OC(F)(F)F)cc1)NC1CCN(C(=O)C2CCOCC2)CC1] | 415.11 | 91 | 1295 | 177.4-178.7 | 3.26 | 1.43 ± 0.01 | 14 |
| 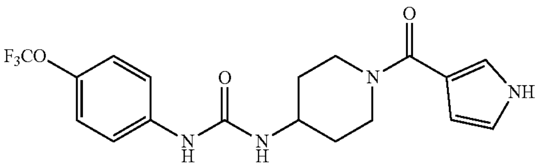 [SMILES: O=C(Nc1ccc(OC(F)(F)F)cc1)NC1CCN(C(=O)c2cc[nH]c2)CC1] | 396.14 | 43 | 58 | 131.4-136.1 | 3.34 | 0.64 ± 0.17 | 15 |
| 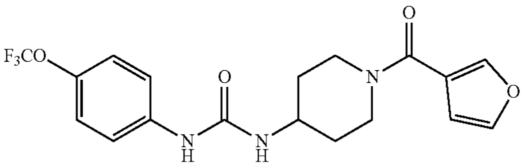 [SMILES: O=C(Nc1ccc(OC(F)(F)F)cc1)NC1CCN(C(=O)c2ccoc2)CC1] | 397.12 | 7.6 | 26 | 181.4-184.5 | 3.63 | 0.33 ± 0.34 | 17 |
| 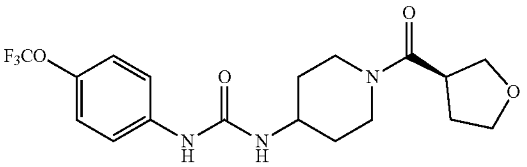 [SMILES: O=C(Nc1ccc(OC(F)(F)F)cc1)NC1CCN(C(=O)[C@@H]2CCOC2)CC1] | 401.16 | 23 | 65 | 180.5-181.7 | 3.38 | 1.41 ± 0.11 | 17 |
| 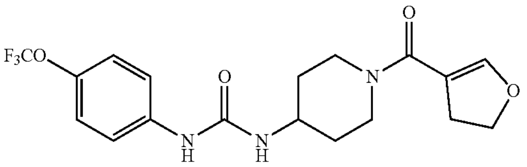 [SMILES: O=C(Nc1ccc(OC(F)(F)F)cc1)NC1CCN(C(=O)C2=COCC2)CC1] | 399.14 | 11 | 73 | 190.2-194.7 | 3.49 | 0.77 ± 0.02 | 13 |
| 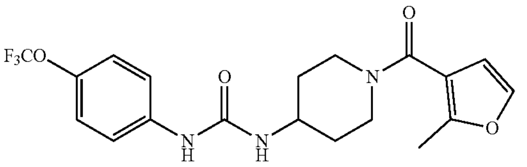 [SMILES: Cc1occc1C(=O)N1CCC(NC(=O)Nc2ccc(OC(F)(F)F)cc2)CC1] | 411.14 | 8.6 | 7.7 | 182.5-187.1 | 4.30 | 0.55 ± 0.06 | 15 |
| 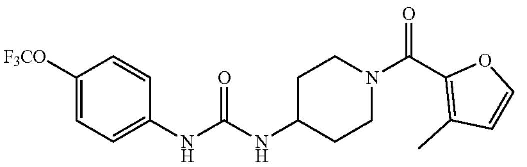 [SMILES: Cc1ccoc1C(=O)N1CCC(NC(=O)Nc2ccc(OC(F)(F)F)cc2)CC1] | 411.14 | 0.92 | 3.4 | 206.2-212.9 | 4.48 | 0.26 ± 0.11 | 21 |

TABLE 2-continued
Physical properties and human in vitro data for compounds of Fromula II and related compounds
| Structure | MW | Physical Properties<br>Sol[a] (ug/mL) | Sol[b] (ug/mL) at pH3 | mp (° C.) | Exp. LogP | Human In vitro<br>Ki (nM) | $t_{1/2}$ (min)[c] |
|---|---|---|---|---|---|---|---|
| 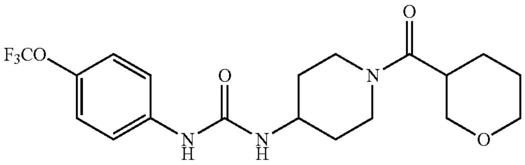 [SMILES: O=C(Nc1ccc(OC(F)(F)F)cc1)NC1CCN(C(=O)C2CCCOC2)CC1] | 415.17 | 94 | 868 | 176.2-177.7 | 3.42 | 1.99 ± 0.23 | 13 |
| 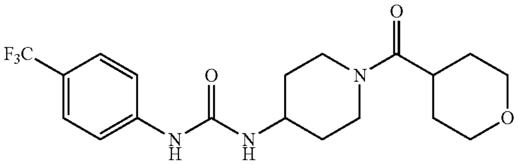 [SMILES: O=C(Nc1ccc(C(F)(F)F)cc1)NC1CCN(C(=O)C2CCOCC2)CC1] | 399.18 | 17.6 | 61 | 241.7-243.0 | 3.16 | 1.73 ± 0.01 | 11 |
| 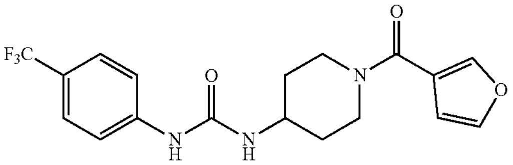 | 381.13 | 2.2 | 6 | 222.5-223.8 | 3.50 | 1.21 ± 0.2 | 11 |
| 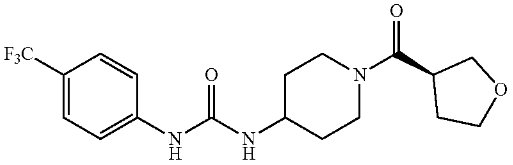 [SMILES: O=C(Nc1ccc(C(F)(F)F)cc1)NC1CCN(C(=O)[C@@H]2CCOC2)CC1] | 385.16 | 1.4 | 58 | 212.6-218.1 | 3.27 | 1.19 ± 0.08 | 13 |
| 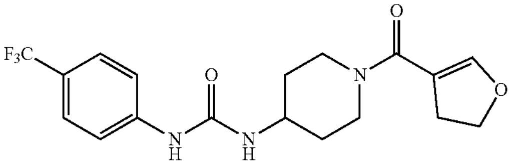 [SMILES: O=C(Nc1ccc(C(F)(F)F)cc1)NC1CCN(C(=O)C2=COCC2)CC1] | 383.15 | 2.3 | 8.2 | 243.0-243.6 | 3.37 | 1.03 ± 0.20 | 8 |
| 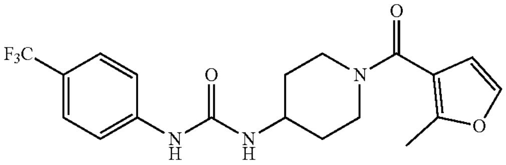 [SMILES: Cc1occc1C(=O)N1CCC(NC(=O)Nc2ccc(C(F)(F)F)cc2)CC1] | 395.15 | 0.28 | 2.1 | 237.3-238.9 | 4.19 | 0.51 ± 0.03 | 11 |
| 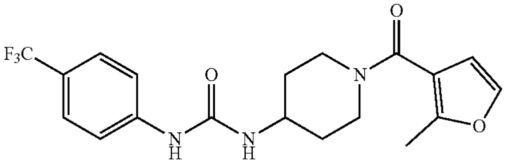 [SMILES: Cc1occc1C(=O)N1CCC(NC(=O)Nc2ccc(C(F)(F)F)cc2)CC1] | 395.15 | 0.8 | 1.8 | 224.9-228.3 | 4.29 | 0.22 ± 0.01 | 15 |
| 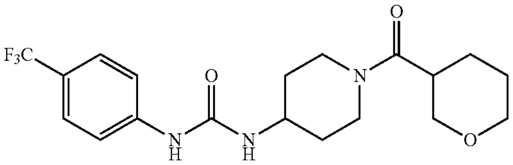 [SMILES: O=C(Nc1ccc(C(F)(F)F)cc1)NC1CCN(C(=O)C2CCCOC2)CC1] | 399.18 | 1.1 | 25 | 253.9-255.2 | 3.41 | 2.40 ± 0.08 | 11 |

TABLE 2-continued
Physical properties and human in vitro data for compounds of Fromula II and related compounds
| Structure | MW | Physical Properties: Sol[a] (ug/mL) | Physical Properties: Sol[b] (ug/mL) at pH3 | Physical Properties: mp (° C.) | Physical Properties: Exp. LogP | Human In vitro: Ki (nM) | Human In vitro: $t_{1/2}$ (min)[c] |
| --- | --- | --- | --- | --- | --- | --- | --- |
| 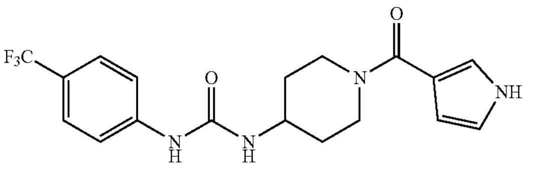 [SMILES: O=C(Nc1ccc(C(F)(F)F)cc1)NC1CCN(C(=O)c2cc[nH]c2)CC1] | 380.15 | 1.8 | 13 | 246.1-248.3 | 3.26 | 0.50 ± 0.01 | 10 |
| 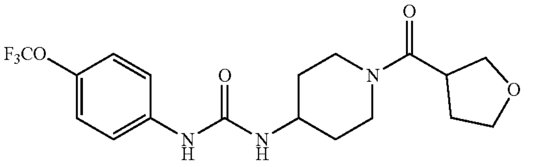 [SMILES: O=C(Nc1ccc(OC(F)(F)F)cc1)NC1CCN(C(=O)C2CCOC2)CC1] | 401.16 | 29 | 91 | 163.4-166.3 | 3.22 | 1.70 ± 0.01 | 12 |
| 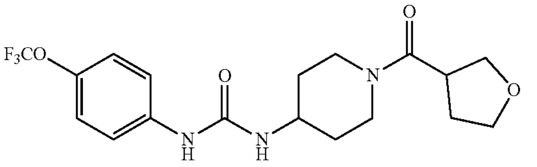 [SMILES: O=C(Nc1ccc(OC(F)(F)F)cc1)NC1CCN(C(=O)C2CCOC2)CC1] | 385.16 | 9.6 | 50 | 238.2-239.3 | 3.16 | 1.74 ± 0.11 | 10 |
| 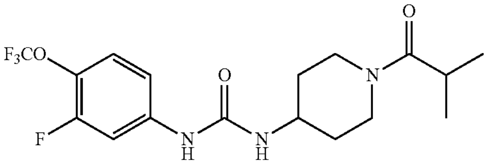 [SMILES: CC(C)C(=O)N1CCC(NC(=O)Nc2ccc(OC(F)(F)F)c(F)c2)CC1] | 391.15 | 5.3 | 5.1 | 156.9-157.6 | 4.73 | 0.31 ± 0.01 | 22 |
| 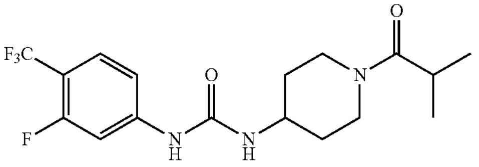 [SMILES: CC(C)C(=O)N1CCC(NC(=O)Nc2ccc(C(F)(F)F)c(F)c2)CC1] | 375.1 | 5.9 | 6 | 198.2-200.9 | 4.40 | 0.49 ± 0.4 | 12 |
| 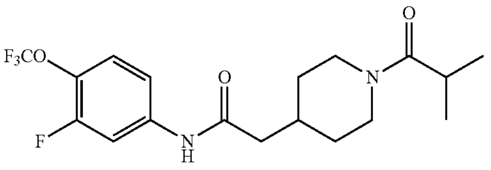 [SMILES: CC(C)C(=O)N1CCC(CC(=O)Nc2ccc(OC(F)(F)F)c(F)c2)CC1] | 390.38 | 33 | ND | 84.2-88.8 | 5.81 | 4.72 ± 0.7 | 3.4 |
| 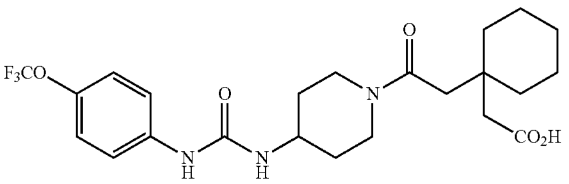 [SMILES: O=C(O)CC1(CC(=O)N2CCC(NC(=O)Nc3ccc(OC(F)(F)F)cc3)CC2)CCCCC1] | 469.22 | ND | ND | 171.8-176.7 | ND | 10.2 ± 1.1 | ND |
| 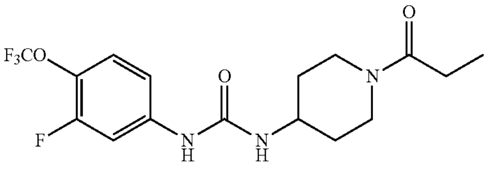 [SMILES: CCC(=O)N1CCC(NC(=O)Nc2ccc(OC(F)(F)F)c(F)c2)CC1] | 377.34 | 11 | ND | 172.6-173.1 | 4.00 | 0.87 ± 0.13 | 11 |

TABLE 2-continued
Physical properties and human in vitro data for compounds of Fromula II and related compounds
| Structure | MW | Sol[a] (ug/mL) | Sol[b] (ug/mL) at pH3 | mp (° C.) | Exp. LogP | Human In vitro Ki (nM) | Human In vitro $t_{1/2}$ (min)[c] |
|---|---|---|---|---|---|---|---|
| | | Physical Properties | | | | | |
| 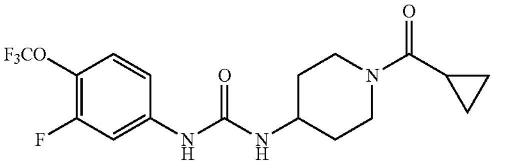 [SMILES: O=C(Nc1ccc(OC(F)(F)F)c(F)c1)NC1CCN(C(=O)C2CC2)CC1] | 389.35 | 19 | ND | 178.1-178.9 | 4.19 | 0.15 ± 0.04 | 19 |
| 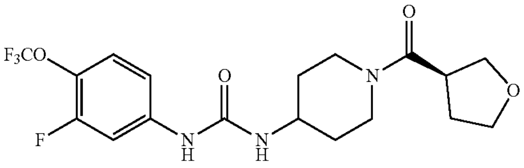 [SMILES: O=C(Nc1ccc(OC(F)(F)F)c(F)c1)NC1CCN(C(=O)[C@@H]2CCOC2)CC1] | 419.38 | 61 | 196 | 168.2-169.7 | 3.59 | 0.70 ± 0.01 | 13 |
| 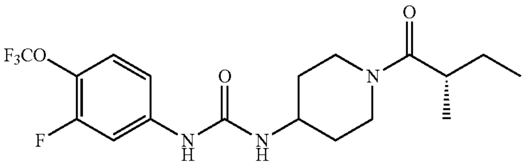 [SMILES: CC[C@H](C)C(=O)N1CCC(NC(=O)Nc2ccc(OC(F)(F)F)c(F)c2)CC1] | 405.39 | 11 | ND | 147.0-147.8 | 5.98 | <0.05 | 22 |
| 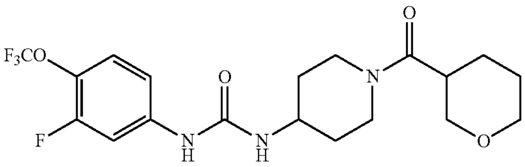 [SMILES: O=C(Nc1ccc(OC(F)(F)F)c(F)c1)NC1CCN(C(=O)C2CCCOC2)CC1] | 433.40 | 174 | 522 | 158.2-159 | 4.09 | 0.78 ± 0.19 | 12 |
| 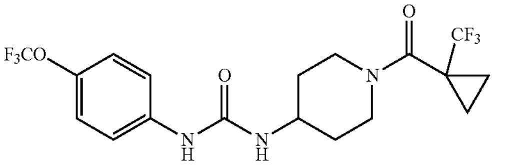 [SMILES: O=C(Nc1ccc(OC(F)(F)F)cc1)NC1CCN(C(=O)C2(C(F)(F)F)CC2)CC1] | 423.35 | 0.07 | ND | 264-266 | 4.63 | 0.05 ± 0.04 | 24 |
| 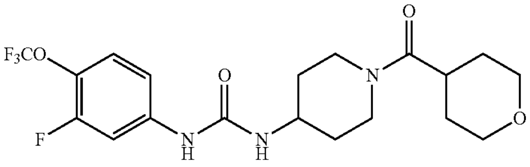 [SMILES: O=C(Nc1ccc(OC(F)(F)F)c(F)c1)NC1CCN(C(=O)C2CCOCC2)CC1] | 433.4 | 77 ± 0 | 206 ± 1 | 172.2-174.0 | 3.73 | 0.75 ± 0.05 | 11 |
| 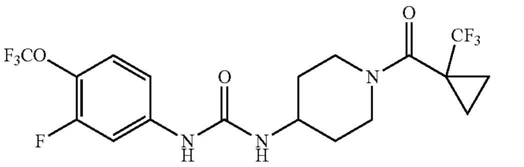 [SMILES: O=C(Nc1ccc(OC(F)(F)F)c(F)c1)NC1CCN(C(=O)C2(C(F)(F)F)CC2)CC1] | 457.35 | 92 | ND | 185.4-187 | 5.94 | <0.05 | 18 |

TABLE 2-continued
Physical properties and human in vitro data for compounds of Fromula II and related compounds
| | Physical Properties | | | | | Human In vitro | |
|---|---|---|---|---|---|---|---|
| Structure | MW | Sol[a] (ug/mL) | Sol[b] (ug/mL) at pH3 | mp (° C.) | Exp. LogP | Ki (nM) | $t_{1/2}$ (min)[c] |
| 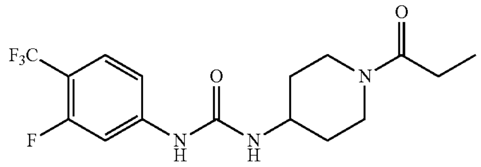 | 361.34 | 3.9 | ND | 216.2-216.8 | 3.76 | 2.94 ± 0.01 | 3.3 |
| 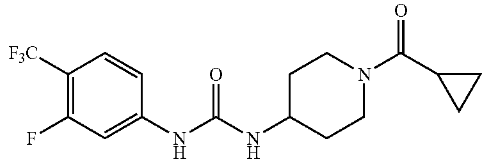 [SMILES: O=C(Nc1ccc(C(F)(F)F)c(F)c1)NC1CCN(C(=O)C2CC2)CC1] | 373.35 | 13 | ND | 181.8-182.8 | 3.94 | 0.38 ± 0.08 | 8.2 |
| 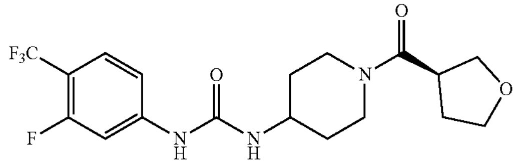 [SMILES: O=C(Nc1ccc(C(F)(F)F)c(F)c1)NC1CCN(C(=O)[C@@H]2CCOC2)CC1] | 403.38 | 1.9 | 3.1 | 227.2-229.3 | 3.41 | 2.09 ± 0.24 | 5.3 |
| 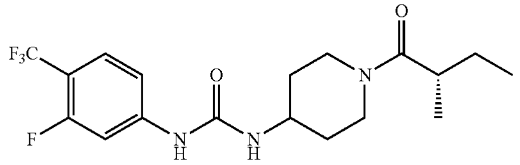 [SMILES: CC[C@H](C)C(=O)N1CCC(NC(=O)Nc2ccc(C(F)(F)F)c(F)c2)CC1] | 389.40 | 0.46 | ND | 207.4-208.3 | 5.48 | 0.37 ± 0.03 | 13 |
| 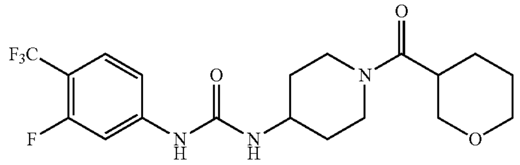 [SMILES: O=C(Nc1ccc(C(F)(F)F)c(F)c1)NC1CCN(C(=O)C2CCCOC2)CC1] | 417.40 | 11 | 40 | 236.5-238.3 | 3.84 | 2.66 ± 0.19 | 6.8 |
| 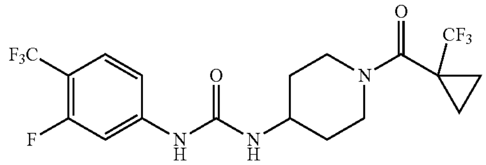 [SMILES: O=C(Nc1ccc(C(F)(F)F)c(F)c1)NC1CCN(C(=O)C2(C(F)(F)F)CC2)CC1] | 441.35 | 0.08 | ND | 240.8-241.7 | 5.52 | 0.08 ± 0.01 | 21 |
| 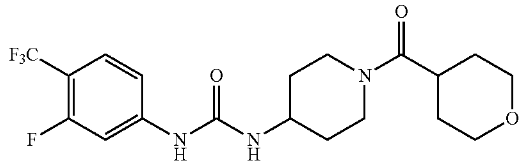 | 417.40 | 42 | 122 | 219.8-221.8 | 3.52 | 3.83 ± 0.41 | 6.9 |
| 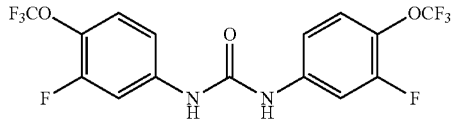 [SMILES: O=C(Nc1ccc(OC(F)(F)F)c(F)c1)Nc1ccc(OC(F)(F)F)c(F)c1] | 416.23 | ND | ND | 175.6-182.1 | ND | 1.95 ± 0.30 | ND |

TABLE 2-continued
Physical properties and human in vitro data for compounds of Fromula II and related compounds
| | | Physical Properties | | | | Human In vitro | |
|---|---|---|---|---|---|---|---|
| Structure | MW | Sol[a] (ug/mL) | Sol[b] (ug/mL) at pH3 | mp (° C.) | Exp. LogP | Ki (nM) | $t_{1/2}$ (min)[c] |
| 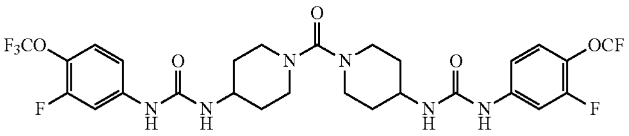 | 668.50 | ND | ND | 250.6-252.4 | ND | 10.1 ± 1.8 | ND |
| 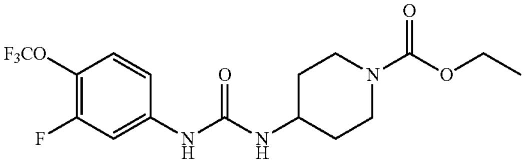 [SMILES: CCOC(=O)N1CCC(NC(=O)Nc2ccc(OC(F)(F)F)c(F)c2)CC1] | 393.34 | 0.35 | ND | 182.6-183.0 | 5.94 | <0.05 | 18 |
| 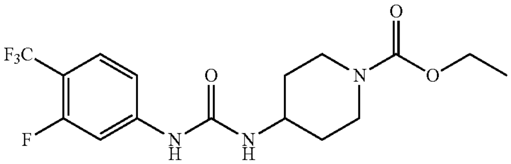 [SMILES: CCOC(=O)N1CCC(NC(=O)Nc2ccc(C(F)(F)F)c(F)c2)CC1] | 377.34 | ND | ND | 180.5-181.4 | 5.46 ± 0.02 | 0.38 ± 0.03 | 7.6 |
| 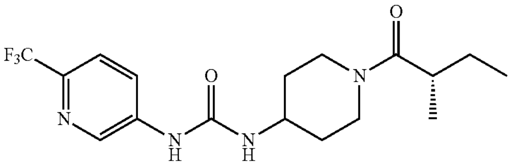 [SMILES: CC[C@H](C)C(=O)N1CCC(NC(=O)Nc2ccc(C(F)(F)F)nc2)CC1] | 372.39 | 274 | 662 | 188.5-190.0 | 3.22 | 45.0 ± 2.3 | 3.7 |
| 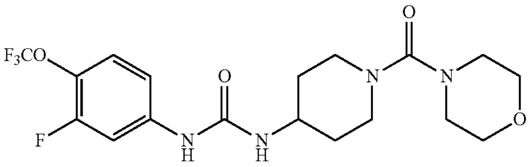 | 434.39 | 96 | 294 | 160.5-162.6 | 3.93 | 0.70 ± 0.06 | 15 |
| 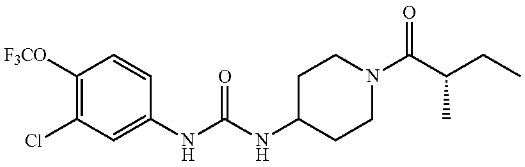 [SMILES: CC[C@H](C)C(=O)N1CCC(NC(=O)Nc2ccc(OC(F)(F)F)c(Cl)c2)CC1] | 421.85 | 0.79 | ND | 183.9-184.5 | 7.70 | 3.35 ± 0.42 | 10 |
| 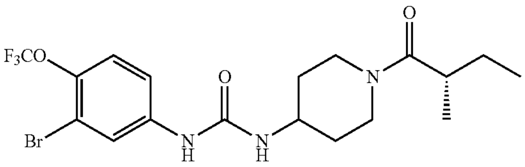 [SMILES: CC[C@H](C)C(=O)N1CCC(NC(=O)Nc2ccc(OC(F)(F)F)c(Br)c2)CC1] | 465.29 | 0.58 | ND | 197.6-198.5 | 8.07 | 3.40 ± 1.38 | 9.3 |
| 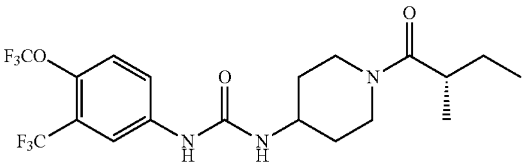 [SMILES: CC[C@H](C)C(=O)N1CCC(NC(=O)Nc2ccc(OC(F)(F)F)c(C(F)(F)F)c2)CC1] | 455.40 | 0.05 | ND | 201.1-202.1 | 9.02 | 9.91 ± 3.37 | 5.9 |

TABLE 2-continued

Physical properties and human in vitro data for compounds of Fromula II and related compounds

| Structure | Physical Properties MW | Sol[a] (ug/mL) | Sol[b] (ug/mL) at pH3 | mp (° C.) | Exp. LogP | Human In vitro Ki (nM) | $t_{1/2}$ (min)[c] |
|---|---|---|---|---|---|---|---|
| 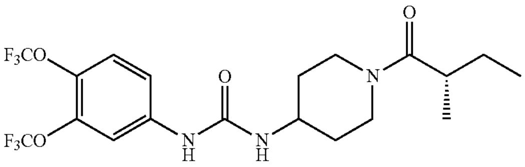 [SMILES: CC[C@H](C)C(=O)N1CCC(NC(=O)Nc2ccc(OC(F)(F)F)c(OC(F)(F)F)c2)CC1] | 471.40 | 5.5 | ND | 170.8-172.4 | 10.62 | 9.07 ± 0.36 | 11 |
| 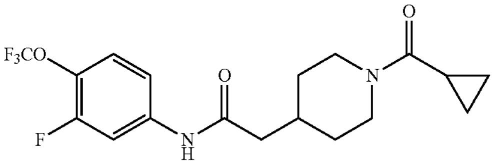 [SMILES: O=C(CC1CCN(C(=O)C2CC2)CC1)Nc1ccc(OC(F)(F)F)c(F)c1] | 388.36 | 715 | ND | 152.3-153.2 | 5.11 | 6.60 ± 0.01 | 3.3 |
| 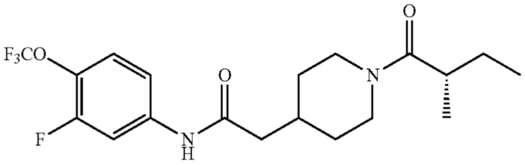 [SMILES: CC[C@H](C)C(=O)N1CCC(CC(=O)Nc2ccc(OC(F)(F)F)c(F)c2)CC1] | 404.41 | 21 | ND | gel | 7.68 | 3.14 ± 0.70 | 4.5 |
| 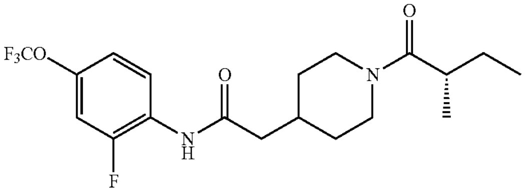 [SMILES: CC[C@H](C)C(=O)N1CCC(CC(=O)Nc2ccc(OC(F)(F)F)cc2F)CC1] | 388.41 | 2.6 | ND | 225.1 | 6.00 | 4.72 | 4.7 |

[a]The solubility of the drugs were measured at Sodium Phosphate Buffer at pH 7.4

[b]The solubility of the drugs were measured at Ammonium AcetateBuffer at pH 3.0

[c]$t_{1/2}$ defined as the time required for half of the drug being dissociated from the enzyme based on the fluorescence signals.

TABLE 3

Mouse and Rat PK parameters in vitro data for compounds of Fromula II and related compounds

| Structure | Mouse[d] PK parameters AUC (nM*h) | Cmax (nM) | $T_{1/2}$ (h) | $T_{max}$ (h) | Rat[e] PK parameters AUC (nM*h) | $T_{1/2}$ (h) | $T_{max}$ (h) | $C_{max}$ (nM) |
|---|---|---|---|---|---|---|---|---|
| 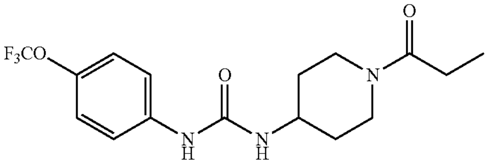 [SMILES: CCC(=O)N1CCC(NC(=O)Nc2ccc(OC(F)(F)F)cc2)CC1] | 10650 | 495 | 12.1 | 8 | 1080 ± 89 | 6.0 ± 0.7 | 2.3 ± 0.4 | 133 ± 4 |
| 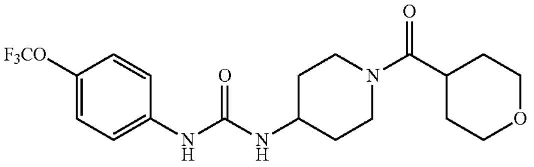 [SMILES: O=C(Nc1ccc(OC(F)(F)F)cc1)NC1CCN(C(=O)C2CCOCC2)CC1] | 5062 | 460 | 2.8 | 4.1 | 234 ± 19 | 3.7 ± 0.6 | 4.4 ± 0.2 | 23 ± 1 |

TABLE 3-continued
Mouse and Rat PK parameters in vitro data for compounds of Fromula II and related compounds
| Structure | Mouse[d] PK parameters AUC (nM*h) | Cmax (nM) | $T_{1/2}$ (h) | $T_{max}$ (h) | Rat[e] PK parameters AUC (nM*h) | $T_{1/2}$ (h) | $T_{max}$ (h) | $C_{max}$ (nM) |
|---|---|---|---|---|---|---|---|---|
| 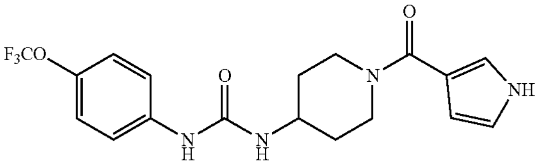 [SMILES: O=C(Nc1ccc(OC(F)(F)F)cc1)NC1CCN(C(=O)c2cc[nH]c2)CC1] | ND | ND | ND | ND | ND | ND | ND | ND |
| 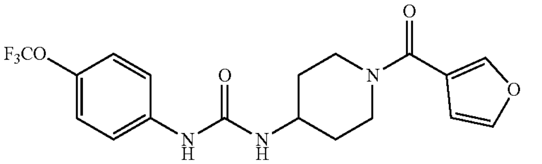 [SMILES: O=C(Nc1ccc(OC(F)(F)F)cc1)NC1CCN(C(=O)c2ccoc2)CC1] | 2927 | 146 | 5.1 | 7.3 | ND | ND | ND | ND |
| 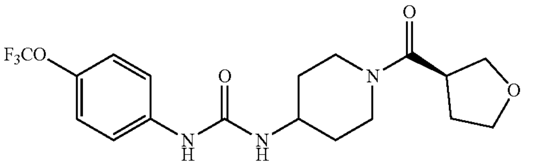 [SMILES: O=C(Nc1ccc(OC(F)(F)F)cc1)NC1CCN(C(=O)[C@@H]2CCOC2)CC1] | 656 | 50 | 3.4 | 6.2 | ND | ND | ND | ND |
| 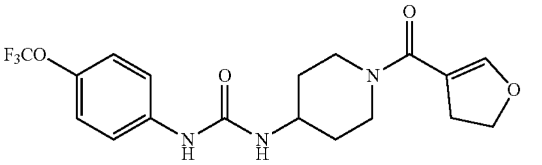 [SMILES: O=C(Nc1ccc(OC(F)(F)F)cc1)NC1CCN(C(=O)C2=COCC2)CC1] | 670 | 58 | 2.9 | 4.2 | ND | ND | ND | ND |
| 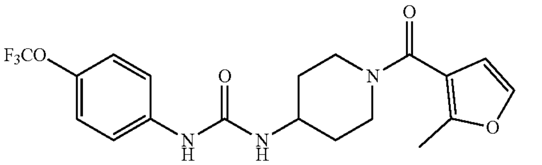 [SMILES: Cc1occc1C(=O)N1CCC(NC(=O)Nc2ccc(OC(F)(F)F)cc2)CC1] | 9986 | 409 | 6.2 | 9 | 1080 ± 89 | 6.0 ± 0.7 | 2.3 ± 0.4 | 133 ± 4 |
| 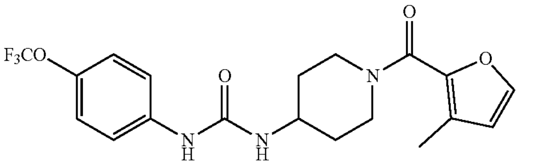 [SMILES: Cc1ccoc1C(=O)N1CCC(NC(=O)Nc2ccc(OC(F)(F)F)cc2)CC1] | 4562 | 294 | 3.9 | 5.7 | ND | ND | ND | ND |
| 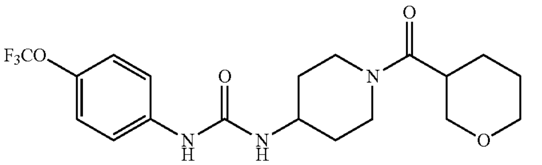 [SMILES: O=C(Nc1ccc(OC(F)(F)F)cc1)NC1CCN(C(=O)C2CCCOC2)CC1] | 634 | 31 | 5.3 | 7.6 | ND | ND | ND | ND |
| 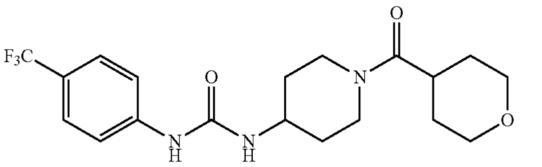 [SMILES: O=C(Nc1ccc(C(F)(F)F)cc1)NC1CCN(C(=O)C2CCOCC2)CC1] | 5265 | 376 | 3.6 | 5.2 | 391 ± 31 | 3.0 ± 0.4 | 2.5 ± 0.2 | 54 ± 3 |

TABLE 3-continued
Mouse and Rat PK parameters in vitro data for compounds of Fromula II and related compounds
| Structure | Mouse[d] PK parameters | | | | Rat[e] PK parameters | | | |
|---|---|---|---|---|---|---|---|---|
| | AUC (nM*h) | Cmax (nM) | $T_{1/2}$ (h) | $T_{max}$ (h) | AUC (nM*h) | $T_{1/2}$ (h) | $T_{max}$ (h) | $C_{max}$ (nM) |
| 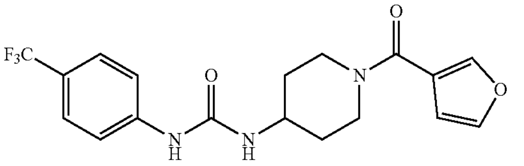 [SMILES: O=C(Nc1ccc(C(F)(F)F)cc1)NC1CCN(C(=O)c2ccoc2)CC1] | 794 | 28 | 4.2 | 7.3 | 3549 ± 271 | 4.4 ± 0.4 | 3.4 ± 0.3 | 308 ± 16 |
| 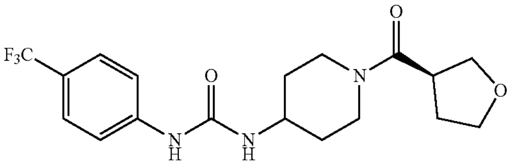 [SMILES: O=C(Nc1ccc(C(F)(F)F)cc1)NC1CCN(C(=O)[C@@H]2CCOC2)CC1] | 729 | 154 | 1.2 | 1.7 | ND | ND | ND | ND |
| 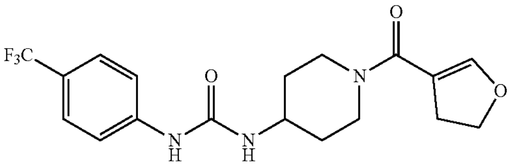 [SMILES: O=C(Nc1ccc(C(F)(F)F)cc1)NC1CCN(C(=O)C2=COCC2)CC1] | 875 | 78 | 2.8 | 4.1 | ND | ND | ND | ND |
| 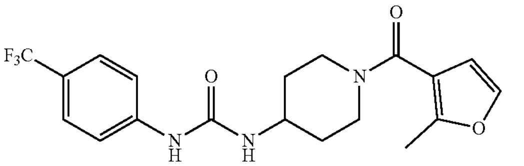 [SMILES: Cc1occc1C(=O)N1CCC(NC(=O)Nc2ccc(C(F)(F)F)cc2)CC1] | 6880 | 433 | 4.0 | 5.8 | ND | ND | ND | ND |
| 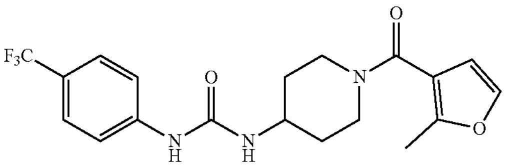 [SMILES: Cc1occc1C(=O)N1CCC(NC(=O)Nc2ccc(C(F)(F)F)cc2)CC1] | 1037 | 116 | 2.3 | 3.3 | ND | ND | ND | ND |
| 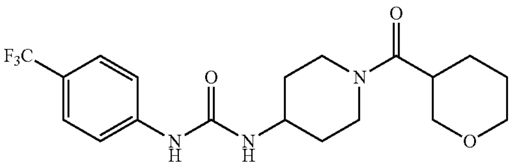 [SMILES: O=C(Nc1ccc(C(F)(F)F)cc1)NC1CCN(C(=O)C2CCCOC2)CC1] | 3171 | 199 | 4.1 | 5.9 | ND | ND | ND | ND |
| 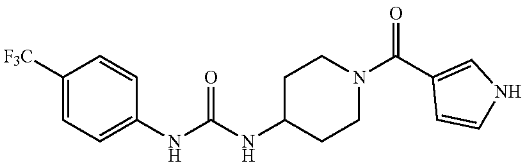 [SMILES: O=C(Nc1ccc(C(F)(F)F)cc1)NC1CCN(C(=O)c2cc[nH]c2)CC1] | 83 | 11 | 2 | 2.8 | ND | ND | ND | ND |
| 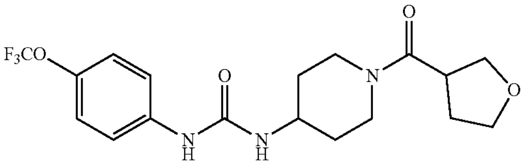 [SMILES: O=C(Nc1ccc(OC(F)(F)F)cc1)NC1CCN(C(=O)C2CCOC2)CC1] | 12612 | 703 | 4.6 | 6.6 | ND | ND | ND | ND |

TABLE 3-continued
Mouse and Rat PK parameters in vitro data for compounds of Fromula II and related compounds
| Structure | Mouse[d] PK parameters | | | | Rat[e] PK parameters | | | |
| --- | --- | --- | --- | --- | --- | --- | --- | --- |
| | AUC (nM*h) | Cmax (nM) | $T_{1/2}$ (h) | $T_{max}$ (h) | AUC (nM*h) | $T_{1/2}$ (h) | $T_{max}$ (h) | $C_{max}$ (nM) |
| 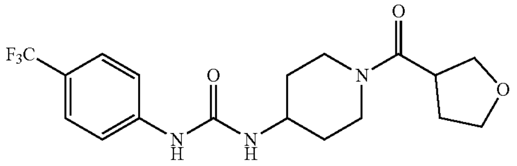 [SMILES: O=C(Nc1ccc(C(F)(F)F)cc1)NC1CCN(C(=O)C2CCOC2)CC1] | 4732 | 342 | 6.9 | 6.8 | ND | ND | ND | ND |
| 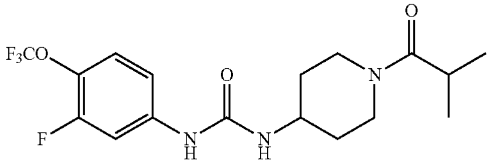 [SMILES: CC(C)C(=O)N1CCC(NC(=O)Nc2ccc(OC(F)(F)F)c(F)c2)CC1] | 4775 | 162 | 4.8 | 5.9 | 637 ± 85 | 2.7 ± 0.4 | 2.8 ± 0.3 | 84 ± 5 |
| 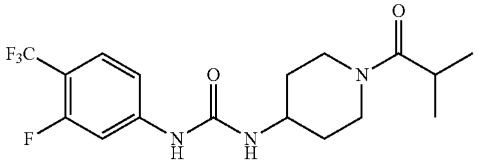 [SMILES: CC(C)C(=O)N1CCC(NC(=O)Nc2ccc(C(F)(F)F)c(F)c2)CC1] | 9654 | 518 | 6.2 | 7.9 | 212 ± 22 | 2.4 ± 0.3 | 1.8 ± 0.2 | 38 ± 3 |
| 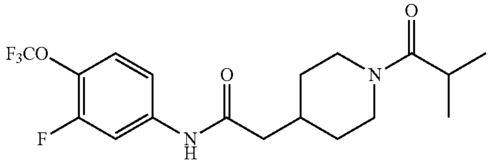 [SMILES: CC(C)C(=O)N1CCC(CC(=O)Nc2ccc(OC(F)(F)F)c(F)c2)CC1] | ND | ND | ND | ND | 66 ± 11 | 1.2 ± 0.2 | 1.6 ± 0.1 | 17 ± 2 |
| 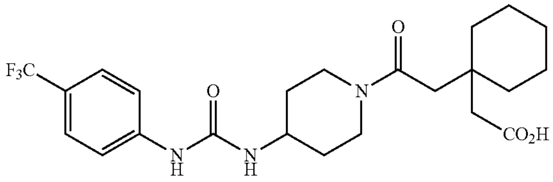 [SMILES: O=C(O)CC1(CC(=O)N2CCC(NC(=O)Nc3ccc(C(F)(F)F)cc3)CC2)CCCCC1] | 11608 | 590 | 5 | 7.4 | ND | ND | ND | ND |
| 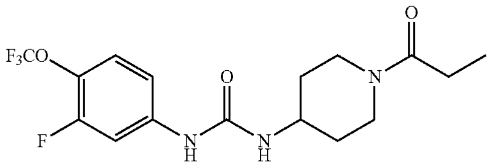 [SMILES: CCC(=O)N1CCC(NC(=O)Nc2ccc(OC(F)(F)F)c(F)c2)CC1] | 20587 | 978 | 5.4 | 8.0 | 2701 ± 357 | 4.2 ± 0.8 | 4.5 ± 0.5 | 196 ± 12 |
| 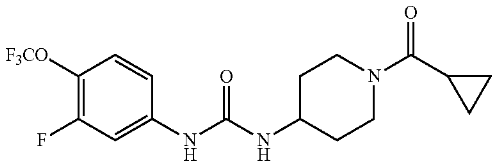 [SMILES: O=C(Nc1ccc(OC(F)(F)F)c(F)c1)NC1CCN(C(=O)C2CC2)CC1] | 5589 | 282 | 5.1 | 7.6 | 1027 ± 65 | 2.9 ± 0.3 | 4.0 ± 0.1 | 95 ± 3 |
| 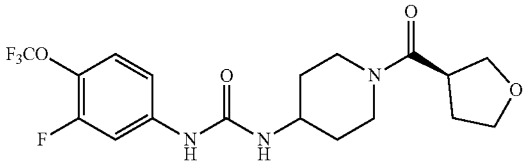 [SMILES: O=C(Nc1ccc(OC(F)(F)F)c(F)c1)NC1CCN(C(=O)[C@@H]2CCOC2)CC1] | 97.3 ± 0.1 | 2549 | 174 | 3.7 | 869 ± 127 | 3.8 ± 0.6 | 2.9 ± 0.3 | 84 ± 6 |

TABLE 3-continued
Mouse and Rat PK parameters in vitro data for compounds of Fromula II and related compounds
| Structure | Mouse[d] PK parameters | | | | Rat[e] PK parameters | | | |
|---|---|---|---|---|---|---|---|---|
| | AUC (nM*h) | Cmax (nM) | $T_{1/2}$ (h) | $T_{max}$ (h) | AUC (nM*h) | $T_{1/2}$ (h) | $T_{max}$ (h) | $C_{max}$ (nM) |
| 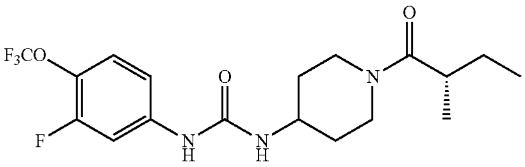 [SMILES: CC[C@H](C)C(=O)N1CCC(NC(=O)Nc2ccc(OC(F)(F)F)c(F)c2)CC1] | 99.8 ± 0.1 | 737 | 117 | 1.6 | 208 ± 25 | 1.6 ± 0.2 | 1.8 ± 0.1 | 42 ± 6 |
| 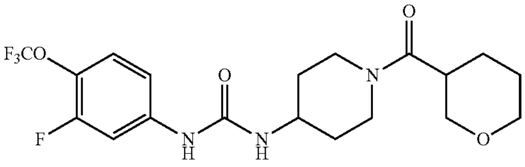 [SMILES: O=C(Nc1ccc(OC(F)(F)F)c(F)c1)NC1CCN(C(=O)C2CCCOC2)CC1] | 99.4 ± 0.1 | 24691 | 1046 | 6 | 328 ± 18 | 3.7 ± 0.5 | 2.6 ± 0.2 | 43 ± 3 |
| 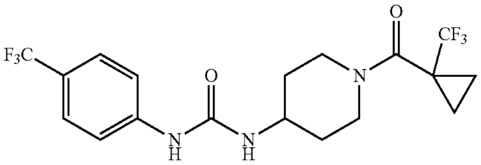 [SMILES: O=C(Nc1ccc(C(F)(F)F)cc1)NC1CCN(C(=O)C2(C(F)(F)F)CC2)CC1] | ND | 6488 | 356 | 4.7 | ND | ND | ND | ND |
| 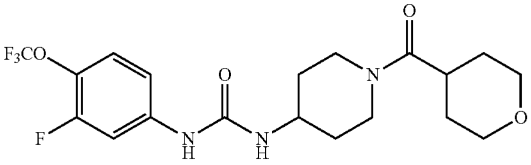 [SMILES: O=C(Nc1ccc(OC(F)(F)F)c(F)c1)NC1CCN(C(=O)C2CCOCC2)CC1] | 98.5 ± 0.1 | ND | ND | ND | 1236 ± 63 | 6.2 ± 0.4 | 3.1 ± 0.2 | 103 ± 8 |
| 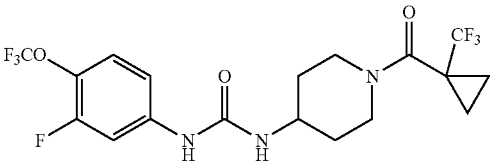 [SMILES: O=C(Nc1ccc(OC(F)(F)F)c(F)c1)NC1CCN(C(=O)C2(C(F)(F)F)CC2)CC1] | 99.7 ± 0.1 | ND | ND | ND | 486 ± 87 | 2.9 ± 0.3 | 4.3 ± 0.4 | 41 ± 3 |
| 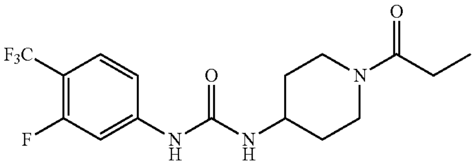 [SMILES: CCC(=O)N1CCC(NC(=O)Nc2ccc(C(F)(F)F)c(F)c2)CC1] | ND | ND | ND | ND | ND | ND | ND | ND |
| 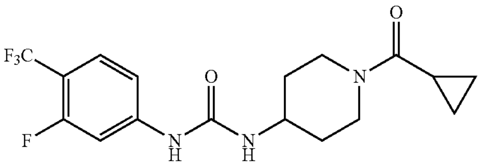 [SMILES: O=C(Nc1ccc(C(F)(F)F)c(F)c1)NC1CCN(C(=O)C2CC2)CC1] | ND | ND | ND | ND | ND | ND | ND | ND |
| 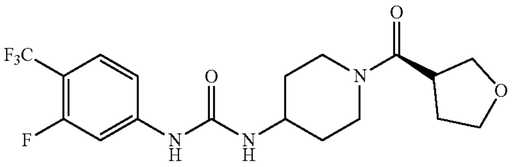 | ND | ND | ND | ND | ND | ND | ND | ND |

TABLE 3-continued

Mouse and Rat PK parameters in vitro data for compounds of Fromula II and related compounds

| Structure | Mouse[d] PK parameters AUC (nM*h) | Cmax (nM) | $T_{1/2}$ (h) | $T_{max}$ (h) | Rat[e] PK parameters AUC (nM*h) | $T_{1/2}$ (h) | $T_{max}$ (h) | $C_{max}$ (nM) |
|---|---|---|---|---|---|---|---|---|
| 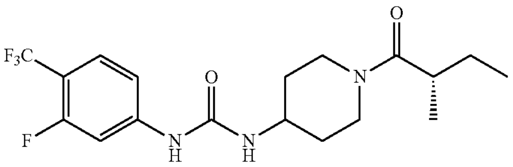 [SMILES: CC[C@H](C)C(=O)N1CCC(NC(=O)Nc2ccc(C(F)(F)F)c(F)c2)CC1] | ND | ND | ND | ND | ND | ND | ND | ND |
| 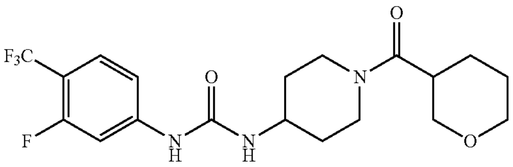 [SMILES: O=C(Nc1ccc(C(F)(F)F)c(F)c1)NC1CCN(C(=O)C2CCCOC2)CC1] | ND | ND | ND | ND | ND | ND | ND | ND |
| 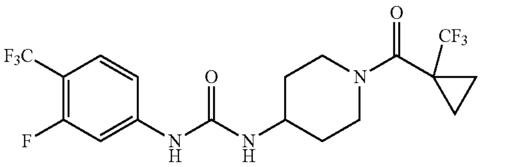 [SMILES: O=C(Nc1ccc(C(F)(F)F)c(F)c1)NC1CCN(C(=O)C2(C(F)(F)F)CC2)CC1] | ND | ND | ND | ND | ND | ND | ND | ND |
| 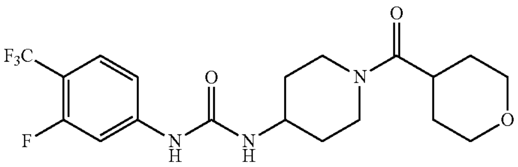 [SMILES: O=C(Nc1ccc(C(F)(F)F)c(F)c1)NC1CCN(C(=O)C2CCOCC2)CC1] | 98.8 ± 0.2 | ND | ND | ND | 1653 ± 42 | 4.5 ± 0.4 | 4.0 ± 0.4 | 139 ± 9 |
| 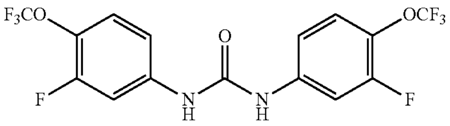 [SMILES: O=C(Nc1ccc(OC(F)(F)F)c(F)c1)Nc1ccc(OC(F)(F)F)c(F)c1] | ND | ND | ND | ND | ND | ND | ND | ND |
| 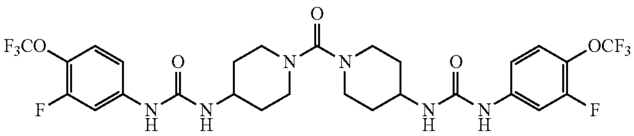 [SMILES: O=C(Nc1ccc(OC(F)(F)F)c(F)c1)NC1CCN(C(=O)N2CCC(NC(=O)Nc3ccc(OC(F)(F)F)c(F)c3)CC2)CC1] | ND | ND | ND | ND | ND | ND | ND | ND |
| 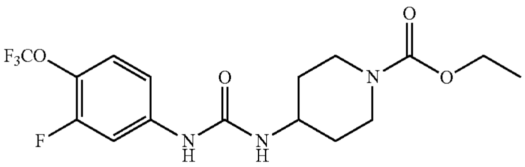 [SMILES: CCOC(=O)N1CCC(NC(=O)Nc2ccc(OC(F)(F)F)c(F)c2)CC1] | ≥99.9 | ND | ND | ND | 1335 ± 93 | 4.7 ± 0.8 | 3.7 ± 0.5 | 105 ± 16 |
| 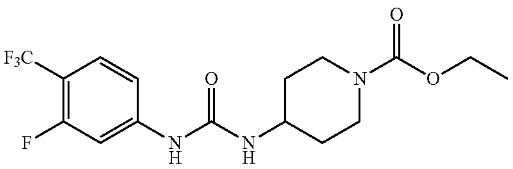 [SMILES: CCOC(=O)N1CCC(NC(=O)Nc2ccc(C(F)(F)F)c(F)c2)CC1] | ND | ND | ND | ND | ND | ND | ND | ND |

TABLE 3-continued
Mouse and Rat PK parameters in vitro data for compounds of Fromula II and related compounds
| Structure | Mouse[d] PK parameters | | | | Rat[e] PK parameters | | | |
|---|---|---|---|---|---|---|---|---|
| | AUC (nM*h) | Cmax (nM) | $T_{1/2}$ (h) | $T_{max}$ (h) | AUC (nM*h) | $T_{1/2}$ (h) | $T_{max}$ (h) | $C_{max}$ (nM) |
| 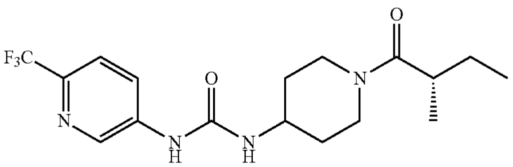 [SMILES: CC[C@H](C)C(=O)N1CCC(NC(=O)Nc2ccc(C(F)(F)F)nc2)CC1] | ND | ND | ND | ND | ND | ND | ND | ND |
| 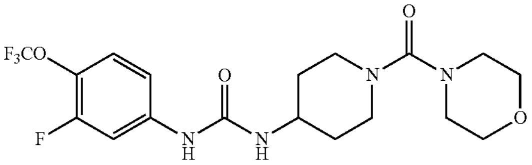 [SMILES: O=C(Nc1ccc(OC(F)(F)F)c(F)c1)NC1CCN(C(=O)N2CCOCC2)CC1] | 98.2 ± 0.1 | ND | ND | ND | 327 ± 32 | 3.6 ± 0.6 | 2.9 ± 0.3 | 40 ± 2 |
| 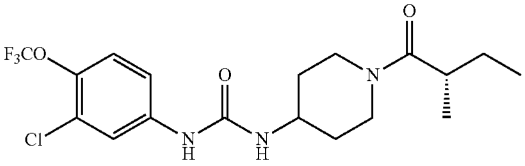 | ≥99.9 | ND | ND | ND | 241 ± 12 | 2.9 ± 0.5 | 2.1 ± 0.3 | 42 ± 6 |
| 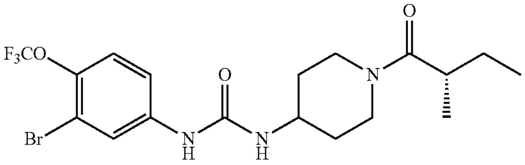 [SMILES: CC[C@H](C)C(=O)N1CCC(NC(=O)Nc2ccc(OC(F)(F)F)c(Br)c2)CC1] | ND | ND | ND | ND | ND | ND | ND | ND |
| 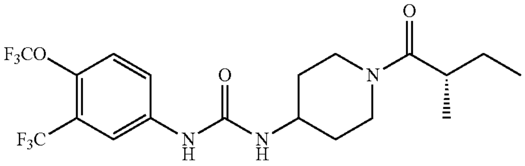 | ND | ND | ND | ND | ND | ND | ND | ND |
| 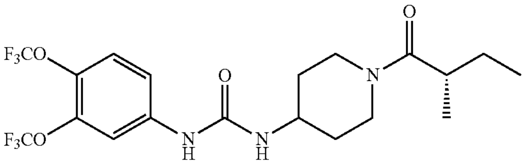 | ≥99.9 | ND | ND | ND | 75 ± 6 | 2.3 ± 0.4 | 2.5 ± 0.2 | 11 ± 1 |
| 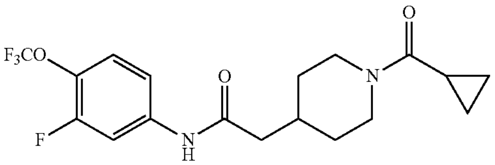 [SMILES: O=C(CC1CCN(C(=O)C2CC2)CC1)Nc1ccc(OC(F)(F)F)c(F)c1] | ND | ND | ND | ND | ND | ND | ND | ND |
| 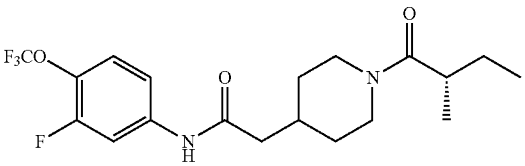 [SMILES: CC[C@H](C)C(=O)N1CCC(CC(=O)Nc2ccc(OC(F)(F)F)c(F)c2)CC1] | 99.5 ± 0.1 | ND | ND | ND | 16 ± 1 | 0.9 ± 0.1 | 1.4 ± 0.1 | 3.6 ± 0.6 |

TABLE 3-continued

Mouse and Rat PK parameters in vitro data for compounds of Fromula II and related compounds

| Structure | Mouse[d] PK parameters AUC (nM*h) | Cmax (nM) | $T_{1/2}$ (h) | $T_{max}$ (h) | Rat[e] PK parameters AUC (nM*h) | $T_{1/2}$ (h) | $T_{max}$ (h) | $C_{max}$ (nM) |
|---|---|---|---|---|---|---|---|---|
| 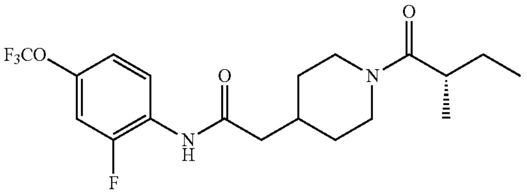 [SMILES: CC[C@H](C)C(=O)N1CCC(CC(=O)Nc2ccc(OC(F)(F)F)cc2F)CC1] | ND | ND | ND | ND | ND | ND | ND | ND |

[d]Mice were treated by oral gavage at single dose (0.3 mg/kg) which drugs were formulated with 20% (v/v) PEG400 in oleic acid-rich triglyceride. The results were at average of 4 mice. The mice PK parameters were calculated by Winnonlin ® based on the best fit model of one compartmental analysis.
[e]Rat were treated by oral gavage at single dose (0.1 mg/kg) which drugs were formulated with PEG 300. The results were at average of 4 rats. The PK parameters were calculated by Winnonlin ® based on the best fit model of one compartmental analysis.

The compounds of Formula II may exist as salts. The present invention includes such salts. Typically, the salts used are pharmaceutically acceptable salts.

Pharmaceutically acceptable salts include salts of the active compounds which are prepared with relatively non-toxic acids or bases, depending on the particular substituents found on the compounds described herein. When compounds of Formula II contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of Formula II contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of Formula II contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of Formula II can exist in unsolvated forms as well as solvated forms, including hydrated forms. In general, the solvated forms are equivalent to unsolvated forms and are encompassed within the scope of the present invention. Certain compounds of Formula II may exist in multiple crystalline or amorphous forms. In general, all physical forms are equivalent for the uses contemplated by the present invention and are intended to be within the scope of the present invention.

Certain compounds of Formula II possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of Formula II do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer includes one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of Formula II may also contain unnatural proportions of atomic isotopes at one or more of the atoms that constitute such compounds. For example, the compounds of Formula II may be radiolabeled with radioactive isotopes, such as for example deuterium ($^{2}H$), tritium ($^{3}H$), iodine-125 ($^{125}I$), carbon-13 ($^{13}C$), or carbon-14 ($^{14}C$). All isotopic variations of the compounds of Formula II, whether radioactive or not, are encompassed within the scope of the present invention.

In addition to salt forms, the compounds of Formula II can be prepared as prodrugs. Prodrugs of the compounds described herein are those compounds that readily undergo chemical changes under physiological conditions to provide the compounds of Formula II. Additionally, prodrugs can be converted to the compounds of Formula II by chemical or biochemical methods in an ex vivo environment. For example, prodrugs can be slowly converted to the compounds of Formula II when placed in a transdermal patch reservoir with a suitable enzyme or chemical reagent.

The compounds of Formula II can be made by a variety of methods known in the art.

b. Compounds of Formula I

Compounds of Formula I are characterized by the formula (I)

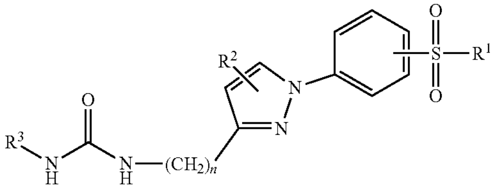

wherein $R^1$ is selected from the group consisting of $C_{1-6}$ alkyl, $—NR^{1a}R^{1b}$ and $C_{3-6}$ cycloalkyl;

$R^{1a}$ and $R^{1b}$ are each independently selected from the group consisting of H and $C_{1-6}$ alkyl;

$R^2$ is selected from the group consisting of $C_{1-6}$ alkyl, $C_{3-6}$ cycloalkyl and aryl, wherein the cycloalkyl and aryl are each optionally substituted with $C_{1-6}$ alkyl;

$R^3$ is selected from the group consisting of $C_{5-10}$ cycloalkyl and aryl, each optionally substituted with from 1 to 3 $R^{3a}$ groups wherein each $R^{3a}$ is independently selected from the group consisting of $C_{1-6}$ alkyl, $C_{1-6}$ alkoxy, halogen, $C_{1-6}$ haloalkyl and $C_{1-6}$ haloalkoxy;

subscript n is an integer from 0 to 6;

and salts and isomers thereof.

In some embodiments, the compound of Formula I is represented by Formula Ia:

(Ia)

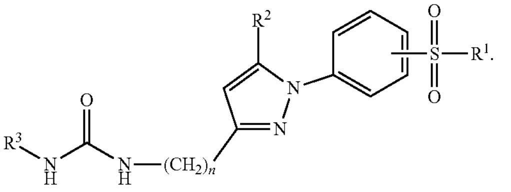

In some embodiments, the compound of Formula I is represented by Formula Ib:

(Ib)

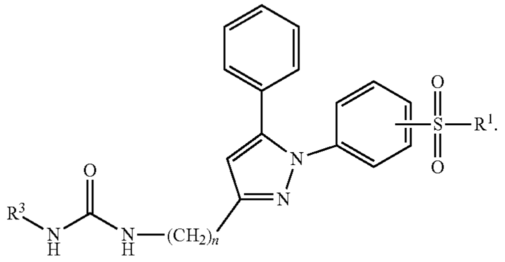

In some embodiments, the compound of Formula I is represented by Formula Ic:

(Ic)

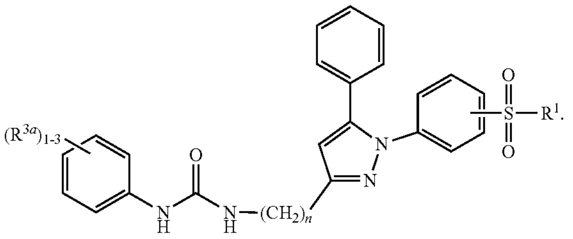

In some embodiments, the present invention provides a compound of Formula I, wherein $R^1$ is $C_{1-6}$ alkyl or $—NR^{1a}R^{1b}$; $R^{1a}$ and $R^{1b}$ are each independently H or $C_{1-6}$ alkyl; $R^2$ is aryl, optionally substituted with $C_{1-6}$ alkyl; and $R^3$ is cycloalkyl or aryl, each optionally substituted with from 1 to 3 $R^{3a}$ groups wherein each $R^{3a}$ is independently $C_{1-6}$ alkyl, halogen, $C_{1-6}$ haloalkyl and $C_{1-6}$ haloalkoxy. In some other embodiments, $R^1$ is methyl, ethyl, propyl, $—NH_2$ and $—NMe_2$; $R^2$ is phenyl, optionally substituted with a member selected from methyl, ethyl or propyl; and $R^3$ is selected from cyclohexyl, cycloheptyl, cyclooctyl, adamantyl or phenyl, wherein the phenyl is optionally substituted with from 1 to 3 $R^{3a}$ groups wherein each $R^{3a}$ is independently methyl, ethyl, propyl, Cl, Br, T, $—CF_3$ or $—OCF_3$.

In some other embodiments, the present invention provides a compound of Formula I, selected from those in Table 4

TABLE 4

| Compounds of Formula I<br>Structure | |
|---|---|
| 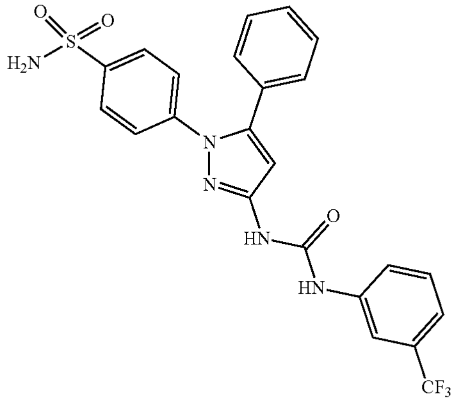 [SMILES: NS(=O)(=O)c1ccc(-n2nc(NC(=O)Nc3cccc(C(F)(F)F)c3)cc2-c2ccccc2)cc1] | 2.001 |

TABLE 4-continued
| Compounds of Formula I Structure | |
|---|---|
| 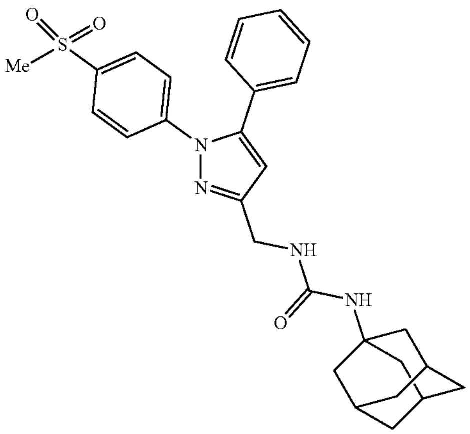 [SMILES: CS(=O)(=O)c1ccc(-n2nc(CNC(=O)NC34CC5CC(CC(C5)C3)C4)cc2-c2ccccc2)cc1] | 2.002 |
| 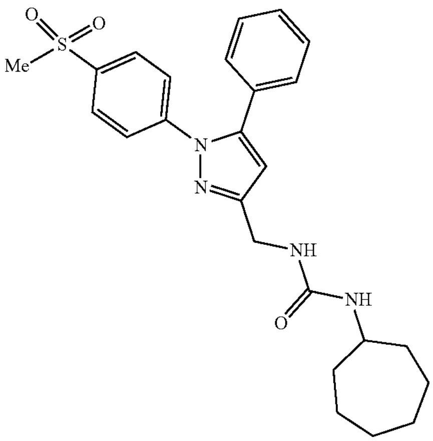 [SMILES: CS(=O)(=O)c1ccc(-n2nc(CNC(=O)NC3CCCCCC3)cc2-c2ccccc2)cc1] | 2.003 |
| 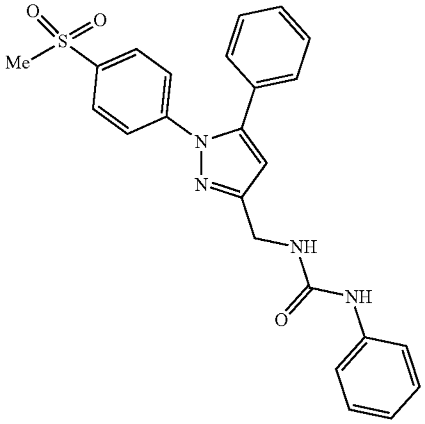 [SMILES: CS(=O)(=O)c1ccc(-n2nc(CNC(=O)Nc3ccccc3)cc2-c2ccccc2)cc1] | 2.004 |
TABLE 4-continued
| Compounds of Formula I Structure | |
|---|---|
| 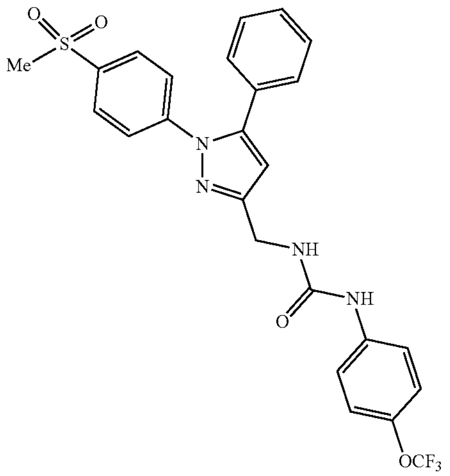 [SMILES: CS(=O)(=O)c1ccc(-n2nc(CNC(=O)Nc3ccc(OC(F)(F)F)cc3)cc2-c2ccccc2)cc1] | 2.005 |
| 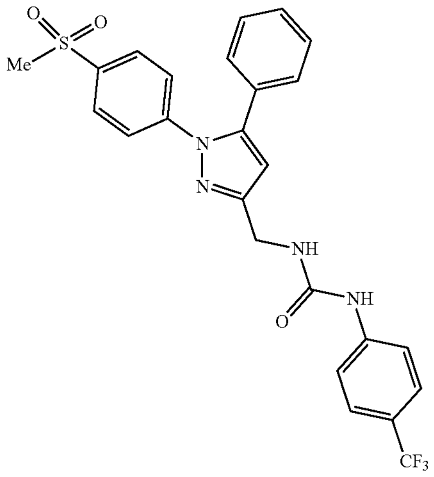 [SMILES: CS(=O)(=O)c1ccc(-n2nc(CNC(=O)Nc3ccc(C(F)(F)F)cc3)cc2-c2ccccc2)cc1] | 2.006 |
| 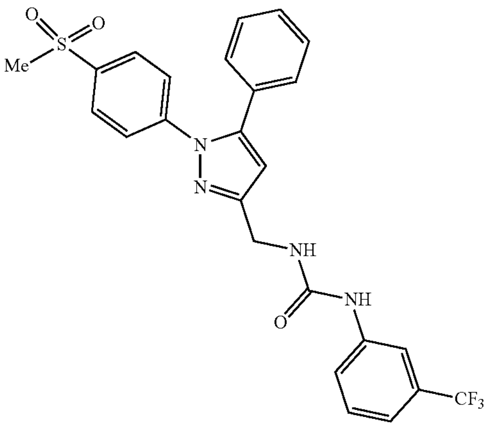 [SMILES: CS(=O)(=O)c1ccc(-n2nc(CNC(=O)Nc3cccc(C(F)(F)F)c3)cc2-c2ccccc2)cc1] | 2.007 |

TABLE 4-continued
| Compounds of Formula I Structure | |
|---|---|
| 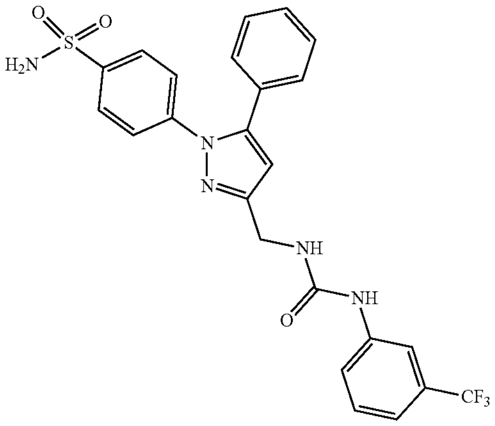 [SMILES: NS(=O)(=O)c1ccc(-n2nc(CNC(=O)Nc3cccc(C(F)(F)F)c3)cc2-c2ccccc2)cc1] | 2.008 |
| 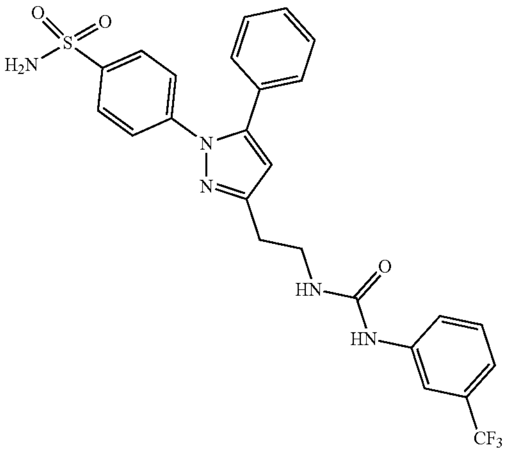 [SMILES: NS(=O)(=O)c1ccc(-n2nc(CCNC(=O)Nc3cccc(C(F)(F)F)c3)cc2-c2ccccc2)cc1] | 2.009 |
| 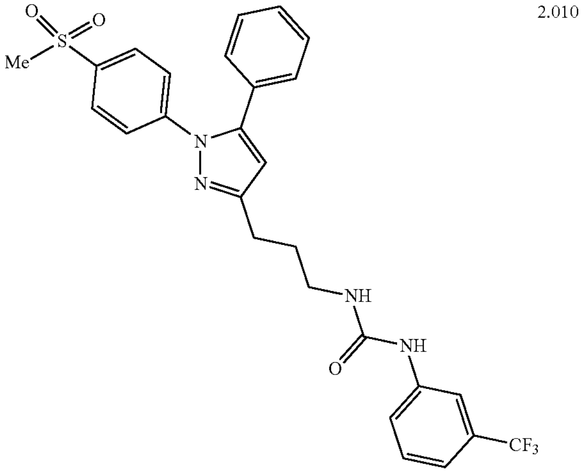 | 2.010 |
| 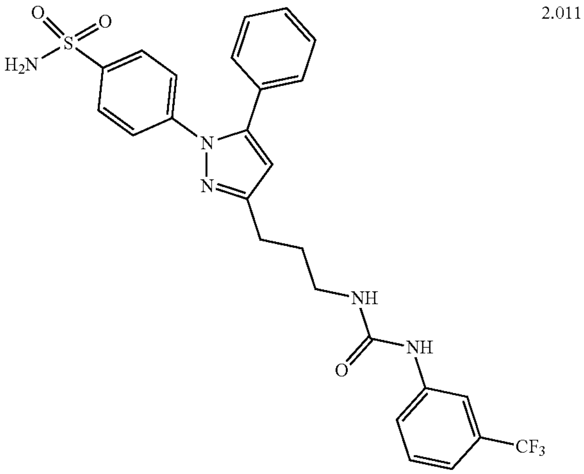 | 2.011 |
| 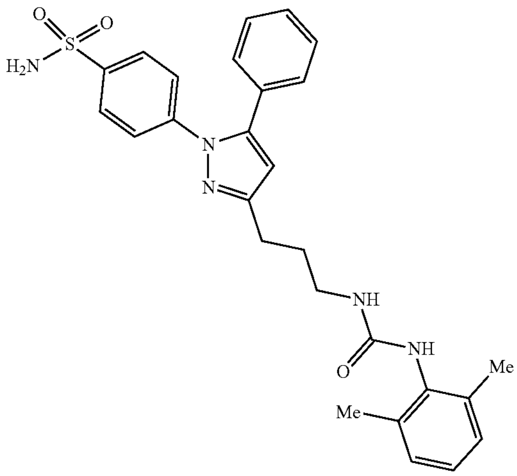 [SMILES: Cc1cccc(C)c1NC(=O)NCCCc1cc(-c2ccccc2)n(-c2ccc(S(N)(=O)=O)cc2)n1] | 2.012 |
| 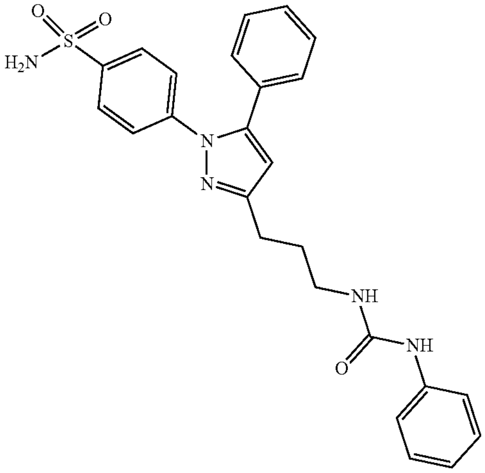 [SMILES: NS(=O)(=O)c1ccc(-n2nc(CCCNC(=O)Nc3ccccc3)cc2-c2ccccc2)cc1] | 2.013 |

TABLE 4-continued
| Compounds of Formula I Structure |
| --- |
| 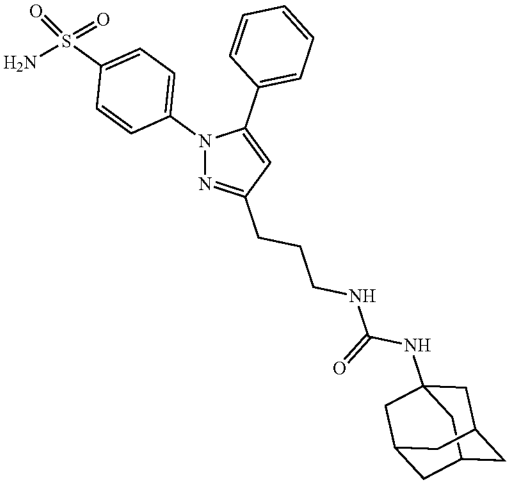 [SMILES: NS(=O)(=O)c1ccc(-n2nc(CCCNC(=O)NC34CC5CC(CC(C5)C3)C4)cc2-c2ccccc2)cc1] 2.014 |
| 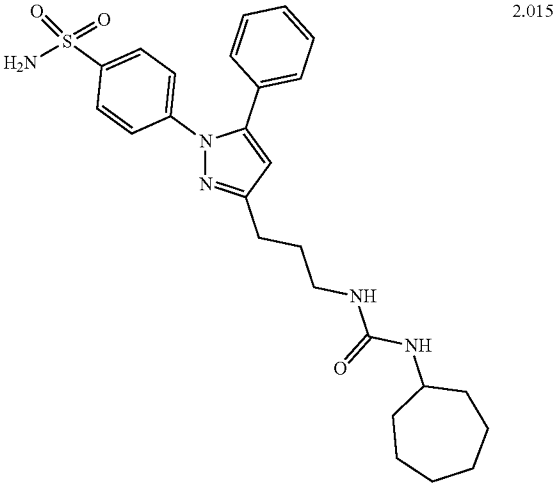 2.015 |
| 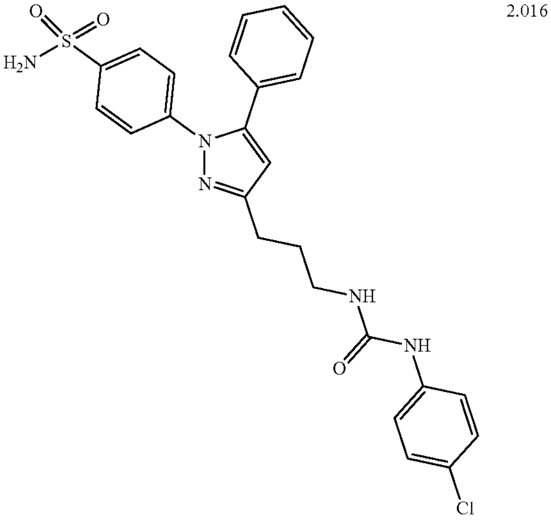 2.016 |
TABLE 4-continued
| Compounds of Formula I Structure |
| --- |
| 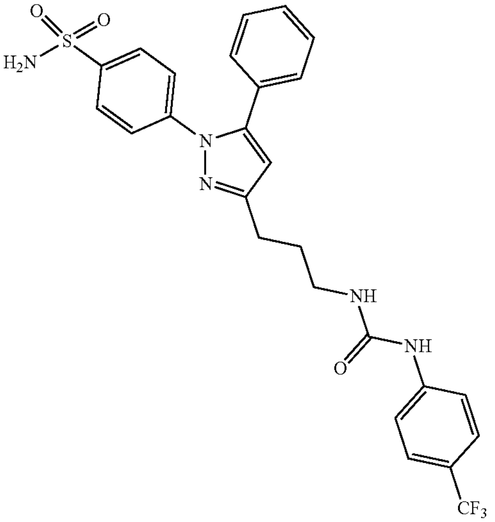 [SMILES: NS(=O)(=O)c1ccc(-n2nc(CCCNC(=O)Nc3ccc(C(F)(F)F)cc3)cc2-c2ccccc2)cc1] 2.017 |
| 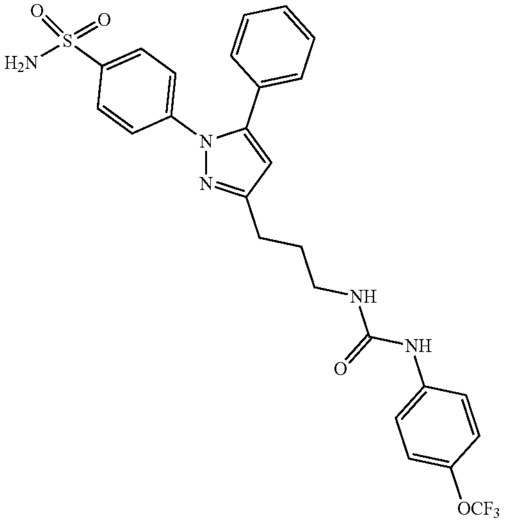 [SMILES: NS(=O)(=O)c1ccc(-n2nc(CCCNC(=O)Nc3ccc(OC(F)(F)F)cc3)cc2-c2ccccc2)cc1] 2.018 |
| 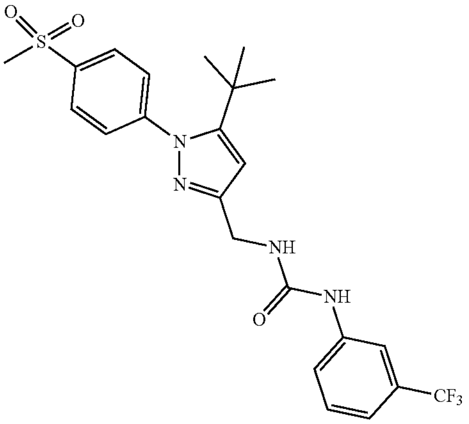 [SMILES: CC(C)(C)c1cc(CNC(=O)Nc2cccc(C(F)(F)F)c2)nn1-c1ccc(S(C)(=O)=O)cc1] 2.019 |

TABLE 4-continued

| Compounds of Formula I Structure | |
|---|---|
| 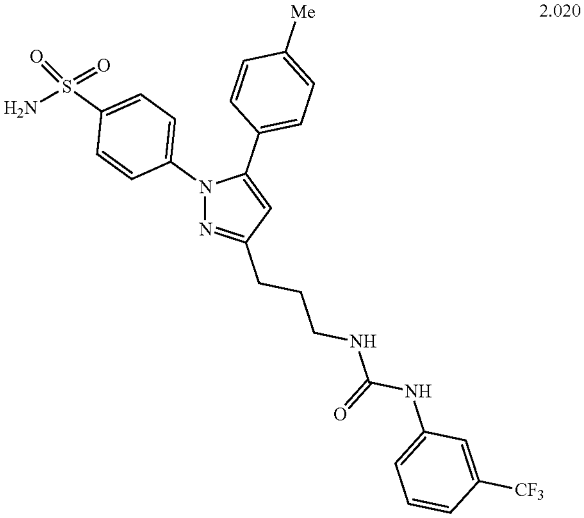 | 2.020 |

In other embodiments, the compound can be:

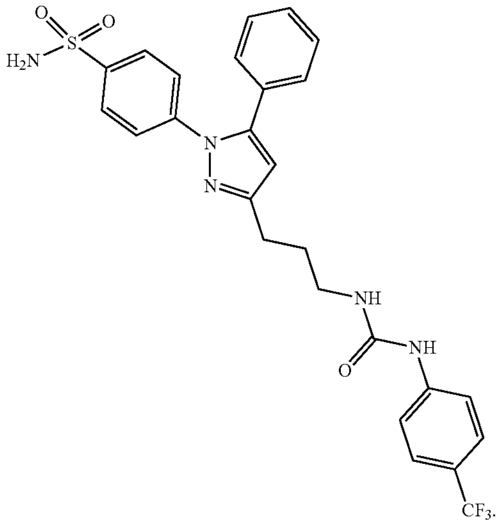 [SMILES: NS(=O)(=O)c1ccc(-n2nc(CCCNC(=O)Nc3ccc(C(F)(F)F)cc3)cc2-c2ccccc2)cc1]

The compounds of Formula I may exist as salts. The present invention includes such salts. Typically, the salts used are pharmaceutically acceptable salts, and will have the parameters noted above with respect to the compounds of Formula I.

Certain compounds of Formula I can exist in unsolvated forms as well as solvated forms, including hydrated forms. In general, the solvated forms are equivalent to unsolvated forms and are encompassed within the scope of the present invention. Certain compounds of Formula I may exist in multiple crystalline or amorphous forms. In general, all physical forms are equivalent for the uses contemplated by the present invention and are intended to be within the scope of the present invention.

Certain compounds of Formula I possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of Formula I do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer includes one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of Formula I may also contain unnatural proportions of atomic isotopes at one or more of the atoms that constitute such compounds. For example, the compounds of Formula I may be radiolabeled with radioactive isotopes, such as for example deuterium ($^{2}H$), tritium ($^{3}H$), iodine-125 ($^{125}I$), carbon-13 ($^{13}C$), or carbon-14 ($^{14}C$). All isotopic variations of the compounds of Formula I, whether radioactive or not, are encompassed within the scope of the present invention.

In addition to salt forms, the compounds of Formula I can be prepared as prodrugs. Prodrugs of the compounds described herein are those compounds that readily undergo chemical changes under physiological conditions to provide the compounds of Formula I. Additionally, prodrugs can be converted to the compounds of Formula I by chemical or biochemical methods in an ex vivo environment. For example, prodrugs can be slowly converted to the compounds of Formula I when placed in a transdermal patch reservoir with a suitable enzyme or chemical reagent.

The compounds of Formula I can be made by a variety of methods known in the art.

c. Compounds of Formula III

Compounds of Formula III characterized by the formula (III)

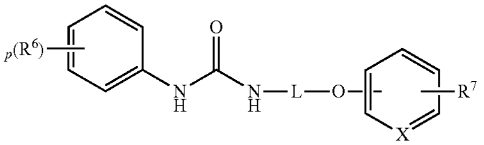

wherein $R^6$ is halogen, $C_{1-6}$ haloalkyl or $C_{1-6}$ haloalkoxy;

L is $C_{3-8}$ cycloalkyl;

$R^7$ is —CN, $C_{1-6}$ haloalkyl, $C_{1-6}$ haloalkoxy, —C(O)$OR^{7a}$ or —C(O)$NR^{7a}R^{7b}$;

$R^{7a}$ and $R^{7b}$ are each independently H, $C_{1-6}$ alkyl or $C_{3-8}$ cycloalkyl, or are taken together to form a 5- or 6-membered heterocycloalkyl ring;

X is —CH— or —N—; subscript p is an integer from 1 to 3; and pharmaceutically acceptable salts thereof.

In some embodiments, the compounds are those where when X is —CH—, L is cyclohexyl, $R^7$ is —C(O)OH, and subscript p is 1, then $R^6$ is halogen or $C_{1-6}$ haloalkyl.

Compounds of Formula III characterized by the Formula IIIa (IIIa)

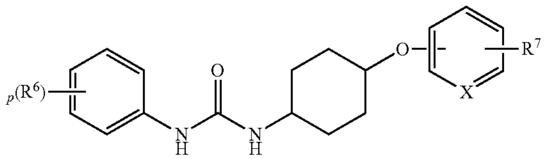

wherein $R^6$ is halogen, Ci haloalkyl or Ci haloalkoxy;

$R^7$ is —CN, $C_{1-6}$ haloalkyl, $C_{1-6}$ haloalkoxy, —C(O)$OR^{7a}$ or —C(O)$NR^{7a}R^{7b}$; $R^{7a}$ and $R^7$ are each independently H, $C_{1-6}$ alkyl or cycloalkyl, or are taken together to form a 5- or 6-membered heterocycloalkyl ring;

X is —CH— or —N—;

subscript p is an integer from 1 to 3; and salts or isomers thereof,

In some embodiments, the compounds of Formula III or a subembodment thereof are those where $R^6$ is halogen, $C_{1-6}$ haloalkyl or $C_{1-6}$ haloalkoxy;

$R^7$ is —CN, $C_{1-6}$ haloalkyl, $C_{1-6}$ haloalkoxy, —C(O)$OR^{7a}$ or —C(O)$NR^{7a}R^{7b}$;

$R^{7a}$ and $R^{7b}$ are each independently H, $C_{1-6}$ alkyl or cycloalkyl, or are taken together to form a 5- or 6-membered heterocycloalkyl ring;

X is —CH— or —N—;

subscript p is an integer from 1 to 3; such that when X is —CH—, $R^7$ is —C(O)OH, and subscript p is 1, then $R^6$ is halogen or $C_{1-6}$ haloalkyl; and pharmaceutically acceptable salts thereof.

In another embodiment, the compound has the formula:

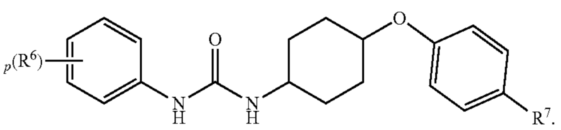

In other embodiments, the compound has the formula:

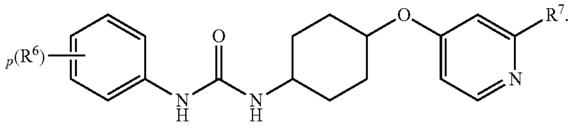

In other embodiments, the compound has the formula:

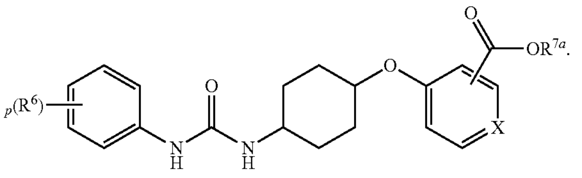

In other embodiments, the compound has the formula:

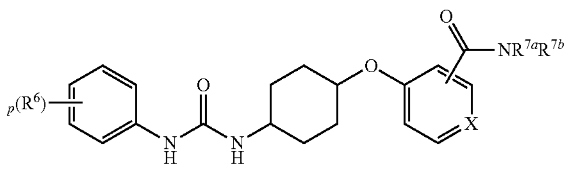

In other embodiments, the compound has the formula:

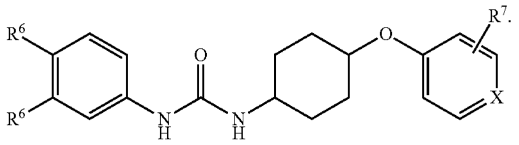

In other embodiments, the compound has the formula:

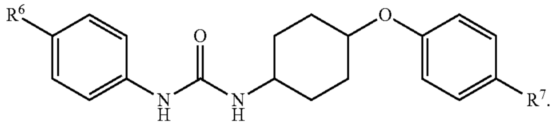

In some other embodiments, the present invention provides a compound of Formula III, selected from those in Table 5.

TABLE 5

| Compounds of Formula III Structure | |
|---|---|
| 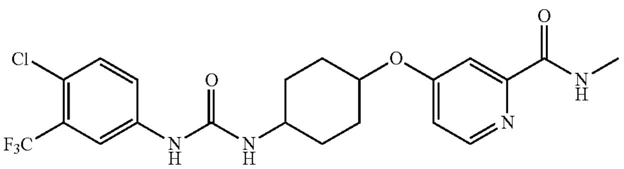 [SMILES: CNC(=O)c1cc(OC2CCC(NC(=O)Nc3ccc(Cl)c(C(F)(F)F)c3)CC2)ccn1] | 3.001 |

TABLE 5-continued
| Compounds of Formula III<br>Structure | |
|---|---|
| 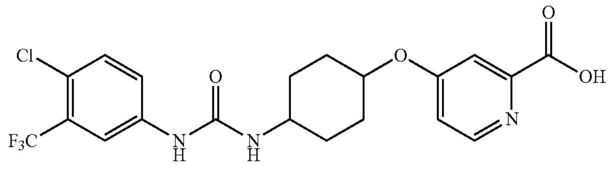 [SMILES: O=C(Nc1ccc(Cl)c(C(F)(F)F)c1)NC1CCC(Oc2ccnc(C(=O)O)c2)CC1] | 3.002 |
| 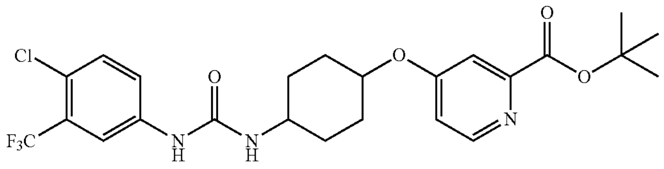 [SMILES: CC(C)(C)OC(=O)c1cc(OC2CCC(NC(=O)Nc3ccc(Cl)c(C(F)(F)F)c3)CC2)ccn1] | 3.003 |
| 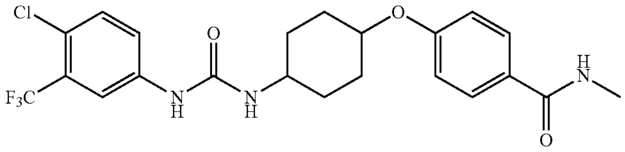 [SMILES: CNC(=O)c1ccc(OC2CCC(NC(=O)Nc3ccc(Cl)c(C(F)(F)F)c3)CC2)cc1] | 3.004 |
| 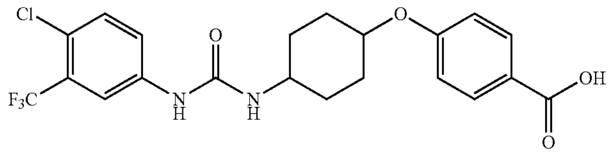 [SMILES: O=C(Nc1ccc(Cl)c(C(F)(F)F)c1)NC1CCC(Oc2ccc(C(=O)O)cc2)CC1] | 3.005 |
| 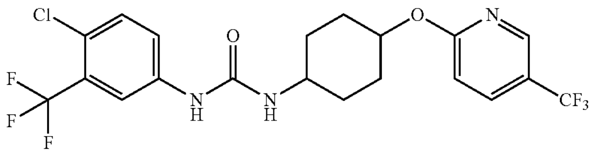 [SMILES: O=C(Nc1ccc(Cl)c(C(F)(F)F)c1)NC1CCC(Oc2ccc(C(F)(F)F)cn2)CC1] | 3.006 |
| 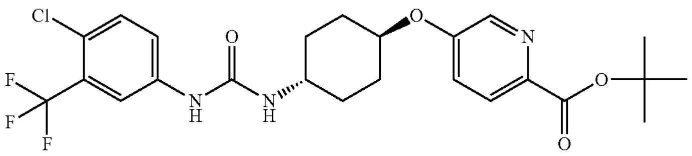 [SMILES: CC(C)(C)OC(=O)c1ccc(O[C@H]2CC[C@H](NC(=O)Nc3ccc(Cl)c(C(F)(F)F)c3)CC2)cn1] | 3.007 |
| 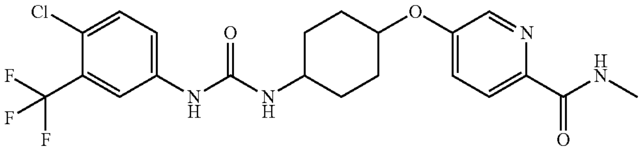 [SMILES: CNC(=O)c1ccc(OC2CCC(NC(=O)Nc3ccc(Cl)c(C(F)(F)F)c3)CC2)cn1] | 3.008 |
| 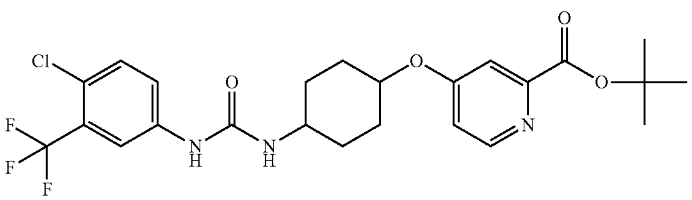 [SMILES: CC(C)(C)OC(=O)c1cc(OC2CCC(NC(=O)Nc3ccc(Cl)c(C(F)(F)F)c3)CC2)ccn1] | 3.009 |
| 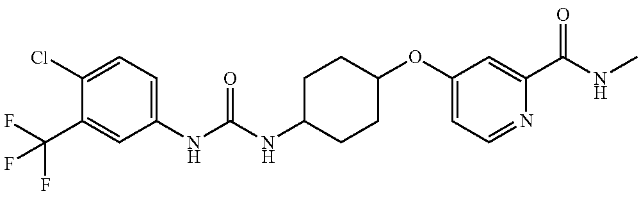 [SMILES: CNC(=O)c1cc(OC2CCC(NC(=O)Nc3ccc(Cl)c(C(F)(F)F)c3)CC2)ccn1] | 3.010 |

TABLE 5-continued
| Compounds of Formula III Structure | |
|---|---|
| 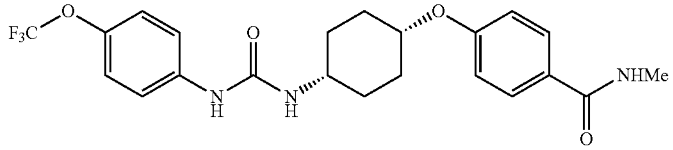 [SMILES: CNC(=O)c1ccc(O[C@H]2CC[C@@H](NC(=O)Nc3ccc(OC(F)(F)F)cc3)CC2)cc1] | 3.011 |
| 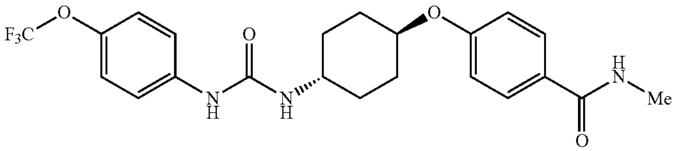 [SMILES: CNC(=O)c1ccc(O[C@H]2CC[C@H](NC(=O)Nc3ccc(OC(F)(F)F)cc3)CC2)cc1] | 3.012 |
| 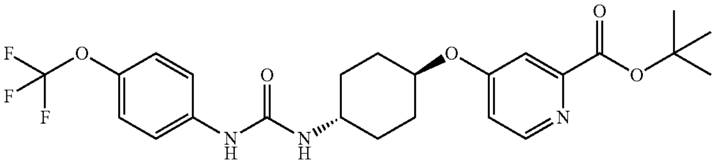 [SMILES: CC(C)(C)OC(=O)c1cc(O[C@H]2CC[C@H](NC(=O)Nc3ccc(OC(F)(F)F)cc3)CC2)ccn1] | 3.013 |
| 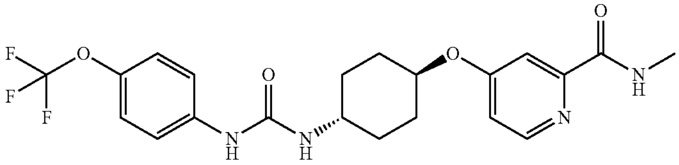 [SMILES: CNC(=O)c1cc(O[C@H]2CC[C@H](NC(=O)Nc3ccc(OC(F)(F)F)cc3)CC2)ccn1] | 3.014 |
| 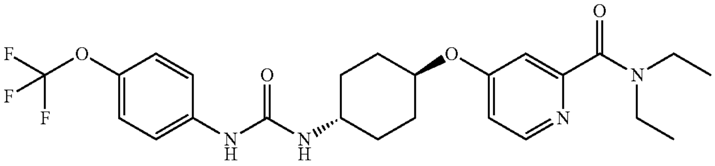 [SMILES: CCN(CC)C(=O)c1cc(O[C@H]2CC[C@H](NC(=O)Nc3ccc(OC(F)(F)F)cc3)CC2)ccn1] | 3.015 |
| 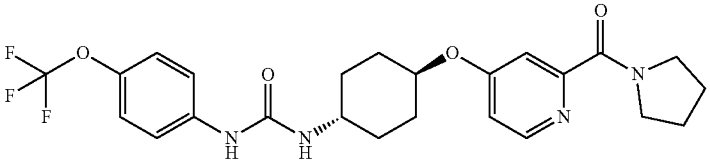 [SMILES: O=C(Nc1ccc(OC(F)(F)F)cc1)N[C@H]1CC[C@H](Oc2ccnc(C(=O)N3CCCC3)c2)CC1] | 3.016 |
| 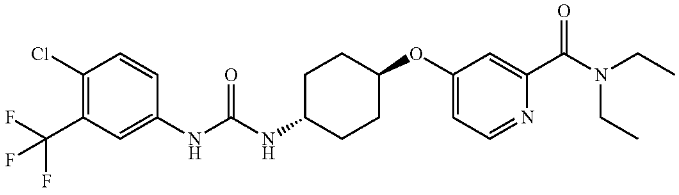 [SMILES: CCN(CC)C(=O)c1cc(O[C@H]2CC[C@H](NC(=O)Nc3ccc(Cl)c(C(F)(F)F)c3)CC2)ccn1] | 3.017 |
| 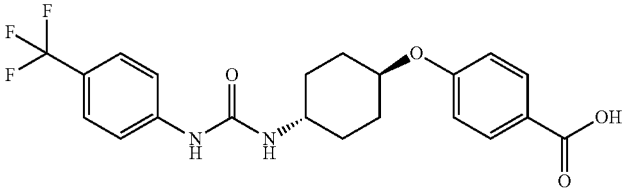 [SMILES: O=C(Nc1ccc(C(F)(F)F)cc1)N[C@H]1CC[C@H](Oc2ccc(C(=O)O)cc2)CC1] | 3.018 |
| 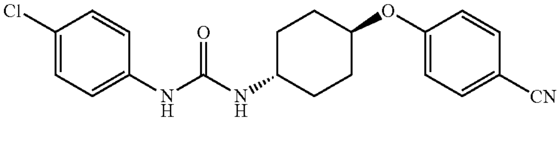 [SMILES: N#Cc1ccc(O[C@H]2CC[C@H](NC(=O)Nc3ccc(Cl)cc3)CC2)cc1] | 3.019 |

TABLE 5-continued

| Compounds of Formula III Structure | |
|---|---|
| 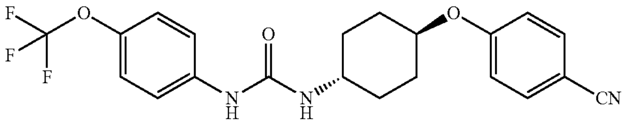 [SMILES: N#Cc1ccc(O[C@H]2CC[C@H](NC(=O)Nc3ccc(OC(F)(F)F)cc3)CC2)cc1] | 3.020 |
| 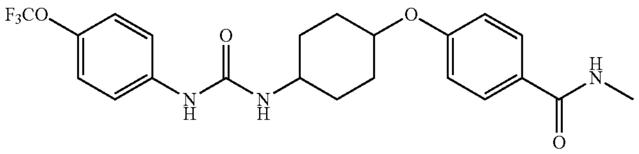 [SMILES: CNC(=O)c1ccc(OC2CCC(NC(=O)Nc3ccc(OC(F)(F)F)cc3)CC2)cc1] | 3.021 |
| 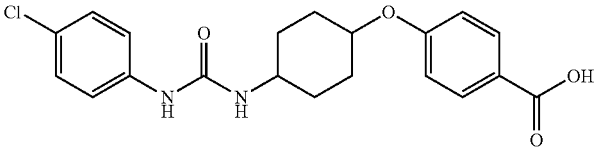 [SMILES: O=C(Nc1ccc(Cl)cc1)NC1CCC(Oc2ccc(C(=O)O)cc2)CC1] | 3.022 |
| 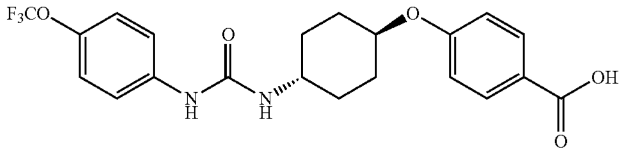 [SMILES: O=C(Nc1ccc(OC(F)(F)F)cc1)N[C@H]1CC[C@H](Oc2ccc(C(=O)O)cc2)CC1] | 3.023 |

In other embodiments, the compound is:

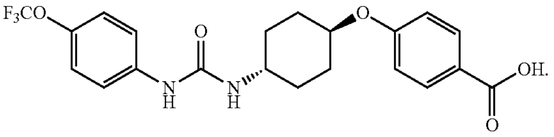 [SMILES: O=C(Nc1ccc(OC(F)(F)F)cc1)N[C@H]1CC[C@H](Oc2ccc(C(=O)O)cc2)CC1]

The compounds of Formula III may exist as salts. The present invention includes such salts. Typically, the salts used are pharmaceutically acceptable salts, and will have the parameters noted above with respect to the compounds of Formula III.

Certain compounds of Formula III can exist in unsolvated forms as well as solvated forms, including hydrated forms. In general, the solvated forms are equivalent to unsolvated forms and are encompassed within the scope of the present invention. Certain compounds of Formula III may exist in multiple crystalline or amorphous forms. In general, all physical forms are equivalent for the uses contemplated by the present invention and are intended to be within the scope of the present invention.

Certain compounds of Formula III possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of Formula III do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer includes one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of Formula III may also contain unnatural proportions of atomic isotopes at one or more of the atoms that constitute such compounds. For example, the compounds of Formula III may be radiolabeled with radioactive isotopes, such as for example deuterium ($^{2}H$), tritium ($^{3}H$), iodine-125 ($^{125}I$), carbon-13 ($^{13}C$), or carbon-14 ($^{14}C$). All isotopic variations of the compounds of Formula III, whether radioactive or not, are encompassed within the scope of the present invention.

In addition to salt forms, the compounds of Formula III can be prepared as prodrugs. Prodrugs of the compounds described herein are those compounds that readily undergo chemical changes under physiological conditions to provide the compounds of Formula III. Additionally, prodrugs can be converted to the compounds of Formula III by chemical or biochemical methods in an ex vivo environment. For example, prodrugs can be slowly converted to the compounds of Formula III when placed in a transdermal patch reservoir with a suitable enzyme or chemical reagent.

The compounds of Formula III can be made by a variety of methods known in the art.

In some embodiments, the compound of Formula III is selected from the compounds or pharmaceutical compositions disclosed in WO2012/112570 filed by the Regents of the University of California on Feb. 14, 2012. The contents of which is incorporated herein for all purposes.

Compositions, Formulation, and Administration

The compounds described herein can be prepared and administered in a wide variety of oral, parenteral and topical dosage forms. The compounds can be administered orally (e.g., topically, buccally), by injection, that is, intravenously, intramuscularly, intracutaneously, subcutaneously, intraduodenally, or intraperitoneally. The compounds can also be administered by inhalation, for example, intranasally. Additionally, the compounds can be administered transdermally.

The methods described herein include administration of compositions comprising a pharmaceutically acceptable carrier or excipient and one or more compounds described herein.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274, 166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, NY: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or *eucalyptus* oil compounds which, when applied to skin over an area presumably alter or off-set pain in joints or muscles served by the same nerves) and salicylates (e.g. BenGay®), are known and can be readily adapted for topical administration of the compounds described herein.

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of a compounds described herein, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

In varying embodiments, the agent or agents are formulated as oral compositions for delivery to the oral cavity of a mammal, e.g., in the form of toothpastes, mouth washes, oral gels, oral varnishes, and oral mucoadhesives. Illustrative excipients for use in oral compositions include without limitation, polyethylene glycols, humectants, vegetable oils, medium chain mono, di and triglycerides, lecithin, waxes, hydrogenated vegetable oils, colloidal silicon dioxide, polyvinylpyrrolidone (PVP) ("povidone"), celluloses, CARBOPOL™ polymers (Lubrizol Advanced Materials, Inc.) (i.e. crosslinked acrylic acid-based polymers), acrylate polymers, other hydrogel forming polymers, plasticizers, crystallization inhibitors, bulk filling agents, solubilizers, bioavailability enhancers and combinations thereof. In one embodiment, the agent or agents are formulated in a mucosal bioadhesive slow release carrier in the form of a mucoadhesive tablet. The mucosal bioadhesive slow release carrier comprises the agent or agents as the active ingredient, at least one diluent, at least one bioadhesive agent and at least one sustained release agent that provides sustained release of the active ingredient. This mucosal bioadhesive slow release carrier can also comprise a flowing agent, a wetting agent, a coloring agent, a flavouring agent and a binding agent. In varying embodiments, the bioadhesive agent can be a synthetic or a natural protein or a polysaccharide. The natural protein can be of vegetal or animal origin. It can be selected from the group of natural pea proteins, natural wheat proteins and gliadin proteins. In another aspect the natural protein can be from a milk protein concentrate. Proteins of natural origin of vegetal origin of use include those described in EP 07006042.1. Examples include natural pea proteins, natural wheat proteins and gliadin proteins and mixtures thereof. The method for producing pea proteins is described in WO 2007/017571. Polysaccharides useful in the formulation of oral mucosal bioadhesives include chitosan, alginate, carboxymethyl cellulose, hydroxypropyl methyl cellulose, hydroxyethyl cellulose, hydroxypropyl cellulose, cyclodextrin, sodium hyaluronate and xanthum gum. In another embodiment the protein of natural origin includes milk protein concentrate, e.g., by titrating a minimum of 85% of proteins, e.g., such as Prosobel L85, milk protein concentrate or, Promilk 852A sold by Armor Proteins, or from the Alaplex range (4850, 1180, 1380 or 1395) from NZMP. In varying embodiments, the relative concentration of the milk natural proteins in the bioadhesive tablet of the invention can be 15% to 50% by weight, preferably 20% to 30% by weight. In addition to the natural proteins, the mucosal bioadhesive slow release carrier contains at least one sustained release agent that provides sustained release of the active ingredient. This mucosal bioadhesive slow release carrier can also comprise a flowing agent, a wetting agent, a coloring agent, a flavouring agent and a binding agent.

Whatever the form in which the agents are topically administered (that is, whether by solid, liquid, lotion, gel, spray, etc.), in various embodiments they are administered at a dosage of about 0.01 mg to 10 mg per 10 $cm^2$. An exemplary dose for systemic administration is from about 0.001 μg/kg to about 100 mg/kg body weight of the mammal. In various embodiments, dose and frequency of administration of the compounds described herein are selected to produce plasma concentrations within the range of 2.5 μM and 30 nM. Generally, an efficacious or effective amount of a compound of the present disclosure is determined by first administering a low dose or small amount and then incrementally increasing the administered dose or dosages, until a desired effect of is observed in the treated subject with minimal or no toxic side effects. Applicable methods for determining an appropriate dose is described, for example, in *Goodman and Gilman's The Pharmacological Basis of Therapeutics,* 12th Edition, 2010, McGraw-Hill Professional; in a Physicians' Desk Reference (PDR), $70^{th}$ Edition, 2016, PDR Network; in *Remington: The Science and Practice of Pharmacy,* $21^{th}$ Ed., 2005, supra; and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

1. Methods of Monitoring

Clinical efficacy can be monitored using any method known in the art. Measurable parameters useful in monitoring improvement include measuring the frequency or severity of one or more symptoms associated with ACM (e.g., heart palpitations, dizziness, fainting, shortness of breath, chest pain, fatigue, swelling in the legs and other areas, persistent cough, or a combination thereof) as well as clinical parameters (e.g., echocardiogram, Holter monitor, electrophysiologic testing, cardiac MRI, cardiac CT scan, or a combination thereof)

Observation of the stabilization, improvement and/or reversal of one or more symptoms or parameters by a measurable amount indicates that the treatment or prevention regime is efficacious.

In certain embodiments, the monitoring methods can entail determining a baseline value of a measurable trait or disease parameter in a subject before administering a compound described herein, and comparing this with a value for the same measurable trait or parameter after a course of treatment.

In other methods, a control value (i.e., a mean and standard deviation) of the trait or parameter is determined for a control population. In certain embodiments, the individuals in the control population have not received prior treatment and do not have the disease condition subject to treatment, nor are at risk of developing the disease condition subject to treatment. In such cases, if the value of the measurable trait or clinical parameter approaches the control value, then treatment is considered efficacious. In other embodiments, the individuals in the control population have not received prior treatment and have been diagnosed with the disease condition subject to treatment. In such cases, if the value of the measurable trait or clinical parameter approaches the control value, then treatment is considered inefficacious.

In other methods, a subject who is not presently receiving treatment but has undergone a previous course of treatment is monitored for one or more of the traits or clinical parameters to determine whether a resumption of treatment is required. The measured value of one or more of the traits or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable trait or clinical parameter approaches the control value, then treatment is considered efficacious and need not be resumed. In all of these cases, a significant difference relative to the control level (i.e., more than a standard deviation) is an indicator that treatment should be resumed in the subject.

In some embodiments, the described therapeutic methods maintain or reduce the number of premature ventricular contractions (PVCs) experienced by a subject as measured by ECG or Holter monitor (e.g., the treatment prevents/mitigates disease progression or improves a measureable clinical parameter). For example, in some embodiments, a subject after 20 weeks of treatment has about the same number of PVCs as compared to the number of PVCs in the same subject prior to treatment as measured with a Holter monitor over a 2-day period. In some embodiments, a subject after 20 weeks of treatment has at least a 10% reduction in the number of PVCs as compared to the number of PVCs in the same subject prior to treatment as measured with a Holter monitor over a 2-day period.

In some embodiments, the described therapeutic methods maintain or reduce the number of implantable cardioverter-defibrillator (ICD) shocks experienced by a subject (e.g., the treatment prevents/mitigates disease progression or improves a measureable clinical parameter). For example, in some embodiments, a subject after 20 weeks of treatment has about the same number of ICD shocks over a three week period as compared to the number of ICD shocks in the same subject over a three week period prior to treatment. In some embodiments, a subject after 20 weeks of treatment has at least a 10% reduction in the number of IDC shocks over a three week period as compared to the number of IDC shocks in the same subject over a three week period prior to treatment.

EXAMPLES

The following examples are offered to illustrate, but not to limit the claimed invention.

Example 1

Pharmacological Inhibition Using Compounds of Formula or Compounds of Formula II Prevents Development of ACM in an In Vitro Model

Materials and Methods

Neonatal rat ventricular myocytes (NRVM) were isolated from the ventricles of 1-day-old Wistar rat pups and plated on collagen-coated plastic chambers. 24 hours following seeding, the cells were transfected with an adenoviral construct expressing a mutant form of plakoglobin known to cause arrhythmogenic cardiomyopathy in patients (2157del2 JUP). 24 hours following transfection, the cells were treated with 500 nM 2.017 or 1 μM 1.045 for an additional 24 hours. Non-transfected cultures and cultures transfected with the adenoviral construct only served as negative and positive controls, respectively.

Immunofluorescence: Cell cultures were fixed with 4% paraformaldehyde and prepared for immunofluorescence analysis as previously described (1). Primary antibodies included mouse monoclonal anti-Cx43 (Millipore, MAB3067 1:200) and anti-phospho-RelA (Cell signaling technology, 3033S, 1:200). Cy3-conjugated goat anti-mouse and anti-rabbit antibodies (Jackson Immunolabs) were used as secondary antibodies and DAPI was used to visualize the nuclei. Immunostained preparations were visualized by confocal microscopy and changes in spatial distribution of signal were assessed qualitatively.

Apoptosis assay: Terminal deoxynucleotidyl transferase dUTP nick end labelling (TUNEL) was performed on NRVM cultures following the manufacturer's instructions (Millipore, S7110). DNA strand breaks generated in apoptotic cells were labelled with fluorescein (green) and nuclei were visualized with DAPI. The number of TUNEL-positive nuclei was counted in 5 randomly selected high-power fields in each culture well and expressed as a percent of total nuclei visualized with DAPI.

Results

Figure 1C:
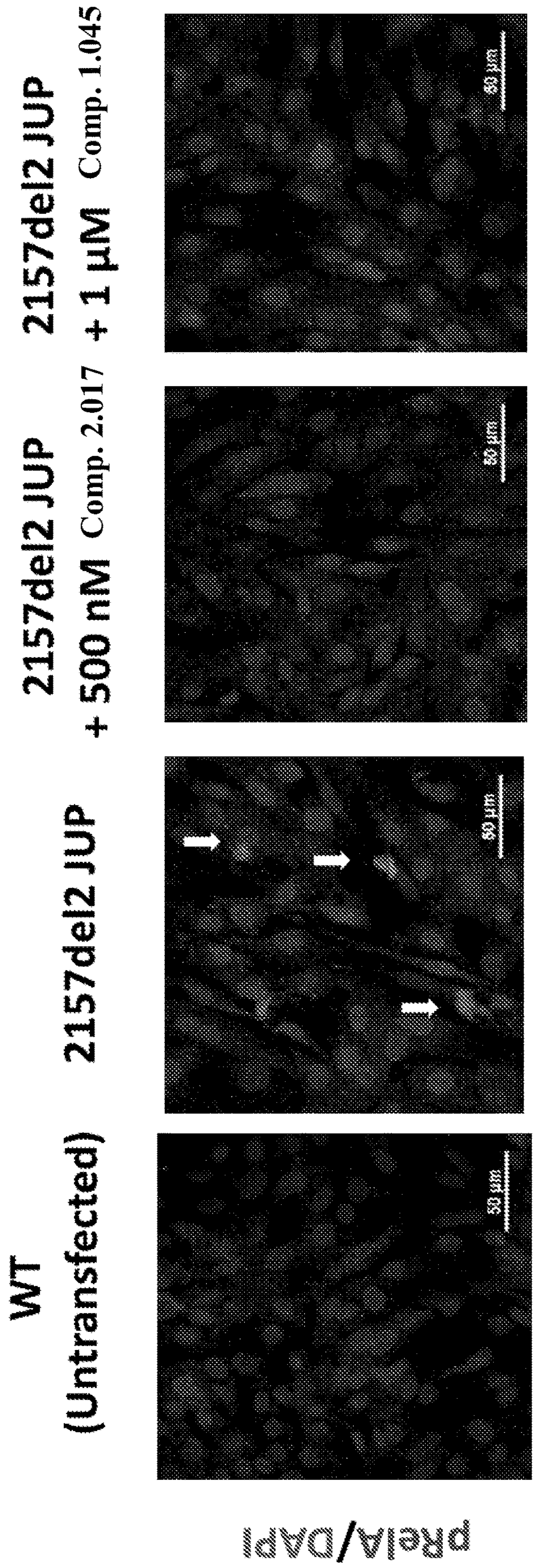
Figure 1D:
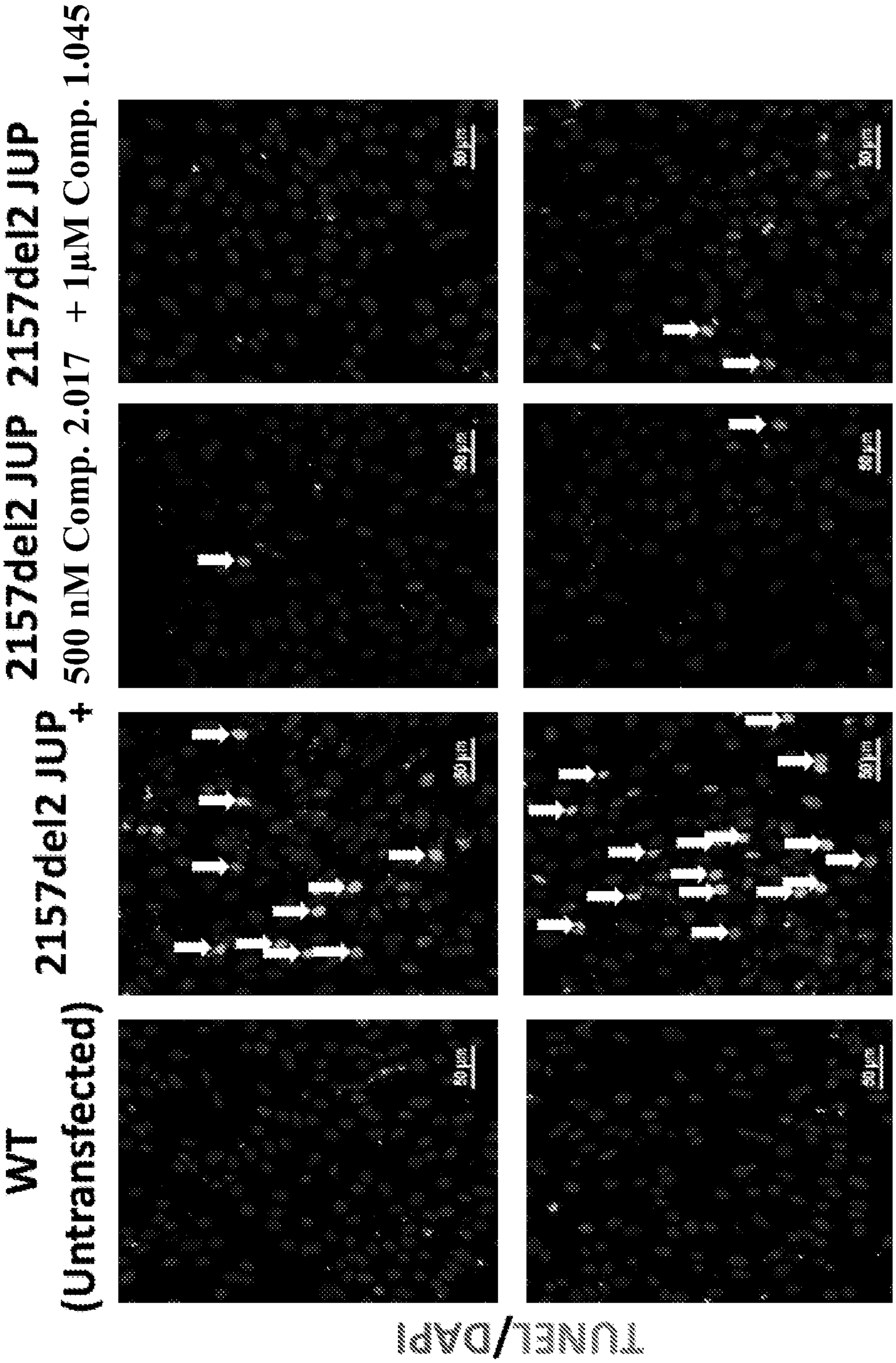

As shown in FIG. 1A-D, both compounds 2.017 and 1.045 prevented redistribution of junctional plakoglobin to intracellular/nuclear sites (FIG. 1A), reduced loss of cell surface signal for Cx43 (the major ventricular gap junction protein) (FIG. 1B), greatly diminished myocyte apoptosis (FIG. 1D) and prevented activation of NFκB (FIG. 1C). Furthermore, exposure to 14,15-EE-5(Z)E, a downstream product of soluble epoxide hydrolase, intensified ACM disease readouts (data not shown). The results from using the noted inhibitors suggests that these inhibitors will be advantageous in reversing ACM.

Redistribution of cell-cell junction proteins in cardiac myocytes is seen in nearly all ACM patients. The data provided herein demonstrate that Compounds 2.017 and 1.045 prevent ACM disease progression in this model and will be useful in the treatment of ACM.

Example 2

Failed Resolution and ER-Stress in Dsg2$^{mut/mut}$ Mice and ACM Patients

Figures 2A, 2B, 2C, 2D, 2E, 2F:
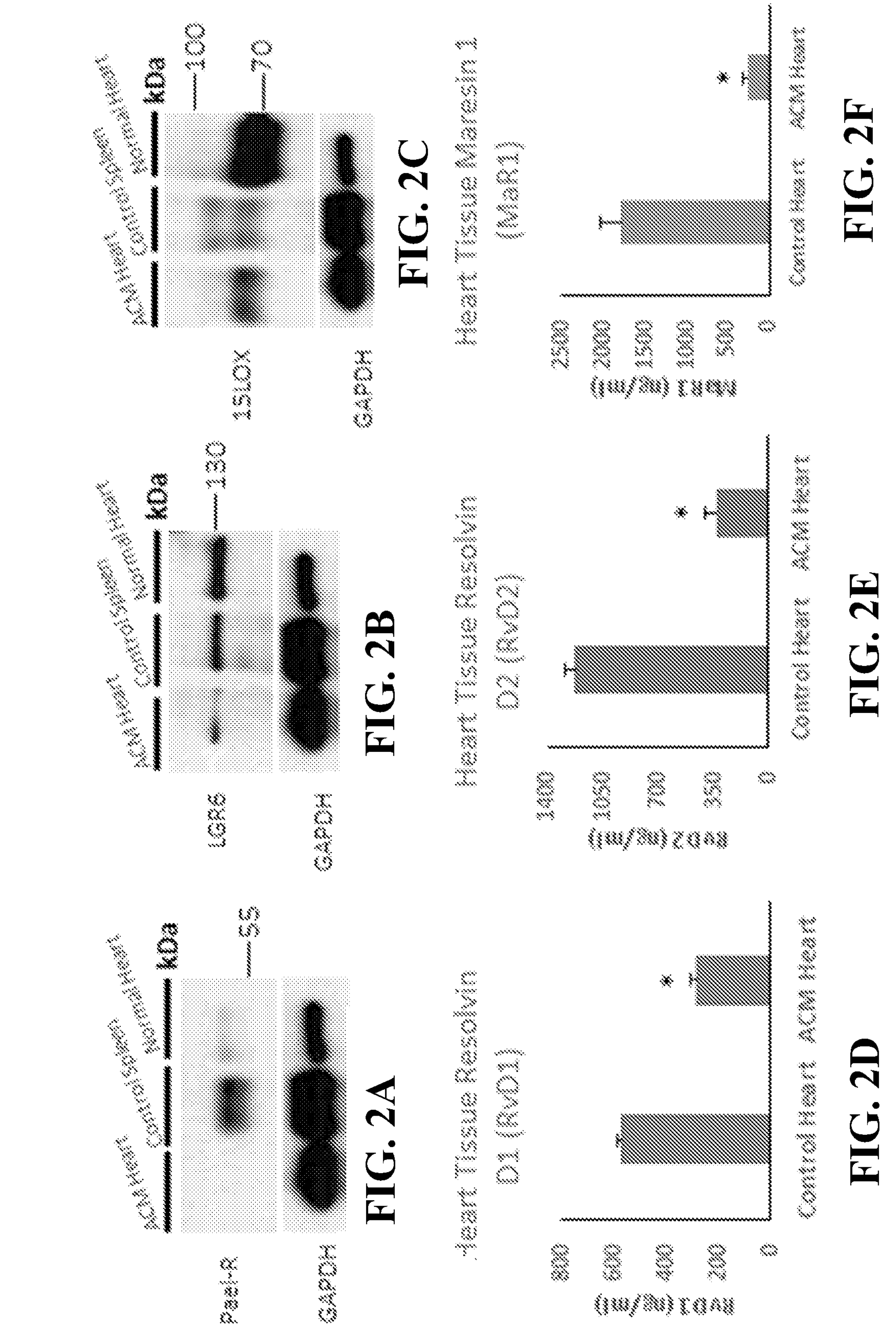
FIG. 2A-G shows that sEH protein levels are greatly increased in hearts of Dsg2$^{mut/mut}$ mice. (A)-(C): Expression of SPM receptors and 15-LOX in hearts of 16 week-old Dsg2$^{mut/mut}$ mice vs. normal heart and spleen. The amount of protein loaded in normal heart samples was deliberately decreased to highlight differences in expression between ACM and controls. (D)-(F): ELISA assays showing reduced expression of SPMs in hearts of 16 week old Dsg2$^{mut/mut}$ mice vs. normal hearts (n=3; *p<0.05). (G) Western blots of sEH expression.
Figure 2G:
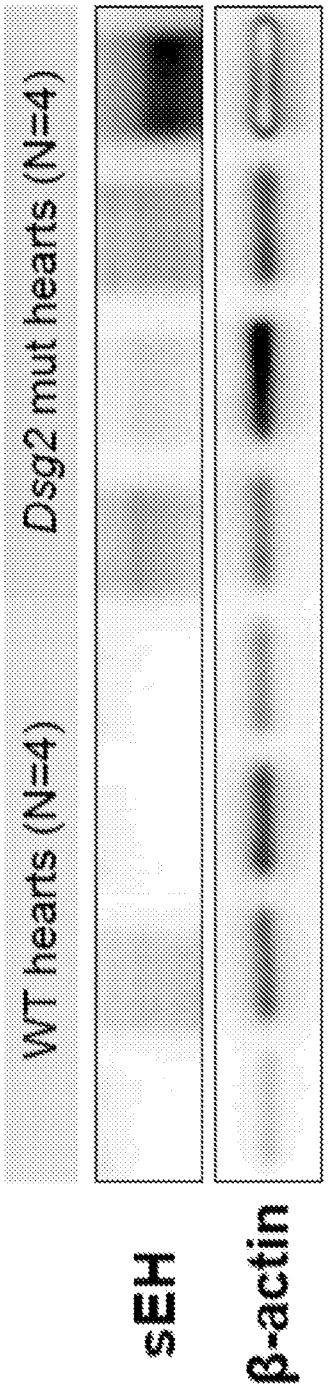
Figure 3A:
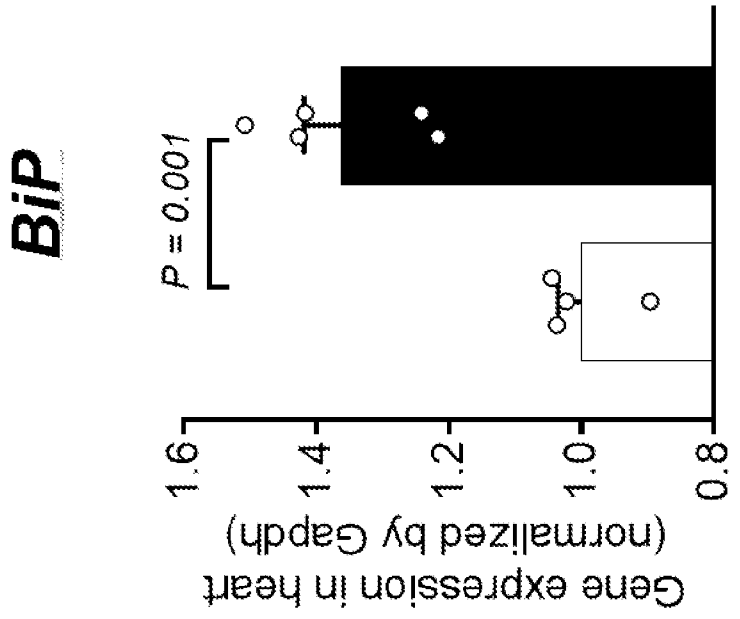
FIG. 3A-E qPCR analysis of ER-stress response markers (BiP (A), and PDI (B)), Cox-2 (C) and PGE2 receptors (Ep2 (D) and Ep4 (E)) in hearts of Dsg2$^{mut/mut}$ mice (black bars; n=5) vs. wildtype control hearts (white bars; n=4).
Figure 3B:
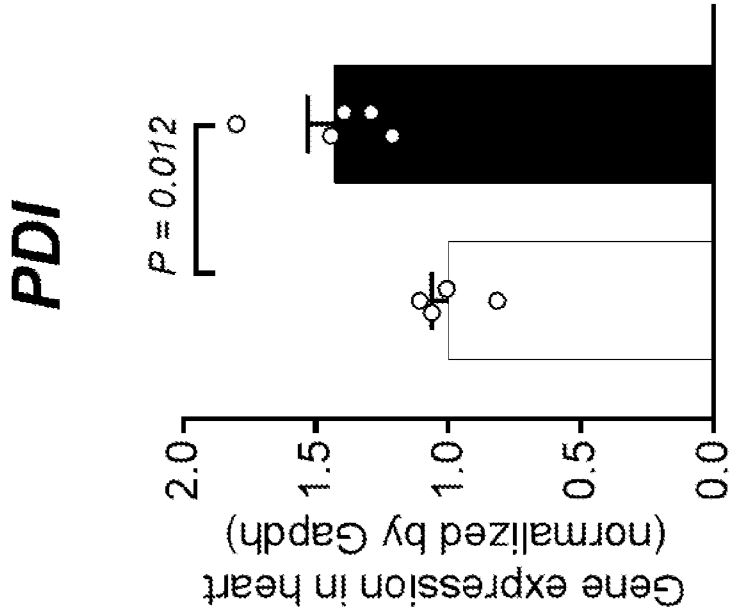
Figure 3C:
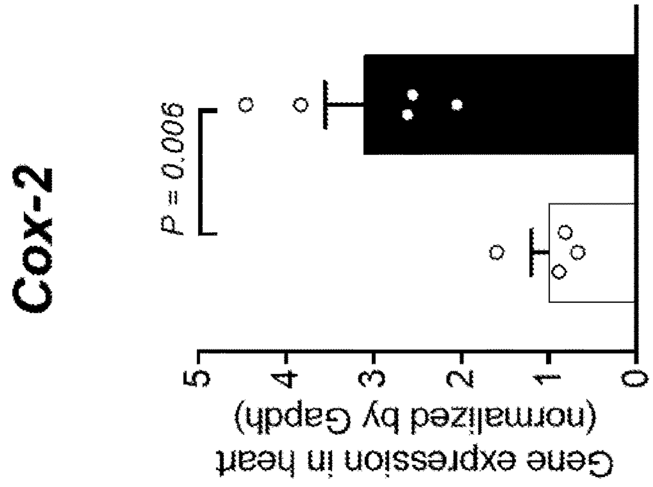
Figure 3D:
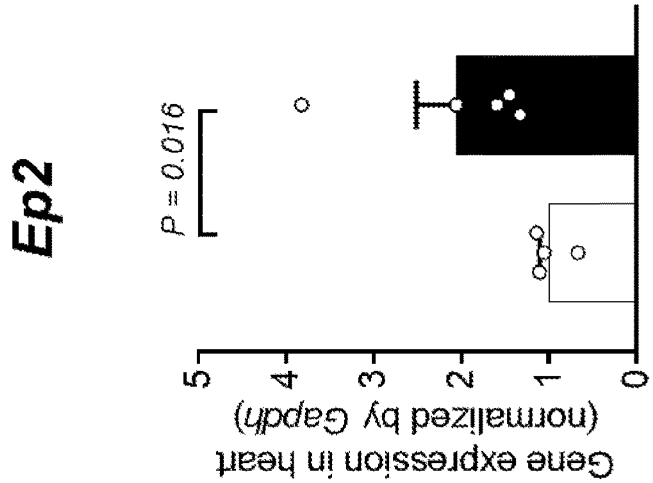
Figure 3E:
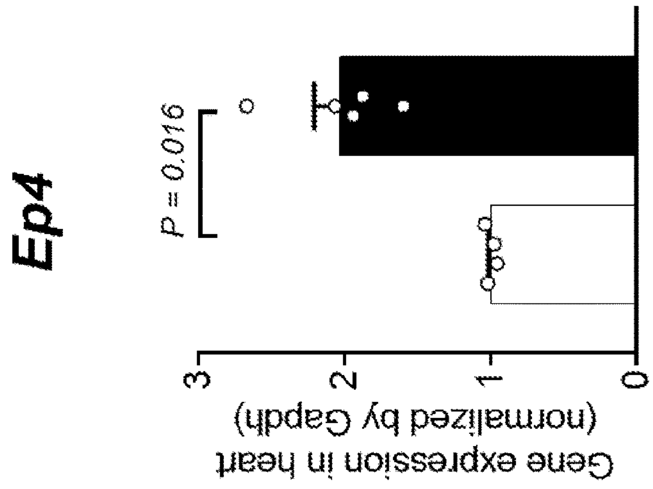
Figure 4D:
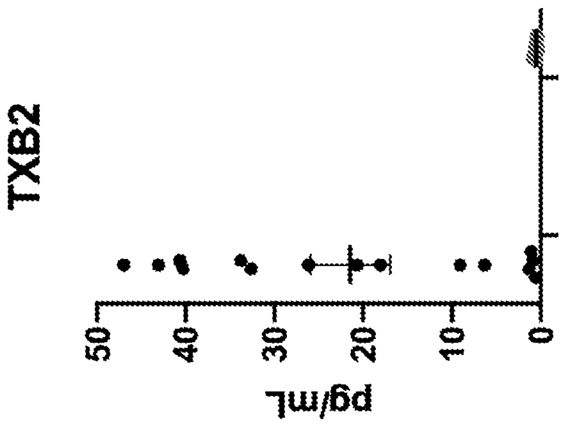
FIG. 4A-D LC-MS/MS assays of serum from 15 ACM patients (left) compared to control samples (right) showing elevated levels of (A, B) DiHOMEs, (C) prostaglandin E2 (PGE2) and (D) thromboxane B2 (TXB2; a metabolite of thromboxane A2) in ACM patients.
Figure 4C:
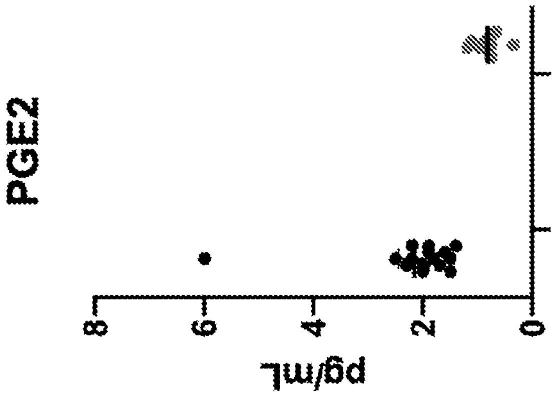
Figure 4B:
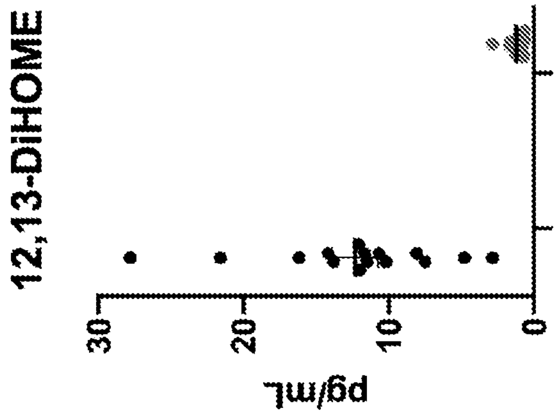
Figure 4A:
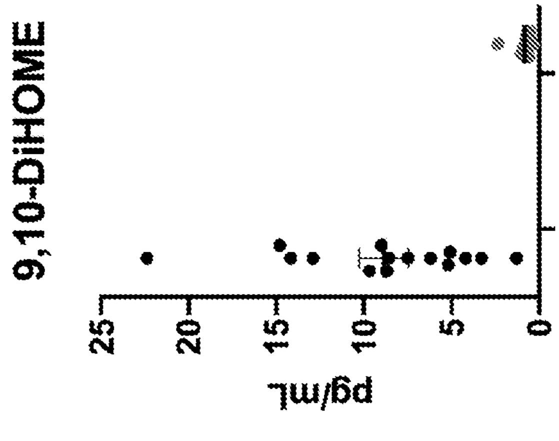

Expression of the SPM protectin D1 receptor Pael-R (GPR37) is virtually absent in hearts of 16 week-old Dsg2$^{mut/mut}$ mice and expression of the SPM maresin receptor LGR6 and the SPM synthetic enzyme 15-LOX is greatly reduced (FIG. 2). ELISA showed similar reductions in SPMs—resolvins D1 (↓51%) and D2 (↓73%), and maresin-1 (↓86%) (FIG. 2). LC-MS/MS assays of hearts and plasma from 16 week Dsg2$^{mut/mut}$ mice showed remarkable results: plasma 14,15-EETs were reduced by 37-fold in ACM vs. controls, and 14,15-EpETE was undetectable. Levels of 14,15-EpETE and 8,9-EpETE were reduced by 4-5-fold in ACM hearts. Of particular significance, sEH protein levels are greatly increased in hearts of Dsg2$^{mut/mut}$ mice (FIG. 2). This is a dramatic increase in sEH expression which likely has marked metabolic impact. These data further support that sEH inhibitors will reduce the severity of ACM.

In additional studies, mRNA transcripts of genes for CYP2s1 and CYP2e1 were virtually undetectable in hearts of Dsg2$^{mut/mut}$ mice (data not shown). CYP2s1 is a macrophage P450 enzyme which forms epoxides of fatty acids.

Like CYP2e1, it generates EETs from arachidonic acid. CYP-derived EETs enhance pro-resolving activities in macrophages and suppress inflammation by blocking NFκB. Downregulation of macrophage CYP2s1 also decreases production of the wound-healing mediator, 12-HHT. These results reveal a marked imbalance between pro-inflammatory and pro-resolving mediators in ACM.

qPCR analysis showed increased expression of ER-stress response genes, Cox-2 and PGE2 receptors in hearts of $Dsg2^{mut/mut}$ mice (FIG. 3)—all indicators of failed resolution. LC-MS/MS assays on serum from 15 ACM patients with desmoso-mal gene variants were compared to assays of control samples. Increases were seen in >40 lipid mediators including 9,10- and 12,13-DiHOMEs, and other pro-inflammatory eicosanoids such as PGE2 and TXB2 (a metabolite of TXA2) (FIG. 4). Of note, 9,10- and 12,13-DiHOMES are derived from metabolism of linoleic acid, the most abundant fatty acid in the human diet, and are produced by sEH. These new data are, thus, a powerful clinical indicator of ER-stress and unresolved inflammation in ACM.

Example 3

Effects of sEH Inhibitors and EETs in ACM

Figure 5A:
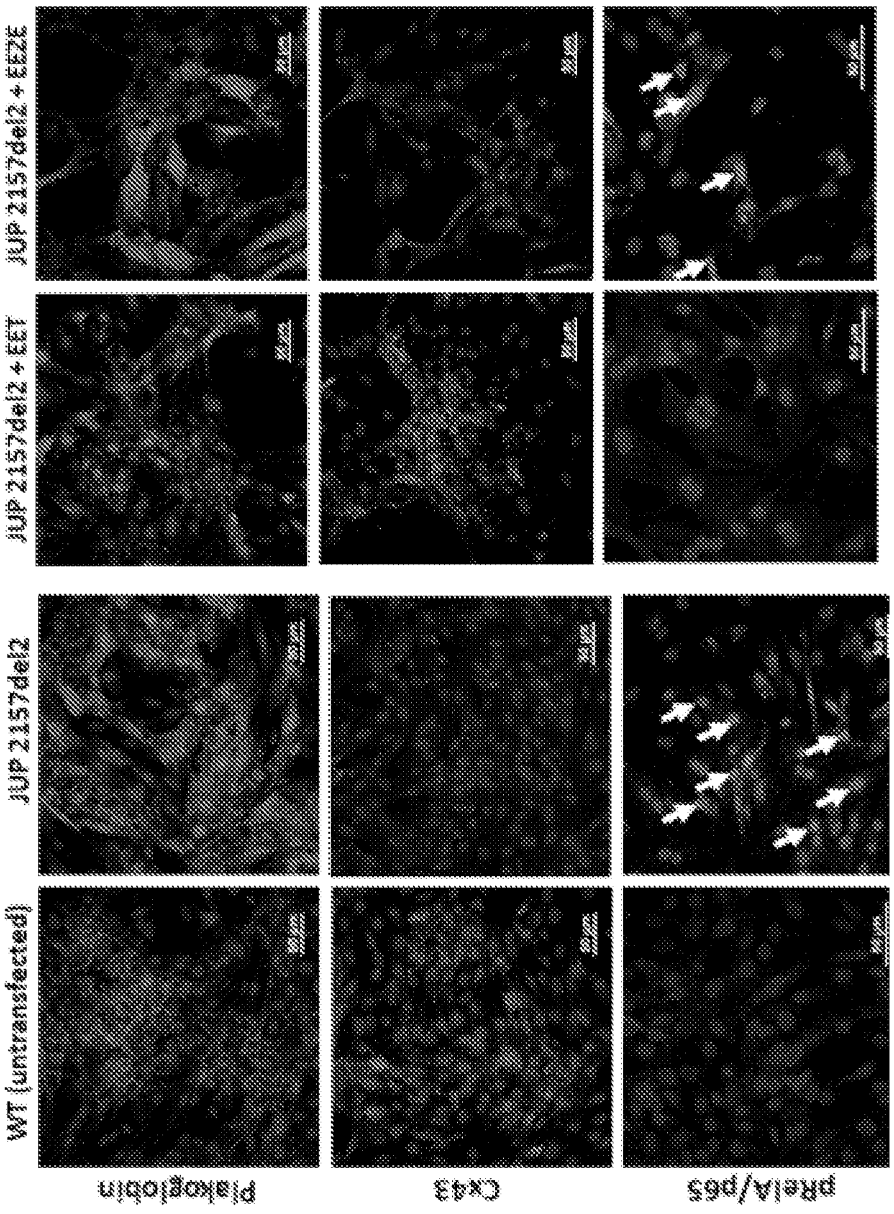
FIG. 5A-B sEH inhibitors and EETs reverse ACM in vitro and in vivo. (A) Jup2157del2 cells show redistribution of plakoglobin, loss of cell surface Cx43, nuclear pRelA/p65 signal (indicating activation of NFκB), and apoptosis (TUNEL+nuclei; arrows). These effects were reversed by 14,15-EET (EET; 10 μM). 14,15-EE-5(Z)E (EEZE; 10 M) intensified these ACM features. (B) Dsg2$^{mut/mut}$ mice treated with the sEH blocker Compound 1.045 (black points) recovered LV function vs. untreated mice (grey points). The functional recovery persisted in treated mice after administration of Compound 1.045 was discontinued.
Figure 5B:
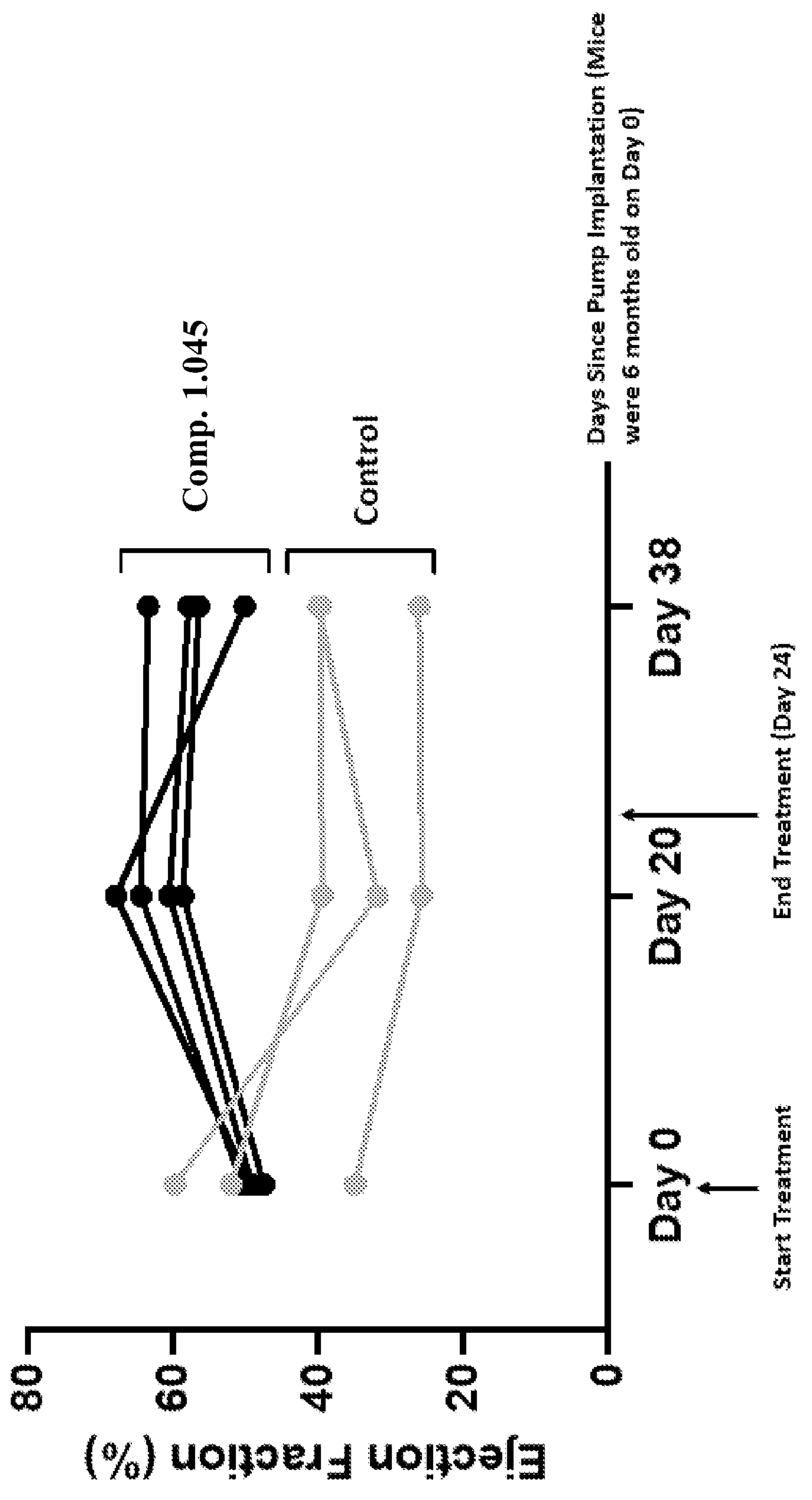

In vitro, rat ventricular myocytes that express JUP2157del2, a pathogenic variant in the gene for the desmosomal protein plakoglobin, exhibit key features seen in patients including redistribution of intercalated disk proteins, myocyte apoptosis, production of inflammatory cytokines, and activation of NFκB signaling. Indeed, redistribution of cell-cell junction proteins in cardiac myocytes occurs in nearly all ACM patients, and loss of junctional plakoglobin signal is a diagnostic feature of ACM. We treated cells with 500 nM Comp. 2.017 (4-(5-phenyl-3-{3-[4-trifluoromethyl-phenyl)-ureido]-propyl}-pyrazol-1-yl)-benzenesulfonamide) or 1 M Comp. 1.045 (1-trifluoro-methoxy-phenyl-3-(1-propionylpiperidin-4-yl) urea). Comp. 1.045 is a highly specific sEH blocker; Comp. 2.017 is a combined sEH and COX-2 inhibitor. Both drugs prevented translocation of junctional plakoglobin to intracellular/nuclear sites, reduced loss of cell surface Cx43 (the major cardiac gap junction protein), greatly diminished myocyte apoptosis, and blocked activation of NFκB (data not shown due to page limitations). Repeat studies with two other sEH inhibitors, Comp. 1,002 and Compound 3.023, showed similar results. In related studies, treating ACM cells with 14,15-EET, a pro-resolving EpFA, produced potent salutary effects, and 14,15-EE-5(Z)E, which antagonizes actions of 14,15-EET, intensified ACM disease readouts (FIG. 5). Of note, levels of 14,15-EET are greatly reduced in the hearts and plasma of $Dsg2^{mut/mut}$ mice. The in vivo results were truly remarkable. Treating $Dsg2^{mut/mut}$ mice with Compound 1.045 (another sEH inhibitor in clinical trials) for only 20 days (3 mg/kg/day) led to marked recovery of LV function (FIG. 5). These results show that the tested compounds can rescue the disease both in vitro and in vivo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preventing, mitigating, decreasing, reversing and/or treating Arrhythmogenic Cardiomyopathy (ACM) in a subject in need thereof, comprising administering to the subject an effective amount of a dual cyclooxygenase-2 (COX-2)/inhibitor of soluble epoxide hydrolase (sEH) having Formula I (I)

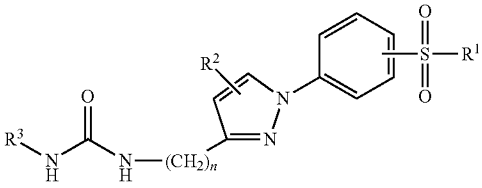

wherein $R^1$ is selected from the group consisting of $C_{1-6}$ alkyl, $—NR^{1a}R^{1b}$ and $C_{3-6}$ cycloalkyl;

$R^{1a}$ and $R^{1b}$ are each independently selected from the group consisting of H and $C_{1-6}$ alkyl;

$R^2$ is selected from the group consisting of $C_{1-6}$ alkyl, $C_{3-6}$ cycloalkyl and aryl, wherein the cycloalkyl and aryl are each optionally substituted with $C_{1-6}$ alkyl;

$R^3$ is selected from the group consisting of $C_{5-10}$ cycloalkyl and aryl, each optionally substituted with from 1 to 3 $R^{3a}$ groups wherein each $R^{3a}$ is independently selected from the group consisting of $C_{1-6}$ alkyl, $C_{1-6}$ alkoxy, halogen, $C_{1-6}$ haloalkyl and $C_{1-6}$ haloalkoxy;

subscript n is an integer from 0 to 6; and pharmaceutically acceptable salts thereof.

2. The method of claim 1, wherein the dual cyclooxygenase-2 (COX-2)/inhibitor of soluble epoxide hydrolase (sEH) has the Formula Ic:

(Ic)

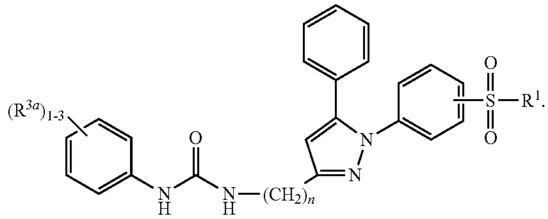

3. The method of claim 1, wherein the compound of Formula I is

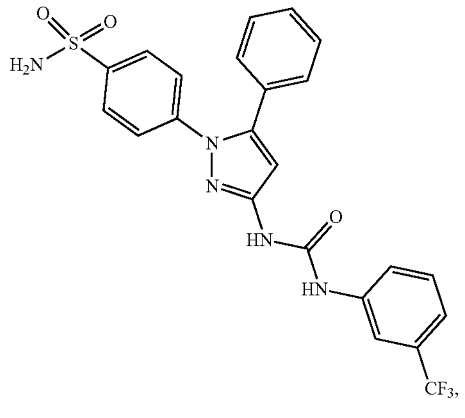

-continued
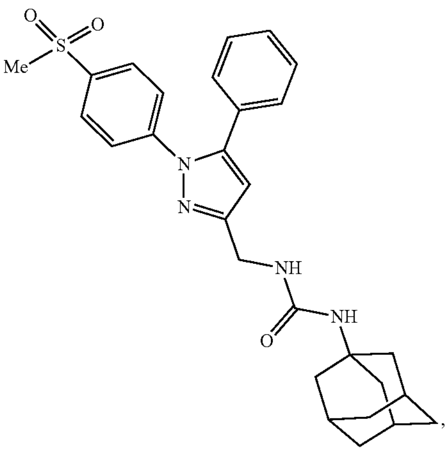
,
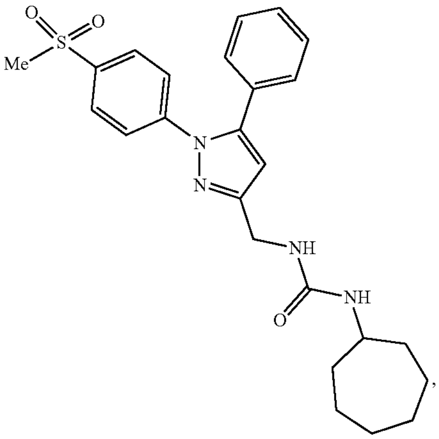
,
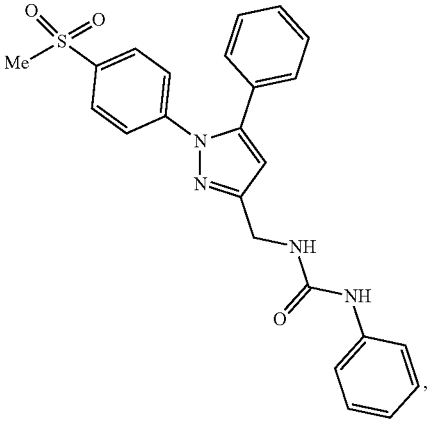
,
-continued
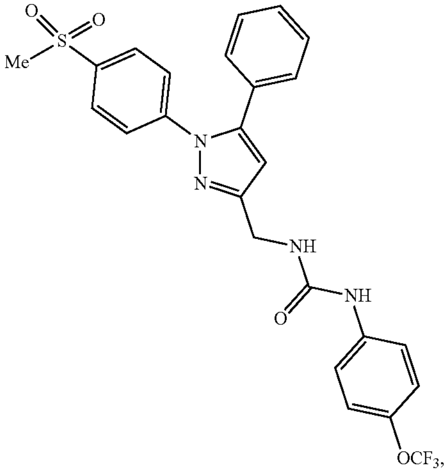
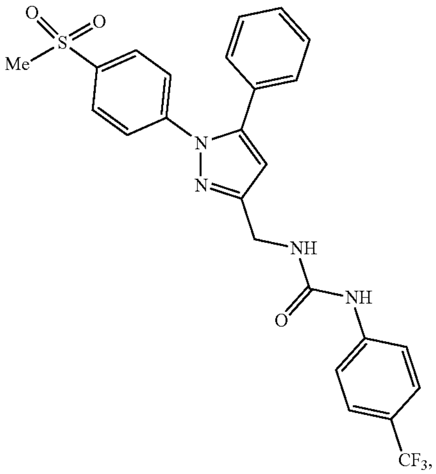
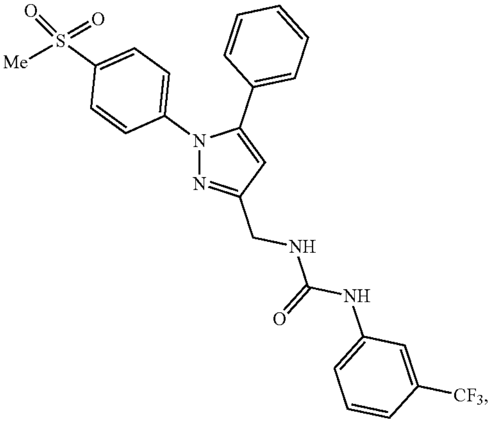

-continued
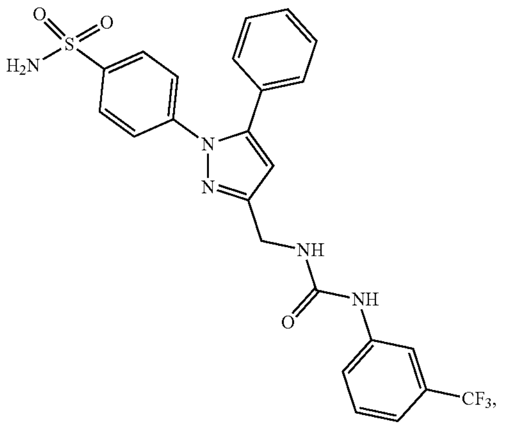
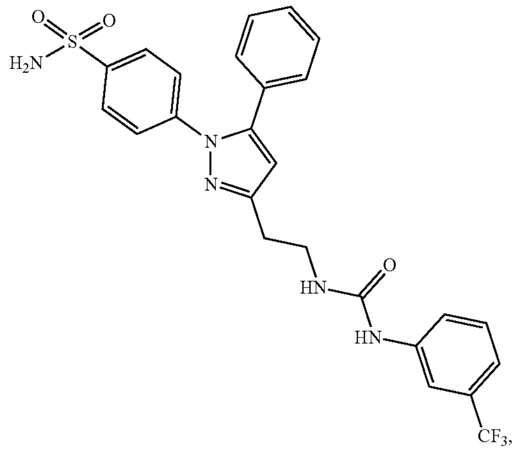
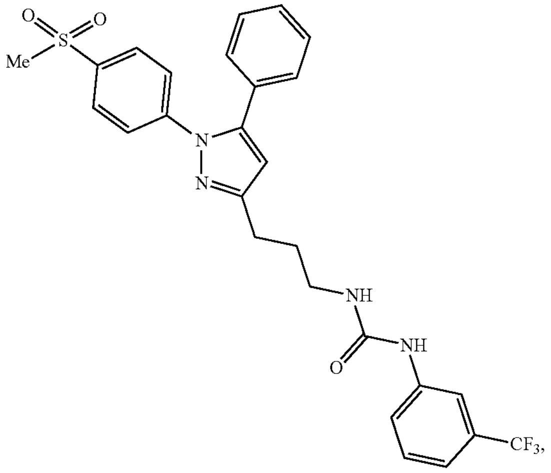
-continued
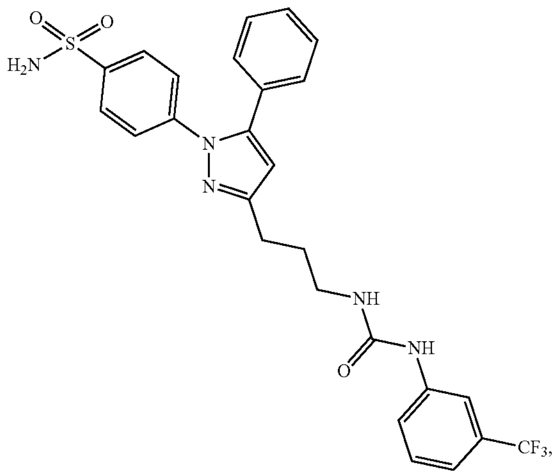
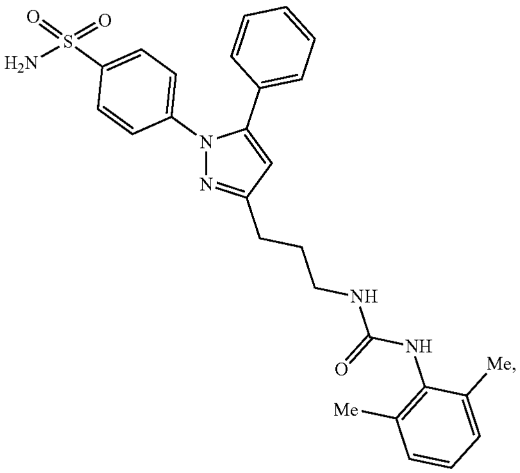
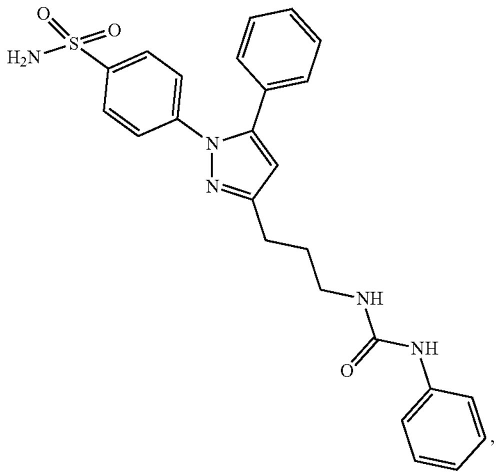

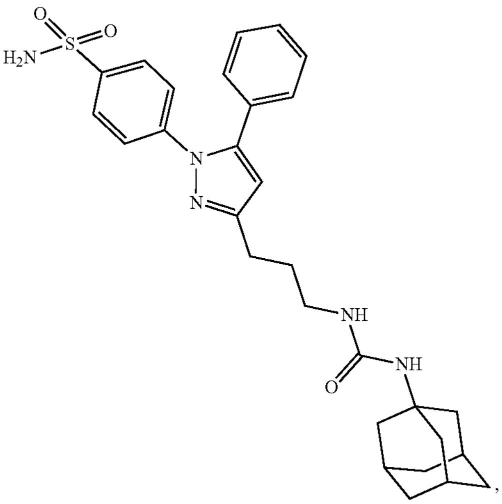
,
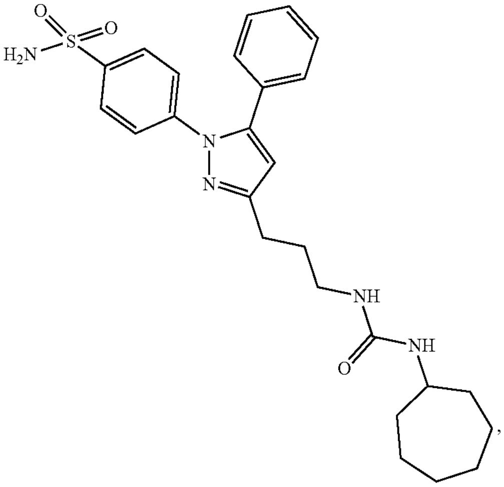
,
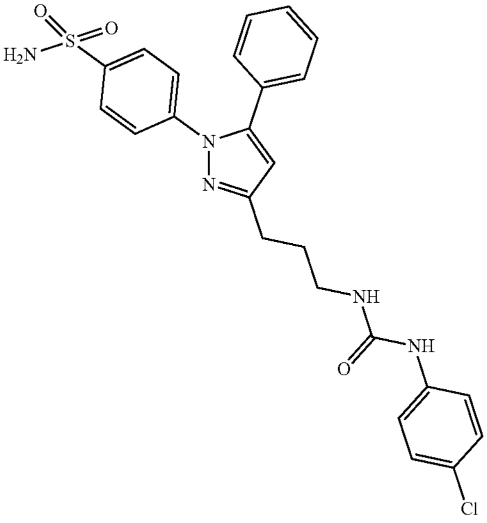
,
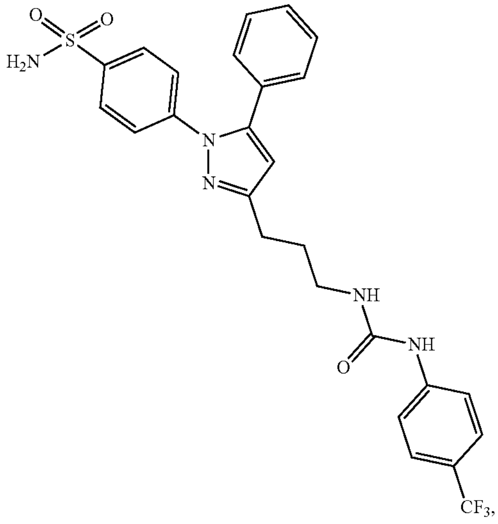
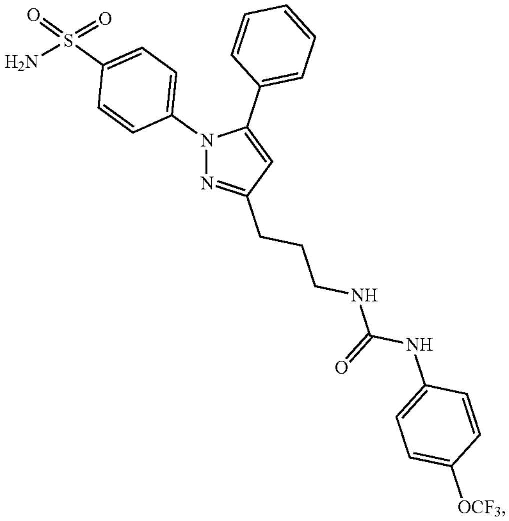
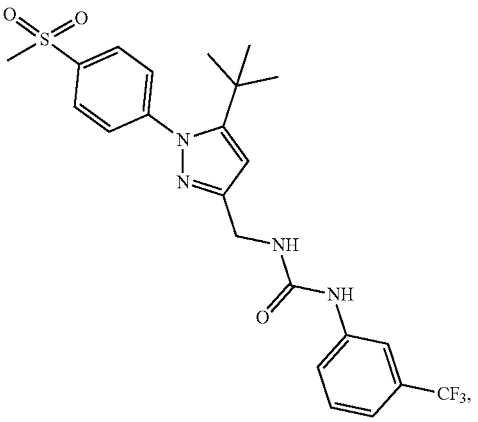
or -continued

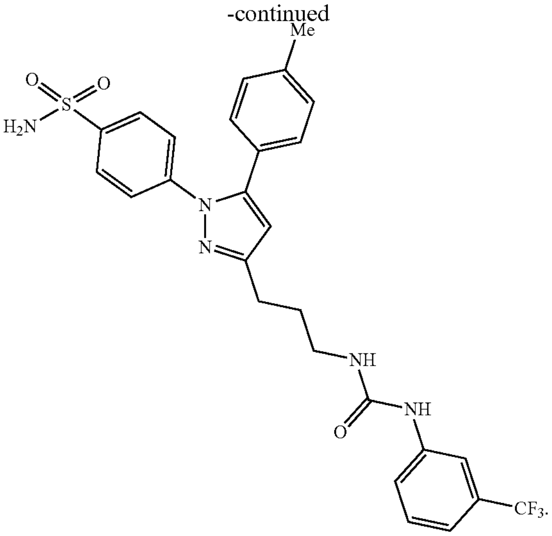

4. The method of claim 1, wherein the compound of Formula I is

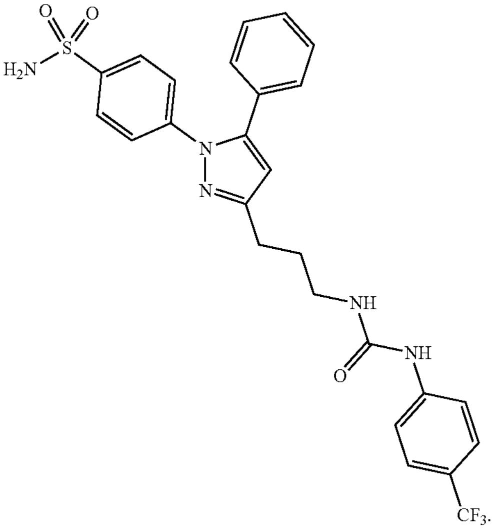 [SMILES: NS(=O)(=O)c1ccc(-n2nc(CCCNC(=O)Nc3ccc(C(F)(F)F)cc3)cc2-c2ccccc2)cc1]

5. The method of claim 2, wherein the subject is a human, a canine or a feline.

6. The method of claim 1, wherein the subject is a human.

7. The method of claim 1, wherein the compound of Formula I or the dual cyclooxygenase-2 (COX-2)/inhibitor of soluble epoxide hydrolase (sEH) is administered orally, buccally, transmucosally or topically.

8. The method of claim 1, wherein the dual cyclooxygenase-2 (COX-2)/inhibitor of soluble epoxide hydrolase (sEH) is administered to the oral cavity.

* * * * *